(12) United States Patent
van der Donk et al.

(10) Patent No.: US 11,149,270 B2
(45) Date of Patent: Oct. 19, 2021

(54) BIOSYNTHESIS AND ENGINEERING OF LANTHIPEPTIDES

(71) Applicant: The Board of Trustees of the University of Illinois, Urbana, IL (US)

(72) Inventors: Wilfred A. van der Donk, Urbana, IL (US); Ayse Okesli, Stanford, CA (US); Xiao Yang, Urbana, IL (US); Mark Walker, Champaign, IL (US); Kenton J. Hetrick, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 485 days.

(21) Appl. No.: 15/326,751

(22) PCT Filed: Sep. 28, 2015

(86) PCT No.: PCT/US2015/052724
§ 371 (c)(1),
(2) Date: Jan. 17, 2017

(87) PCT Pub. No.: WO2016/049656
PCT Pub. Date: Mar. 31, 2016

(65) Prior Publication Data
US 2017/0204400 A1  Jul. 20, 2017

Related U.S. Application Data

(60) Provisional application No. 62/056,216, filed on Sep. 26, 2014.

(51) Int. Cl.
*C40B 40/10* (2006.01)
*C12N 15/10* (2006.01)

(52) U.S. Cl.
CPC .......... *C12N 15/1037* (2013.01); *C40B 40/10* (2013.01)

(58) Field of Classification Search
None
See application file for complete search history.

(56) References Cited

U.S. PATENT DOCUMENTS

2009/0143295 A1    6/2009  O'Brien

FOREIGN PATENT DOCUMENTS

EP    2405008 A1    1/2012

OTHER PUBLICATIONS

Bennett, N. J., et al., "Characterization of a dual-function domain that mediates membrane insertion and excision of Ff filamentous bacteriophage," Journal of Molecular Biology 411, 972-985 (2011).
Berks, B., et al., "The Tat protein export pathway," Molecular Microbiology 35(2) 260-274 (2000).
Boder, E. T., et al., "Directed evolution of antibody fragments with monovalent femtomolar antigen-binding affinity," Proc Natl Acad Sci U S A 2000, 97:10701-5.
Boder, E. T., "Yeast surface display for screening combinatorial polypeptide libraries," Nat Biotechnol 15:553-7 (1997).
(Continued)

*Primary Examiner* — Christian C Boesen
(74) *Attorney, Agent, or Firm* — Klintworth & Rozenblat IP LLP

(57) ABSTRACT

Platforms, systems and methods are provided for identifying engineered lanthipeptide display peptides expressed in vivo from biological organisms.

6 Claims, 38 Drawing Sheets

Specification includes a Sequence Listing.

(56) References Cited

OTHER PUBLICATIONS

Bonardi, F., "Probing the SecYEG translocation pore size with preproteins conjugated with sizable rigid spherical molecules," P. Natl. Acad. Sci. 108:7775-7780 (2011).

Bosma, T., "Bacterial Display and Screening of Posttranslationally Thioether-Stabilized Peptides," Appl. Environ. Microb. 77:6794-6801 (2011).

Bratkovič, T. "Progress in phage display: evolution of the technique and its applications," Cell. Mol. Life Sci. 67:749-767 (2010).

Chatterjee, C., et al., Paul, M., Xie, L., and van der Donk, W. A. "Biosynthesis and Mode of Action of Lantibiotics," Chem. Rev. 105:633-684 (2005).

Chen, N., et al., Modified Recombinant Proteins Can Be Exported via the Sec Pathway in *Escherichia coli*, PLoS ONE 7:e42519 (2012).

Cobb, R.E., et al., "High-Efficiency Multiplex Genome Editing of *Streptomyces* Species Using an Engineered CRISPR/Cas System," ACS Synth. Biol., 4 (6), 723-728 (2015).

Edgar, R., et al., "High-sensitivity bacterial detection using biotin-tagged phage and quantum-dot nanocomplexes," Proc. Nat. Acad. Sci. USA 103:4841-4845 (2006).

Field, D., et al., "Bioengineered Nisin A Derivatives with Enhanced Activity against Both Gram Positive and Gram Negative Pathogens," PLoS ONE 7:e46884 (2012).

Fischbach, M. A., et al., "Antibiotics for Emerging Pathogens," Science 325:1089-1093 (2009).

Hasper, H. E., et al., "Assembly and stability of nisin-lipid II pores," Biochemistry 43:11567-11575 (2004).

Heinis, C., et al., "Phage-encoded combinatorial chemical libraries based on bicyclic peptides," Nat. Chem. Biol. 5:502-507 (2009).

Hess, G. T., et al., "M13 Bacteriophage Display Framework That Allows Sortase-Mediated Modification of Surface-Accessible Phage Proteins," Bioconjugate Chem. 23:1478-1487 (2012).

Hofmann, F. T., et al., "In Vitro Selection of Functional Lantipeptides," J. Am. Chem. Soc. 134:8038-8041 (2012).

Hsu, S. T., et al., "The nisin-lipid II complex reveals a pyrophosphate cage that provides a blueprint for novel antibiotics," Nat. Struct. Mol. Biol. 11:963-967 (2004).

Kieke, M. C., et al., "Selection of functional T cell receptor mutants from a yeast surface-display library," Proc Natl Acad Sci U S A 96:5651-6 (1999).

Knerr, P. J., et al., "Discovery, Biosynthesis, and Engineering of Lantipeptides," Annu. Rev. Biochem. 81:479-505 (2012).

Knerr, P. J., et al., "Non-proteinogenic Amino Acids in Lacticin 481 Analogues Result in More Potent Inhibition of Peptidoglycan Transglycosylation," ACS Chem. Biol. 7:1791-1795 (2012).

Koehn, F. E., et al., "The evolving role of natural products in drug discovery," Nat. Rev. Drug Discov. 4:206-220 (2005).

Kuipers, A., et al., "Sec-Mediated Transport of Posttranslationally Dehydrated Peptides in Lactococcus lactis," Applied and Environmental Microbiology 72:7626-7633 (2006).

Labrie, S.J., et al., "Bacteriophage Resistance Mechanisms," Nat. Rev. Microbiol. 8: 317-327 (2010).

Lavigne, R., et al., "Phage Proteomics: Applications of Mass Spectrometry" In: Clokie, M.R.J., and Kropinski, A.M. (Eds.), Bacteriohpages: Methods and Protocols, vol. 2: Molecular and Applied Aspects, vol. 502. Humana Press, New York, NY, 2009, pp. 239-254.

Li, B. et al., Catalytic promiscuity in the biosynthesis of cyclic peptide secondary metabolites in planktonic marine cyanobacteria, Proc. Natl. Acad. Sci., USA 107:10430-10435 (2010).

Li, K., et al., "Chemical Modification of M13 Bacteriophage and Its Application in Cancer Cell Imaging," Bioconjugate Chem. 21:1369-1377 (2010).

Love, K. R., et al., "Enabling Glycosyltransferase Evolution: A Facile Substrate-Attachment Strategy for Phage-Display Enzyme Evolution," ChemBioChem 7:753-756 (2006).

Makino, A., et al., "Cinnamycin (Ro 09-0198) promotes cell binding and toxicity by inducing transbilayer lipid movement," J. Biol. Chem. 278:3204-3209 (2003).

Mukherjee S, Van Der Donk WA, "Mechanistic Studies on the Substrate-Tolerant Lanthipeptide Synthetase" ProcM. J. Am. Chem. Soc. 2014, 136:10450-10459).

Ng, S., et al., "Bacteriophages and Viruses as a Support for Organic Synthesis and Combinatorial Chemistry," ACS Chem. Biol. 7:123-138 (2011).

Ökesli, A., et al., "Nine Post-translational Modifications during the Biosynthesis of Cinnamycin," J. Am. Chem. Soc. 133:13753-13760 (2011).

Oman, T. J., et al., "Haloduracin α binds the peptidoglycan precursor lipid II with 2:1 stoichiometry," J. Am. Chem. Soc. 133:17544 (2011).

Qi, H., et al., "Phagemid Vectors for Phage Display: Properties, Characteristics and Construction," J. Mol. Biol. 417:129-143 (2012).

Sachdev S, S. (2001) Engineering M13 for phage display, Biomol. Eng. 18, 57-63 (2001).

Shi, Y., et al., "Production of lantipeptides in *Escherichia coli*," J. Am. Chem. Soc. 133:2338-2341 (2010).

Smelyanski, L., et al., "Site directed biotinylation of filamentous phage structural proteins," Virol. J. 8:495 (2011).

Smith, G.P., "Absorption Spectroscopy and Quantitation of Filamentous Phage" from http://www.biosci.missouri.edu/smithgp/PhageDisplayWebsite/AbsorptionSpectrum.doc accessed on Aug. 19, 2015.

Sunbul, M., et al., "Enzyme-Catalyzed Substrate Attachment to Phage Surfaces for the Selection of Catalytic Activities," ChemBioChem 12:380-386 (2011).

Tacconelli, E., et al., "Does antibiotic exposure increase the risk of methicillin-resistant *Staphylococcus aureus* (MRSA) isolation? A systematic review and meta-analysis," J. Antimicrob. Chemother. 61:26-38 (2008).

Tang, W., et al., "Structural Characterization of Four Prochlorosins: A Novel Class of Lantipeptides Produced by Planktonic Marine Cyanobacteria," Biochemistry 51:4271-4279 (2012); Li, B. et al. (2010). Zhang, Q. et al. (2014).

Thomas, J. D., et al., "Export of active green fluorescent protein to the periplasm by the twinarginine translocase (Tat) pathway in *Escherichia coli*," Mol. Microbiol. 39:47-53 (2001).

Van Der Meer, J. R., et al., "Characterization of the Lactococcus lactis nisin A operon genes nisP, encoding a subtilisin-like serine protease involved in precursor processing, and nisR, encoding a regulatory protein involved in nisin biosynthesis," J. Bacteriol. 175:2578-2588 (1993).

Van Wezenbeek, P.M.G.F., et al., "Nucleotide sequence of the filamentous bacteriophage M13 DNA genome: comparison with phage fd," Gene. 11:129-148 (1980).

Wiseman, R.L., et al., "Different arrangements of protein subunits and single-stranded circular DNA in the filamentous bacterial viruses fd and Pf1," J. Mol. Biol., 102, 549-561 (1976).

Zhang, Q., et al., "High divergence of the precursor peptides in combinatorial lanthipeptide biosynthesis" ACS Chem. Biol. 2686-2694 (2014).

Boder E T et al: "Yeast Surface Display for Screening Combinatorial Polypeptide Libraries", Nature Biotechnology, Nature Publishing Group, US, 15:553-557 (1997).

Bosma Tjibbe et al: "Bacterial Display and Screening of Post-translationally Thioether-Stabilized Peptides", Applied and Environmental Microbiology, American Society for Microbiology, US, 77 (19):6794-6801 (2011).

Tomaz Bratkovi C: "Progress in phage display: evolution of the technique and its applications", CMLS Cellular and Molecular Life Sciences, Birkhauser-Verlag, BA, 67(5):749-767 (2009).

Jasmin Dischinger et al: "Lantibiotics: Promising candidates for future applications in health care", International Journal of Medical Microbiology, 304(1):51-62 (2014).

Patrick J. Knerr et al: 11 Discovery, Biosynthesis, and Engineering of Lantipeptides, Annual Review of Biochemistry, 81(1):479-505 (2012).

(56) References Cited

OTHER PUBLICATIONS

Montalban-Lopez Manuel et al: "Increasing the success rate of lantibiotic drug discovery by Synthetic Biology", Expert Opinion on Drug Discovery Aug. 2012, 7(8):695-709 (2012).
Joanne M. Willey et al: "Lantibiotics: Peptides of Diverse Structure and Function," Annual Review of Microbiology, 61(1):477-501 (2007).
International Search Report for PCT/US2015/052724 dated Dec. 1, 2015, six pages.
Written Opinion of the International Searching Authority for PCT/US2015/052724 dated Dec. 1, 2015, seven pages.

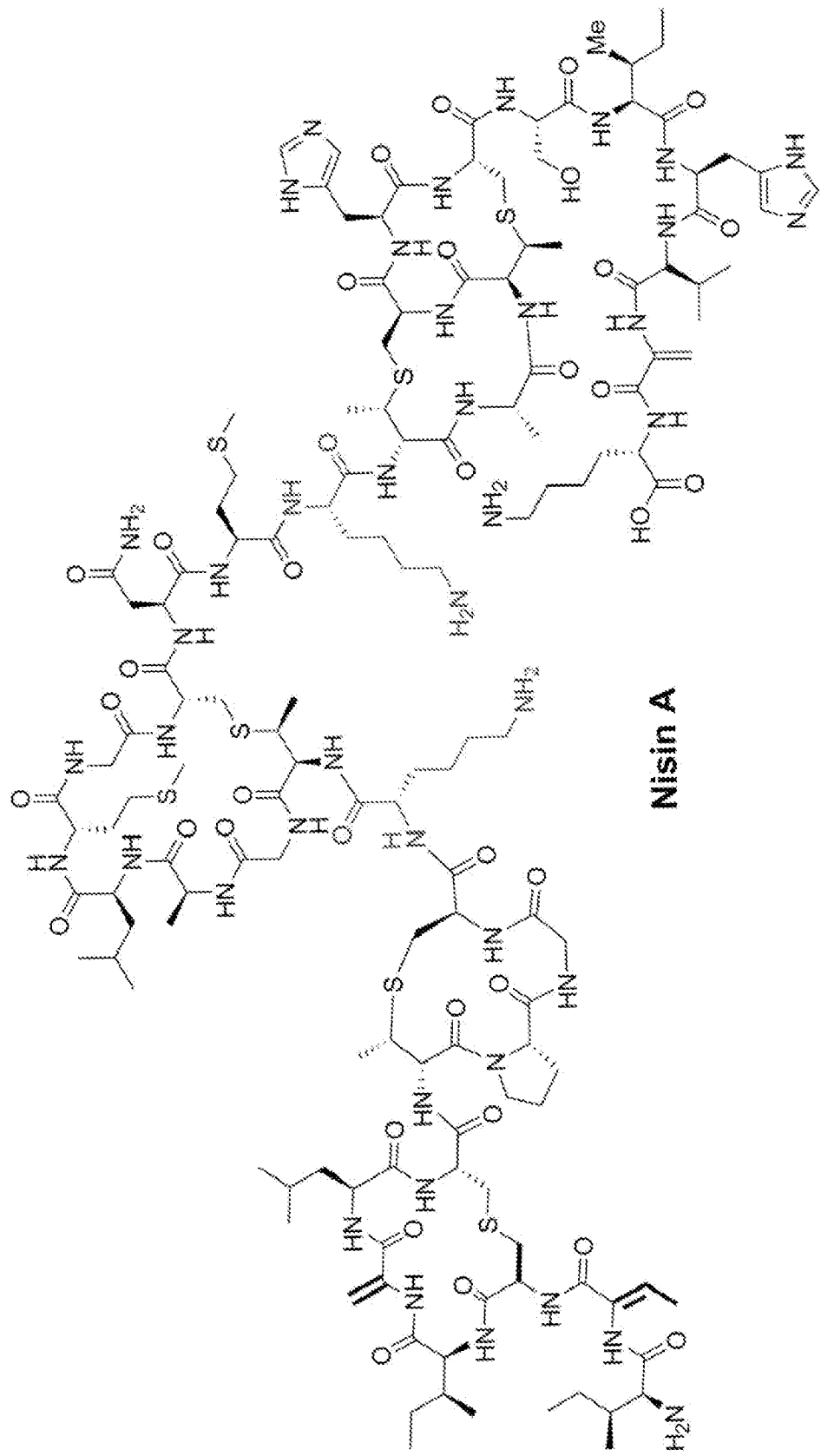
FIG. 4C Nisin A (SEQ ID NO.: 5)

CXXXXX Dha M P P Dha XXXXC
         |  |  |
         y8 y9 y10

(SEQ ID NO.: 6)

FIG. 7B (i)

Lacticin 481 (SEQ ID NO.: 105)

(ii)

(SEQ ID NO.: 106)

(iii)

Haloduracin α (SEQ ID NO.: 107)

SEQUENCE LISTING

```
<160> NUMBER OF SEQ ID NOS: 107

<210> SEQ ID NO 1
<211> LENGTH: 34
<212> TYPE: PRT
<213> ORGANISM: Artificial Sequence
<220> FEATURE:
<223> OTHER INFORMATION: SYNTHETIC NisA PEPTIDE SEQUENCE

<400> SEQUENCE: 1

Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30

Ser Lys

<210> SEQ ID NO 2
<211> LENGTH: 34
<212> TYPE: PRT
```

<213> ORGANISM: Artificial Sequence
<220> FEATURE:
<223> OTHER INFORMATION: SYNTHETIC NisA PEPTIDFE SEQUENCE PROCESSED BY
      NisB
<220> FEATURE:
<221> NAME/KEY: MISC_FEATURE
<222> LOCATION: (2)..(2)
<223> OTHER INFORMATION: X is dehydrobutyrine (Dhb).
<220> FEATURE:
<221> NAME/KEY: MISC_FEATURE
<222> LOCATION: (3)..(3)
<223> OTHER INFORMATION: X is dehydroalanine (Dha).
<220> FEATURE:
<221> NAME/KEY: MISC_FEATURE
<222> LOCATION: (5)..(5)
<223> OTHER INFORMATION: X is dehydroalanine (Dha).
<220> FEATURE:
<221> NAME/KEY: MISC_FEATURE
<222> LOCATION: (8)..(8)
<223> OTHER INFORMATION: X is dehydrobutyrine (Dhb).
<220> FEATURE:
<221> NAME/KEY: MISC_FEATURE
<222> LOCATION: (13)..(13)
<223> OTHER INFORMATION: X is dehydrobutyrine (Dhb).
<220> FEATURE:
<221> NAME/KEY: MISC_FEATURE
<222> LOCATION: (23)..(23)
<223> OTHER INFORMATION: X is dehydrobutyrine (Dhb).
<220> FEATURE:
<221> NAME/KEY: MISC_FEATURE
<222> LOCATION: (25)..(25)
<223> OTHER INFORMATION: X is dehydrobutyrine (Dhb).
<220> FEATURE:
<221> NAME/KEY: MISC_FEATURE
<222> LOCATION: (33)..(33)
<223> OTHER INFORMATION: X is dehydroalanine (Dha).

<400> SEQUENCE: 2

Ile Xaa Xaa Ile Xaa Leu Cys Xaa Pro Gly Cys Lys Xaa Gly Ala Leu
1               5                   10                  15

Met Gly Cys Asn Met Lys Xaa Ala Xaa Cys His Cys Ser Ile His Val
            20                  25                  30

Xaa Lys

<210> SEQ ID NO 3
<211> LENGTH: 34
<212> TYPE: PRT
<213> ORGANISM: Artificial Sequence
<220> FEATURE:
<223> OTHER INFORMATION: SYNTHETIC NisA PEPTIDFE SEQUENCE PROCESSED BY
      NisC.
<220> FEATURE:
<221> NAME/KEY: MISC_FEATURE
<222> LOCATION: (2)..(2)
<223> OTHER INFORMATION: X is dehydrobutyrine (Dhb).
<220> FEATURE:
<221> NAME/KEY: MISC_FEATURE
<222> LOCATION: (5)..(5)
<223> OTHER INFORMATION: X is dehydroalanine (Dha).
<220> FEATURE:
<221> NAME/KEY: MISC_FEATURE
<222> LOCATION: (8)..(8)
<223> OTHER INFORMATION: X is Abu.
<220> FEATURE:
<221> NAME/KEY: MISC_FEATURE
<222> LOCATION: (13)..(13)
<223> OTHER INFORMATION: X is Abu.
<220> FEATURE:
<221> NAME/KEY: MISC_FEATURE
<222> LOCATION: (23)..(23)
<223> OTHER INFORMATION: X is Abu.
<220> FEATURE:
<221> NAME/KEY: MISC_FEATURE
<222> LOCATION: (25)..(25)
<223> OTHER INFORMATION: X is Abu.

```
<220> FEATURE:
<221> NAME/KEY: MISC_FEATURE
<222> LOCATION: (33)..(33)
<223> OTHER INFORMATION: X is dehydroalanine (Dha).

<400> SEQUENCE: 3

Ile Xaa Ala Ile Xaa Leu Ala Xaa Pro Gly Ala Lys Xaa Gly Ala Leu
1               5                   10                  15

Met Gly Ala Asn Met Lys Xaa Ala Xaa Ala His Ala Ser Ile His Val
            20                  25                  30

Xaa Lys

<210> SEQ ID NO 4
<211> LENGTH: 34
<212> TYPE: PRT
<213> ORGANISM: Artificial Sequence
<220> FEATURE:
<223> OTHER INFORMATION: Nisin Polypeptide containing sulfide bonds
      between residus 3 and 7; between residues 8 and 11; between
      residues 13 and 19; between residues 23 and 26; and between
      residues 25 and 28.
<220> FEATURE:
<221> NAME/KEY: MISC_FEATURE
<222> LOCATION: (2)..(2)
<223> OTHER INFORMATION: X is dehydrobutyrine (Dhb).
<220> FEATURE:
<221> NAME/KEY: MISC_FEATURE
<222> LOCATION: (5)..(5)
<223> OTHER INFORMATION: X is dehydroalanine (Dha).
<220> FEATURE:
<221> NAME/KEY: MISC_FEATURE
<222> LOCATION: (8)..(8)
<223> OTHER INFORMATION: X is Abu.
<220> FEATURE:
<221> NAME/KEY: MISC_FEATURE
<222> LOCATION: (13)..(13)
<223> OTHER INFORMATION: X is Abu.
<220> FEATURE:
<221> NAME/KEY: MISC_FEATURE
<222> LOCATION: (23)..(23)
<223> OTHER INFORMATION: X is Abu.
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: MISC_FEATURE
<222> LOCATION: (33)..(33)
<223> OTHER INFORMATION: X is dehydroalanine (Dha)

<400> SEQUENCE: 4

Ile Xaa Ala Ile Xaa Leu Ala Xaa Pro Gly Ala Lys Xaa Gly Ala Leu
1               5                   10                  15

Met Gly Ala Asn Met Lys Xaa Ala Xaa Ala His Ala Ser Ile His Val
            20                  25                  30

Xaa Lys

<210> SEQ ID NO 5
<211> LENGTH: 13
<212> TYPE: PRT
<213> ORGANISM: Artificial Sequence
<220> FEATURE:
<223> OTHER INFORMATION: SYNTHETIC POLYPEPTIDE SEQUENCE
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
```

```
<400> SEQUENCE: 5

Ala Ala Cys Xaa Xaa Xaa Xaa Met Pro Pro Ser Xaa Xaa
1               5                   10

<210> SEQ ID NO 6
<211> LENGTH: 17
<212> TYPE: PRT
<213> ORGANISM: Artificial Sequence
<220> FEATURE:
<223> OTHER INFORMATION: SYNTHETIC POLYPEPTIDE SEQUENCE
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: X is dehydroalanine (Dha).
<220> FEATURE:
<221> NAME/KEY: MISC_FEATURE
<222> LOCATION: (11)..(11)
<223> OTHER INFORMATION: X is dehydroalanine (Dha).
<220> FEATURE:
<221> NAME/KEY: misc_feature
<222> LOCATION: (12)..(16)
<223> OTHER INFORMATION: Xaa can be any naturally occurring amino acid

<400> SEQUENCE: 6

Cys Xaa Xaa Xaa Xaa Xaa Xaa Met Pro Pro Xaa Xaa Xaa Xaa Xaa Xaa
1               5                   10                  15

Cys

<210> SEQ ID NO 7
<211> LENGTH: 16
<212> TYPE: PRT
<213> ORGANISM: Artificial Sequence
<220> FEATURE:
<223> OTHER INFORMATION: SYNTHETIC PROCHLOROSIN 1.1 POLYPEPTIDE
<220> FEATURE:
<221> NAME/KEY: MISC_FEATURE
<222> LOCATION: (7)..(7)
<223> OTHER INFORMATION: X is Abu.
<220> FEATURE:
<221> NAME/KEY: MISC_FEATURE
<222> LOCATION: (12)..(12)
<223> OTHER INFORMATION: X is Abu.

<400> SEQUENCE: 7

Phe Phe Ala Val Gln Gly Xaa Ala Asn Arg Phe Xaa Ile Asn Val Ala
1               5                   10                  15

<210> SEQ ID NO 8
<211> LENGTH: 19
<212> TYPE: PRT
<213> ORGANISM: Artificial Sequence
<220> FEATURE:
<223> OTHER INFORMATION: SYNTHETIC PROCHLOROSIN 2.8 POLYPEPTIDE SEQUENCE

<400> SEQUENCE: 8

Ala Ala Ala His Gln His Ala Pro Ala Met Pro Pro Ala Tyr Trp Glu
1               5                   10                  15

Gly Glu Ala

<210> SEQ ID NO 9
<211> LENGTH: 17
<212> TYPE: PRT
<213> ORGANISM: Artificial Sequence
<220> FEATURE:
```

```
<223> OTHER INFORMATION: ProcA 2.8 SYNTHETIC CORE REGION POLYPEPTIDE
      SEQUENCE
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (12)..(16)
<223> OTHER INFORMATION: Xaa can be any naturally occurring amino acid

<400> SEQUENCE: 9

Cys Xaa Xaa Xaa Xaa Xaa Ser Met Pro Pro Ser Xaa Xaa Xaa Xaa Xaa
1               5                   10                  15

Cys

<210> SEQ ID NO 10
<211> LENGTH: 19
<212> TYPE: PRT
<213> ORGANISM: Artificial Sequence
<220> FEATURE:
<223> OTHER INFORMATION: ProA 2.8-1 SYNTHETIC CORE POLYPEPTIDE SEQUENCE

<400> SEQUENCE: 10

Ala Ala Cys Phe Asn Val His Ile Ser Met Pro Pro Ser His Asn Asn
1               5                   10                  15

Val His Cys

<210> SEQ ID NO 11
<211> LENGTH: 19
<212> TYPE: PRT
<213> ORGANISM: Artificial Sequence
<220> FEATURE:
<223> OTHER INFORMATION: ProA 2.8-2 SYNTHETIC CORE POLYPEPTIDE SEQUENCE

<400> SEQUENCE: 11

Ala Ala Cys Asp Val Asn Leu His Ser Met Pro Pro Ser Leu Asp Phe
1               5                   10                  15

Phe Val Cys

<210> SEQ ID NO 12
<211> LENGTH: 19
<212> TYPE: PRT
<213> ORGANISM: Artificial Sequence
<220> FEATURE:
<223> OTHER INFORMATION: ProA 2.8-3 SYNTHETIC CORE POLYPEPTIDE SEQUENCE

<400> SEQUENCE: 12

Ala Ala Cys Val Phe His Phe Asp Ser Met Pro Pro Ser Tyr Leu Asp
1               5                   10                  15

Asp Asp Cys

<210> SEQ ID NO 13
<211> LENGTH: 19
<212> TYPE: PRT
<213> ORGANISM: Artificial Sequence
<220> FEATURE:
<223> OTHER INFORMATION: ProA 2.8-4 SYNTHETIC CORE POLYPEPTIDE SEQUENCE

<400> SEQUENCE: 13

Ala Ala Cys Asn Ile Asp Phe Leu Ser Met Pro Pro Ser Ile His His
1               5                   10                  15

Ile Leu Cys
```

```
<210> SEQ ID NO 14
<211> LENGTH: 19
<212> TYPE: PRT
<213> ORGANISM: Artificial Sequence
<220> FEATURE:
<223> OTHER INFORMATION: ProA 2.8-5 SYNTHETIC CORE POLYPEPTIDE SEQUENCE

<400> SEQUENCE: 14

Ala Ala Cys Asn Ile Tyr Tyr Ile Ser Met Pro Pro Ser His His Phe
1               5                   10                  15

Val Tyr Cys

<210> SEQ ID NO 15
<211> LENGTH: 19
<212> TYPE: PRT
<213> ORGANISM: Artificial Sequence
<220> FEATURE:
<223> OTHER INFORMATION: ProA 2.8-6 SYNTHETIC CORE POLYPEPTIDE SEQUENCE

<400> SEQUENCE: 15

Ala Ala Cys His Asp Asn Asn Asn Ser Met Pro Pro Ser Phe Tyr His
1               5                   10                  15

Ile Phe Cys

<210> SEQ ID NO 16
<211> LENGTH: 19
<212> TYPE: PRT
<213> ORGANISM: Artificial Sequence
<220> FEATURE:
<223> OTHER INFORMATION: ProA 2.8-7 SYNTHETIC CORE POLYPEPTIDE SEQUENCE

<400> SEQUENCE: 16

Ala Ala Cys His Leu Asn Tyr Asn Ser Met Pro Pro Ser Phe His Ile
1               5                   10                  15

Leu Phe Cys

<210> SEQ ID NO 17
<211> LENGTH: 19
<212> TYPE: PRT
<213> ORGANISM: Artificial Sequence
<220> FEATURE:
<223> OTHER INFORMATION: ProA 2.8-8 SYNTHETIC CORE POLYPEPTIDE SEQUENCE

<400> SEQUENCE: 17

Ala Ala Cys Leu Asn Asn Leu Val Ser Met Pro Pro Ser Asn Ile Val
1               5                   10                  15

Val Tyr Cys

<210> SEQ ID NO 18
<211> LENGTH: 19
<212> TYPE: PRT
<213> ORGANISM: Artificial Sequence
<220> FEATURE:
<223> OTHER INFORMATION: ProA 2.8-9 SYNTHETIC CORE POLYPEPTIDE SEQUENCE

<400> SEQUENCE: 18

Ala Ala Cys Asn Ile His Ile Tyr Ser Met Pro Pro Ser Asn Asn His
1               5                   10                  15

Phe Asn Cys

<210> SEQ ID NO 19
<211> LENGTH: 19
<212> TYPE: PRT
<213> ORGANISM: Artificial Sequence
```

```
<220> FEATURE:
<223> OTHER INFORMATION: ProA 2.8-10 SYNTHETIC CORE POLYPEPTIDE SEQUENCE

<400> SEQUENCE: 19

Ala Ala Cys His Asp Ile Asn Leu Ser Met Pro Pro Ser Phe Leu Asn
1               5                   10                  15

Val Ile Cys

<210> SEQ ID NO 20
<211> LENGTH: 19
<212> TYPE: PRT
<213> ORGANISM: Artificial Sequence
<220> FEATURE:
<223> OTHER INFORMATION: ProA 2.8-11 SYNTHETIC CORE POLYPEPTIDE SEQUENCE

<400> SEQUENCE: 20

Ala Ala Cys Ile Leu Tyr Leu Ile Ser Met Pro Pro Ser Asn Ile Phe
1               5                   10                  15

Asn Asp Cys

<210> SEQ ID NO 21
<211> LENGTH: 19
<212> TYPE: PRT
<213> ORGANISM: Artificial Sequence
<220> FEATURE:
<223> OTHER INFORMATION: ProA 2.8-12 SYNTHETIC CORE POLYPEPTIDE SEQUENCE

<400> SEQUENCE: 21

Ala Ala Cys Phe Phe Asp Ile Asn Ser Met Pro Pro Ser Asp Asp Leu
1               5                   10                  15

Tyr Leu Cys

<210> SEQ ID NO 22
<211> LENGTH: 19
<212> TYPE: PRT
<213> ORGANISM: Artificial Sequence
<220> FEATURE:
<223> OTHER INFORMATION: ProA 2.8-13 SYNTHETIC CORE POLYPEPTIDE SEQUENCE

<400> SEQUENCE: 22

Ala Ala Cys Leu Ile Val Asp Tyr Ser Met Pro Pro Ser Ile Asp Asn
1               5                   10                  15

His Leu Cys

<210> SEQ ID NO 23
<211> LENGTH: 19
<212> TYPE: PRT
<213> ORGANISM: Artificial Sequence
<220> FEATURE:
<223> OTHER INFORMATION: ProA 2.8-14 SYNTHETIC CORE POLYPEPTIDE SEQUENCE

<400> SEQUENCE: 23

Ala Ala Cys His Ile Asn Arg Ile Ser Met Pro Pro Ser Asp Ile Val
1               5                   10                  15

Asp Phe Cys

<210> SEQ ID NO 24
<211> LENGTH: 19
<212> TYPE: PRT
<213> ORGANISM: Artificial Sequence
<220> FEATURE:
<223> OTHER INFORMATION: ProA 2.8-15 SYNTHETIC CORE POLYPEPTIDE SEQUENCE

<400> SEQUENCE: 24
```

Ala Ala Cys His His Asn Asn Leu Ser Met Pro Pro Ser Asp Tyr Phe
1               5                   10                  15

Val Leu Cys

<210> SEQ ID NO 25
<211> LENGTH: 19
<212> TYPE: PRT
<213> ORGANISM: Artificial Sequence
<220> FEATURE:
<223> OTHER INFORMATION: ProA 2.8-16 SYNTHETIC CORE POLYPEPTIDE SEQUENCE

<400> SEQUENCE: 25

Ala Ala Cys Asn Asp Asn Asn Ile Ser Met Pro Pro Ser Ile Val Phe
1               5                   10                  15

Asp Phe Cys

<210> SEQ ID NO 26
<211> LENGTH: 19
<212> TYPE: PRT
<213> ORGANISM: Artificial Sequence
<220> FEATURE:
<223> OTHER INFORMATION: ProA 2.8-17 SYNTHETIC CORE POLYPEPTIDE SEQUENCE

<400> SEQUENCE: 26

Ala Ala Cys Ile Val Asn Tyr His Ser Met Pro Pro Ser Leu Asn Ile
1               5                   10                  15

Leu Tyr Cys

<210> SEQ ID NO 27
<211> LENGTH: 19
<212> TYPE: PRT
<213> ORGANISM: Artificial Sequence
<220> FEATURE:
<223> OTHER INFORMATION: ProA 2.8-18 SYNTHETIC CORE POLYPEPTIDE SEQUENCE

<400> SEQUENCE: 27

Ala Ala Cys His Leu His Ile Leu Ser Met Pro Pro Ser Val Tyr Ile
1               5                   10                  15

Phe Leu Cys

<210> SEQ ID NO 28
<211> LENGTH: 19
<212> TYPE: PRT
<213> ORGANISM: Artificial Sequence
<220> FEATURE:
<223> OTHER INFORMATION: ProA 2.8-19 SYNTHETIC CORE POLYPEPTIDE SEQUENCE

<400> SEQUENCE: 28

Ala Ala Cys Asn Phe Leu Val Asp Ser Met Pro Pro Ser Leu Phe Val
1               5                   10                  15

Ile Ile Cys

<210> SEQ ID NO 29
<211> LENGTH: 19
<212> TYPE: PRT
<213> ORGANISM: Artificial Sequence
<220> FEATURE:
<223> OTHER INFORMATION: PEPTIDE 3-3 SYNTHETIC CORE POLYPEPTIDE SEQUENCE

<400> SEQUENCE: 29

Ala Ala Cys Leu His Phe Phe Leu Ser Met Pro Pro Ser His Val Leu
1               5                   10                  15

Asp Ile Cys

<210> SEQ ID NO 30
<211> LENGTH: 43
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 30
gcgcgttggc cgattcatta atgcagtcaa gcccgccgta gcc             43

<210> SEQ ID NO 31
<211> LENGTH: 53
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 31
ccagtcggga aacctgtcgt gccagttcac ctagatcctt ttggttcatg tgc     53

<210> SEQ ID NO 32
<211> LENGTH: 39
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 32
ccgacgccgt agcggccgca ggcagcagcc atcaccatc                   39

<210> SEQ ID NO 33
<211> LENGTH: 53
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 33
ataatcaaaa tcaccggcgc ctttgcttac gtgaatacta caatgacaag ttg     53

<210> SEQ ID NO 34
<211> LENGTH: 47
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 34
acgtaagcaa aggcgccggt gattttgatt atgaaaagat ggcaaac          47

<210> SEQ ID NO 35
<211> LENGTH: 38
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 35
atggctgctg cctgcggccg ctacggcgtc ggtggcag                    38

<210> SEQ ID NO 36
<211> LENGTH: 32
<212> TYPE: DNA
<213> ORGANISM: Artificial Sequence

```
<220> FEATURE:
<223> OTHER INFORMATION: SYNTHETIC OLIGONUCLEOTIDE

<400> SEQUENCE: 36
ggttggttca tatggaaagt ccatcatctt gg                                    32

<210> SEQ ID NO 37
<211> LENGTH: 34
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 37
aagtagttgg taccttattc agtaggccag agac                                  34

<210> SEQ ID NO 38
<211> LENGTH: 62
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 38
agccggccat ggccatggat tataaggatg acgacgataa attcatgtca gaagaacaac      60
tc                                                                     62

<210> SEQ ID NO 39
<211> LENGTH: 42
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 39
tccaaacgtg cggccgcgca gtgaacgtta tgtgggatgg ag                         42

<210> SEQ ID NO 40
<211> LENGTH: 43
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 40
tccaaacgtg cggccgcgca gtgaacgtta ttgtgggatg gag                        43

<210> SEQ ID NO 41
<211> LENGTH: 50
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 41
agccaggatc cgaattcgat gtcagaagag caactgaagg cattcctcac                 50

<210> SEQ ID NO 42
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 42
```
tcccccagcc acaccttcca gctc                                          24

<210> SEQ ID NO 43
<211> LENGTH: 87
<212> TYPE: DNA
<213> ORGANISM: Artificial Sequence
<220> FEATURE:
<223> OTHER INFORMATION: SYNTHETIC OLIGONUCLEOTIDE
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 43
taaatattgc ggccgcttag carwnrwnrw nrwnggatgg aggcatagar wnrwnrwnrw    60
nrwnacaggc cgctccccca gccacac                                       87

<210> SEQ ID NO 44
<211> LENGTH: 85
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 44
taaatattgc ggccgcttag tagcawbmwb mwbmwbmwbm wbmwbmwbmw bmwbmwbact    60
gttgtagtga tggtatcccc cagcc                                         85

<210> SEQ ID NO 45
<211> LENGTH: 81
<212> TYPE: PRT
<213> ORGANISM: Artificial Sequence
<220> FEATURE:
<223> OTHER INFORMATION: ProcA 1.1 SYNTHETIC LEADER POLYPEPTIDE SEQUENCE

<400> SEQUENCE: 45

Met Ser Glu Glu Gln Leu Lys Ala Phe Ile Ala Lys Val Gln Ala Asp
1               5                   10                  15

Thr Ser Leu Gln Glu Gln Leu Lys Ala Glu Gly Ala Asp Val Ala
            20                  25                  30

Ile Ala Lys Ala Ala Gly Phe Ser Ile Thr Thr Glu Asp Leu Glu Lys
        35                  40                  45

Glu His Arg Gln Thr Leu Ser Asp Asp Leu Glu Gly Val Ala Gly
    50                  55                  60

Gly Phe Phe Cys Val Gln Gly Thr Ala Asn Arg Phe Thr Ile Asn Val
65                  70                  75                  80

Cys

<210> SEQ ID NO 46
<211> LENGTH: 95
<212> TYPE: PRT
<213> ORGANISM: Artificial Sequence
<220> FEATURE:
<223> OTHER INFORMATION: ProcA 1.2 SYNTHETIC LEADER POLYPEPTIDE SEQUENCE

<400> SEQUENCE: 46

Met Ser Glu Glu Gln Leu Lys Ala Phe Ile Ala Lys Val Gln Ala Asp
1               5                   10                  15

Pro Ser Leu Gln Glu Gln Leu Lys Ala Glu Gly Ala Asp Val Val Ser
            20                  25                  30

Ile Ala Lys Ala Ala Gly Phe Ser Ile Thr Thr Glu Asp Leu Asn Ser
        35                  40                  45

His Ile Thr Thr Lys Leu Asn Leu Ser Glu Glu Leu Glu Gly Val
    50                  55                  60

Ala Gly Ala Met Asp Cys Val Ser Ser Thr Ala Gln Gln Thr Glu Cys
65                  70                  75                  80

Arg Pro Gly Gly Pro Arg Ala Ser Tyr Cys Trp Asp Asp Leu Arg
                85                  90                  95

<210> SEQ ID NO 47
<211> LENGTH: 87
<212> TYPE: PRT
<213> ORGANISM: Artificial Sequence
<220> FEATURE:
<223> OTHER INFORMATION: ProcA 1.3 SYNTHETIC LEADER POLYPEPTIDE SEQUENCE

<400> SEQUENCE: 47

Met Ser Glu Glu Gln Leu Lys Gly Phe Leu Ser Lys Val Gln Ser Asp
1               5                   10                  15

Ala Ser Leu Gln Glu Gln Leu Lys Val Glu Gly Ala Asp Val Val Ala
            20                  25                  30

Ile Ala Lys Ala Ala Gly Phe Ser Ile Thr Thr Glu Asp Leu Asn Ser
        35                  40                  45

His Arg Gln Asn Leu Ser Glu Asp Glu Leu Glu Gly Val Ala Gly Gly
    50                  55                  60

Gly Leu Cys Thr Leu Thr Ser Asn Leu Ala Ala Val Cys Cys Gly Gly
65                  70                  75                  80

Cys Arg Arg Ala Thr Ser Glu
                85

<210> SEQ ID NO 48
<211> LENGTH: 81
<212> TYPE: PRT
<213> ORGANISM: Artificial Sequence
<220> FEATURE:
<223> OTHER INFORMATION: ProcA 1.4 SYNTHETIC LEADER POLYPEPTIDE SEQUENCE

<400> SEQUENCE: 48

Met Ser Glu Glu Gln Leu Lys Ala Phe Leu Thr Lys Val Gln Ala Asp
1               5                   10                  15

Thr Ser Leu Gln Glu Gln Leu Lys Ala Glu Gly Ala Asp Pro Val Ala
                20                  25                  30

Ile Ala Lys Ala Ala Gly Phe Ala Ile Thr Thr Glu Asp Leu Asn Ser
            35                  40                  45

His Arg Gln Asn Leu Ser Asp Asp Glu Leu Glu Gly Val Ala Gly Gly
        50                  55                  60

Gly Ser Ser Tyr Arg Asn Gly Lys Cys Thr Phe Gly Pro Ala Cys Pro
65                  70                  75                  80

Ser

<210> SEQ ID NO 49
<211> LENGTH: 87
<212> TYPE: PRT
<213> ORGANISM: Artificial Sequence
<220> FEATURE:
<223> OTHER INFORMATION: ProcA 1.5 SYNTHETIC LEADER POLYPEPTIDE SEQUENCE

<400> SEQUENCE: 49

Met Ser Glu Glu Gln Leu Lys Ala Phe Ile Ala Lys Val Gln Ala Asp
1               5                   10                  15

Thr Ser Leu Gln Glu Gln Leu Lys Val Glu Gly Ala Asp Val Val Ala
                20                  25                  30

Ile Ala Lys Ala Ala Gly Phe Ser Ile Thr Thr Glu Asp Leu Asn Thr
            35                  40                  45

His Arg Gln Asn Leu Ser Asp Asp Glu Leu Glu Gly Leu His Gly Ala
        50                  55                  60

Gly Pro Gly Cys Thr Gly Gly Trp Ala Phe Thr Asp Cys Thr Ala
65                  70                  75                  80

Gly Gly Gly Ser Cys Glu Gly
                85

<210> SEQ ID NO 50
<211> LENGTH: 91
<212> TYPE: PRT
<213> ORGANISM: Artificial Sequence
<220> FEATURE:
<223> OTHER INFORMATION: ProcA 1.6 SYNTHETIC LEADER POLYPEPTIDE SEQUENCE

<400> SEQUENCE: 50

Met Ser Glu Glu Gln Leu Lys Ala Phe Ile Ala Lys Val Gln Ala Asp
1               5                   10                  15

Thr Ser Leu Gln Glu Gln Leu Lys Val Glu Gly Ala Asp Val Val Ala
                20                  25                  30

Ile Ala Lys Ala Ala Gly Phe Ser Ile Thr Thr Asp Asp Phe Glu Arg
            35                  40                  45

Asn Thr His Arg Gln Thr Leu Ser Asp Asp Glu Leu Glu Gly Val Ala
        50                  55                  60

Gly Gly Lys Ser Thr Asn Gly Cys Gly Cys Lys Pro Gly His Thr Leu
65                  70                  75                  80

Ser Ser Phe Leu Cys Thr Leu Glu Cys Trp Leu
                85                  90

<210> SEQ ID NO 51
<211> LENGTH: 90
<212> TYPE: PRT
<213> ORGANISM: Artificial Sequence

```
<220> FEATURE:
<223> OTHER INFORMATION: ProcA 1.7 SYNTHETIC LEADER POLYPEPTIDE SEQUENCE

<400> SEQUENCE: 51

Met Ser Glu Glu Gln Leu Lys Ala Phe Ile Ala Lys Val Gln Ala Asp
1               5                   10                  15

Thr Ser Leu Gln Glu Gln Leu Lys Val Glu Gly Ala Asp Val Val Ala
            20                  25                  30

Ile Ala Lys Ala Ser Gly Phe Ala Ile Thr Thr Glu Asp Leu Lys Ala
        35                  40                  45

His Gln Ala Asn Ser Gln Lys Asn Leu Ser Asp Ala Glu Leu Glu Gly
    50                  55                  60

Val Ala Gly Gly Thr Ile Gly Gly Thr Ile Val Ser Ile Thr Cys Glu
65                  70                  75                  80

Thr Cys Asp Leu Leu Val Gly Lys Met Cys
                85                  90

<210> SEQ ID NO 52
<211> LENGTH: 93
<212> TYPE: PRT
<213> ORGANISM: Artificial Sequence
<220> FEATURE:
<223> OTHER INFORMATION: ProcA 2.1 SYNTHETIC LEADER POLYPEPTIDE SEQUENCE

<400> SEQUENCE: 52

Met Ser Glu Glu Gln Leu Lys Ala Phe Ile Ala Lys Val Gln Ala Asp
1               5                   10                  15

Ser Ser Leu Gln Glu Gln Leu Lys Ala Glu Gly Ala Asp Val Val Ala
            20                  25                  30

Ile Ala Lys Ala Ala Gly Phe Ser Ile Thr Thr Glu Asp Trp Asp Gln
        35                  40                  45

Arg Pro Val Arg Thr Leu Ser Asp Glu Glu Leu Glu Gly Ala Ala Gly
    50                  55                  60

Gly Cys Cys Ile Thr Gly Glu Ser Pro Gly Ser Ala Pro Thr Asn Asp
65                  70                  75                  80

Tyr Lys Cys Thr Lys Gly Arg Gly Pro Gly Gly Cys Tyr
                85                  90

<210> SEQ ID NO 53
<211> LENGTH: 85
<212> TYPE: PRT
<213> ORGANISM: Artificial Sequence
<220> FEATURE:
<223> OTHER INFORMATION: ProcA 2.2 SYNTHETIC LEADER POLYPEPTIDE SEQUENCE

<400> SEQUENCE: 53

Met Ser Glu Glu Gln Leu Lys Ala Phe Ile Ala Lys Val Gln Ala Asp
1               5                   10                  15

Pro Ser Leu Gln Glu Gln Leu Lys Ala Glu Gly Ala Asp Thr Val Ala
            20                  25                  30

Ile Ala Lys Ala Ala Gly Phe Ser Ile Thr Thr Glu Asp Leu Lys Glu
        35                  40                  45

His Arg Gln Thr Leu Ser Asp Asp Glu Leu Glu Ser Val Ala Gly Gly
    50                  55                  60

Gly Asn Asp Thr Val Ile Thr Lys Glu Tyr Ser Cys Tyr Val Thr Ser
65                  70                  75                  80

Asp Lys Gly Cys Cys
                85
```

<210> SEQ ID NO 54
<211> LENGTH: 89
<212> TYPE: PRT
<213> ORGANISM: Artificial Sequence
<220> FEATURE:
<223> OTHER INFORMATION: ProcA 2.3 SYNTHETIC LEADER POLYPEPTIDE SEQUENCE

<400> SEQUENCE: 54

```
Met Ser Glu Glu Gln Leu Lys Ala Phe Leu Glu Lys Val Lys Ala Asp
1               5                   10                  15

Thr Ser Leu Lys Glu Lys Leu Lys Ala Ala Lys Ser Pro Glu Asp Val
            20                  25                  30

Val Gly Ile Ala Lys Glu His Gly His Glu Phe Thr Ala Asp Lys Ile
        35                  40                  45

Ser Gln Leu Ser Glu Glu Leu Glu Gly Val Ala Gly Gly Met Gln
    50                  55                  60

Ala Gly Ser Cys Asn Trp Ile Cys Phe Val Asn Gly Val Tyr Ile Asn
65                  70                  75                  80

Asp Gly Arg Met Ala Asn Lys Ala Ile
                85
```

<210> SEQ ID NO 55
<211> LENGTH: 82
<212> TYPE: PRT
<213> ORGANISM: Artificial Sequence
<220> FEATURE:
<223> OTHER INFORMATION: ProcA 2.4  SYNTHETIC LEADER POLYPEPTIDE
      SEQUENCE

<400> SEQUENCE: 55

```
Met Ser Glu Glu Gln Leu Lys Ala Phe Leu Ala Lys Val Gln Ala Asp
1               5                   10                  15

Ala Ser Leu Gln Glu Gln Leu Lys Ala Glu Gly Ala Asp Val Val Ala
            20                  25                  30

Ile Ala Lys Ala Ala Gly Phe Ser Ile Thr Thr Glu Asp Leu Asn Ser
        35                  40                  45

His Arg Gln Ile Glu Met Thr Asp Asp Glu Leu Glu Gly Val Ala Gly
    50                  55                  60

Gly Gly Cys Gly Leu Gly Ala Arg Arg Glu Thr Ala Gln Cys Trp Leu
65                  70                  75                  80

Ser His
```

<210> SEQ ID NO 56
<211> LENGTH: 96
<212> TYPE: PRT
<213> ORGANISM: Artificial Sequence
<220> FEATURE:
<223> OTHER INFORMATION: ProcA 2.5 SYNTHETIC LEADER POLYPEPTIDE
      SEQUENCE

<400> SEQUENCE: 56

```
Met Ser Glu Glu Gln Leu Lys Ala Phe Ile Ala Lys Val Gln Gly Asp
1               5                   10                  15

Thr Ser Leu Gln Glu Gln Leu Lys Ala Glu Gly Ala Asp Val Val Ala
            20                  25                  30

Ile Ala Lys Ala Ala Gly Phe Ala Ile Thr Glu Ala Glu Val Lys Ala
        35                  40                  45

Tyr Gln Thr Arg Asn Leu Ser Asp Glu Glu Leu Asp Glu Val Ala Gly
    50                  55                  60
```

```
Gly Ala Pro Cys Arg Pro Phe Thr Asp Pro Ile Tyr Cys Trp Arg Lys
65                  70                  75                  80

Gly Glu Gln Thr Ile Ile Gly Arg Gly Arg Ser Cys Leu Tyr Pro Glu
                85                  90                  95

<210> SEQ ID NO 57
<211> LENGTH: 83
<212> TYPE: PRT
<213> ORGANISM: Artificial Sequence
<220> FEATURE:
<223> OTHER INFORMATION: ProcA 2.6 SYNTHETIC LEADER POLYPEPTIDE SEQUENCE

<400> SEQUENCE: 57

Met Ser Glu Glu Gln Leu Lys Ala Phe Ile Ala Lys Val Gln Ala Asp
1               5                   10                  15

Thr Ser Leu Gln Glu Gln Leu Lys Ala Glu Gly Ala Asp Val Val Ala
            20                  25                  30

Ile Ala Lys Ala Ala Gly Phe Ala Ile Ser Thr Glu Asp Leu Asn Asn
        35                  40                  45

His Arg Gln Asn Leu Ser Asp Asp Glu Leu Glu Gly Val Ala Gly Gly
    50                  55                  60

Gly Ile Cys Val Tyr Val Asn Cys Val Leu Ser Ile Arg Glu Thr Pro
65                  70                  75                  80

Ser Val Ile

<210> SEQ ID NO 58
<211> LENGTH: 79
<212> TYPE: PRT
<213> ORGANISM: Artificial Sequence
<220> FEATURE:
<223> OTHER INFORMATION: ProcA 2.7 SYNTHETIC LEADER POLYPEPTIDE SEQUENCE

<400> SEQUENCE: 58

Met Ser Glu Glu Gln Leu Lys Ala Phe Ile Ala Lys Val Gln Ala Asp
1               5                   10                  15

Thr Ser Leu Gln Glu Gln Leu Lys Ala Glu Gly Ala Asp Val Val Ala
            20                  25                  30

Ile Ala Lys Ala Ala Gly Phe Ser Ile Ala Thr Glu Asp Leu Lys Thr
        35                  40                  45

His Arg Gln Thr Leu Ser Asp Asp Asp Leu Glu Gly Val Ala Gly Gly
    50                  55                  60

Ala Gly Cys Tyr Pro Ile Cys Asp Trp Thr Ser Pro Thr Arg Ser
65                  70                  75

<210> SEQ ID NO 59
<211> LENGTH: 83
<212> TYPE: PRT
<213> ORGANISM: Artificial Sequence
<220> FEATURE:
<223> OTHER INFORMATION: ProcA 2.8 SYNTHETIC LEADER POLYPEPTIDE SEQUENCE

<400> SEQUENCE: 59

Met Ser Glu Glu Gln Leu Lys Ala Phe Leu Thr Lys Val Gln Ala Asp
1               5                   10                  15

Thr Ser Leu Gln Glu Gln Leu Lys Ile Glu Gly Ala Asp Val Val Ala
            20                  25                  30

Ile Ala Lys Ala Ala Gly Phe Ser Ile Thr Thr Glu Asp Leu Asn Ser
        35                  40                  45

His Arg Gln Asn Leu Ser Asp Asp Glu Leu Glu Gly Val Ala Gly Gly
    50                  55                  60
```

```
Ala Ala Cys His Asn His Ala Pro Ser Met Pro Pro Ser Tyr Trp Glu
 65                  70                  75                  80

Gly Glu Cys

<210> SEQ ID NO 60
<211> LENGTH: 83
<212> TYPE: PRT
<213> ORGANISM: Artificial Sequence
<220> FEATURE:
<223> OTHER INFORMATION: ProcA 2.9 SYNTHETIC LEADER POLYPEPTIDE SEQUENCE

<400> SEQUENCE: 60

Met Ser Glu Glu Gln Leu Lys Ala Phe Ile Ala Lys Val Gln Ala Asp
1               5                  10                  15

Pro Ser Leu Gln Glu Gln Leu Lys Ala Glu Gly Ala Asp Val Val Ala
            20                  25                  30

Ile Ala Lys Ala Ala Gly Phe Thr Ile Thr Thr Glu Asp Leu Lys Thr
        35                  40                  45

Ala Arg Gln Thr Leu Ser Asp Asp Leu Glu Gly Val Ala Gly Gly
 50                  55                  60

Tyr Glu Asp Gly Asp Tyr Thr Lys Ser Ile Ser Ile Val Ala Cys
 65                  70                  75                  80

Cys Arg Phe

<210> SEQ ID NO 61
<211> LENGTH: 85
<212> TYPE: PRT
<213> ORGANISM: Artificial Sequence
<220> FEATURE:
<223> OTHER INFORMATION: ProcA 2.10 SYNTHETIC LEADER POLYPEPTIDE
      SEQUENCE

<400> SEQUENCE: 61

Met Ser Glu Glu Gln Leu Lys Ala Phe Ile Ala Lys Val Gln Ala Asp
1               5                  10                  15

Ser Ser Leu Gln Glu Gln Leu Lys Ala Glu Gly Ala Asp Pro Val Ser
            20                  25                  30

Ile Ala Lys Ala Ala Gly Phe Thr Ile Thr Thr Glu Asp Leu Asn Ser
        35                  40                  45

His Arg Gln Asn Leu Ser Asp Glu Glu Leu Glu Gly Ala Ala Gly Gly
 50                  55                  60

Ala Gly Gly Thr Ile Pro Ser Leu Met Thr Gly Cys Gly Trp Leu Thr
 65                  70                  75                  80

Gly Leu Cys Val Arg
                85

<210> SEQ ID NO 62
<211> LENGTH: 84
<212> TYPE: PRT
<213> ORGANISM: Artificial Sequence
<220> FEATURE:
<223> OTHER INFORMATION: ProcA 2.11 SYNTHETIC LEADER POLYPEPTIDE
      SEQUENCE

<400> SEQUENCE: 62

Met Ser Glu Glu Gln Leu Lys Ala Phe Ile Ala Lys Val Gln Ala Asp
1               5                  10                  15

Thr Ser Leu Gln Glu Gln Leu Lys Ala Glu Gly Ala Asp Val Val Ala
            20                  25                  30
```

-continued

Ile Ala Lys Ala Ala Gly Phe Ala Ile Thr Lys Glu Asp Leu Asn Ser
          35                  40                  45

His Arg Gln Thr Leu Ser Glu Asp Glu Leu Glu Ser Val Ala Gly Gly
 50                  55                  60

Gly Arg Ile Asp Thr Cys Pro Ala Gly Gly Thr Ser Glu Gln Thr
65                  70                  75                  80

Gly Thr Cys Cys

<210> SEQ ID NO 63
<211> LENGTH: 87
<212> TYPE: PRT
<213> ORGANISM: Artificial Sequence
<220> FEATURE:
<223> OTHER INFORMATION: ProcA 3.1 SYNTHETIC LEADER POLYPEPTIDE
    SEQUENCE

<400> SEQUENCE: 63

Met Ser Glu Glu Gln Leu Lys Ala Phe Ile Ala Lys Val Gln Ala Asp
1               5                   10                  15

Ala Ser Leu Gln Glu Gln Leu Arg Thr Glu Gly Ala Asp Val Val Ala
                 20                  25                  30

Ile Ala Lys Ala Ala Gly Phe Ser Ile Thr Thr Glu Asp Leu Asn Ser
          35                  40                  45

His Arg Gln Asn Leu Ser Asp Asp Glu Leu Glu Gly Val Ala Gly Gly
 50                  55                  60

Gly Gly Lys Met Thr Val Arg Gly Arg Asp Met Ser Cys Gly Cys Gln
65                  70                  75                  80

Asp Tyr Trp Glu Asp Asp Tyr
                85

<210> SEQ ID NO 64
<211> LENGTH: 91
<212> TYPE: PRT
<213> ORGANISM: Artificial Sequence
<220> FEATURE:
<223> OTHER INFORMATION: ProcA 3.2 SYNTHETIC LEADER POLYPEPTIDE SEQUENCE

<400> SEQUENCE: 64

Met Ser Glu Glu Gln Leu Lys Ala Phe Ile Ala Lys Val Gln Ala Asp
1               5                   10                  15

Ala Ser Leu Gln Glu Gln Leu Arg Thr Glu Gly Ala Asp Val Val Ala
                 20                  25                  30

Ile Ala Lys Ala Ala Gly Phe Ser Ile Thr Thr Glu Asp Leu Asn Ser
          35                  40                  45

His Arg Gln Asn Leu Ser Asp Asp Glu Leu Glu Gly Val Ala Gly Gly
 50                  55                  60

Gly Gly Cys Asp Gly Ile Arg Ile Thr Asp Lys Gln Thr Val Ala Asp
65                  70                  75                  80

Asn Thr Ile Val Pro Cys Ser Cys Phe His Gln
                85                  90

<210> SEQ ID NO 65
<211> LENGTH: 87
<212> TYPE: PRT
<213> ORGANISM: Artificial Sequence
<220> FEATURE:
<223> OTHER INFORMATION: ProcA 3.3 SYNTHETIC LEADER POLYPEPTIDE SEQUENCE

<400> SEQUENCE: 65

Met Ser Glu Glu Gln Leu Lys Ala Phe Ile Ala Lys Val Gln Gly Asp

```
                1               5                   10                  15
Ser Ser Leu Gln Glu Gln Leu Lys Ala Glu Gly Ala Asp Val Val Ala
                20                  25                  30

Ile Ala Lys Ala Ala Gly Phe Thr Ile Lys Gln Gln Asp Leu Asn Ala
                35                  40                  45

Ala Ala Ser Glu Leu Ser Asp Glu Glu Leu Glu Ala Ala Ser Gly Gly
                50                  55                  60

Gly Asp Thr Gly Ile Gln Ala Val Leu His Thr Ala Gly Cys Tyr Gly
65                  70                  75                  80

Gly Thr Lys Met Cys Arg Ala
                85

<210> SEQ ID NO 66
<211> LENGTH: 81
<212> TYPE: PRT
<213> ORGANISM: Artificial Sequence
<220> FEATURE:
<223> OTHER INFORMATION: ProcA 3.4 SYNTHETIC LEADER POLYPEPTIDE SEQUENCE

<400> SEQUENCE: 66

Met Ser Glu Glu Gln Leu Lys Ala Phe Ile Ala Lys Val Gln Gly Asp
1               5                   10                  15

Thr Ser Leu Gln Glu Gln Leu Lys Ala Glu Gly Ala Asp Val Val Ala
                20                  25                  30

Ile Ala Lys Ala Ala Gly Phe Ser Ile Thr Thr Glu Asp Leu Asn Thr
                35                  40                  45

His Arg Gln Thr Leu Ser Asp Arg Glu Leu Glu Gly Val Ala Gly Gly
                50                  55                  60

Thr Thr Ala Phe Thr Gly Val Asp Thr Glu Ser Ile Ala Phe Cys Cys
65                  70                  75                  80

Ser

<210> SEQ ID NO 67
<211> LENGTH: 87
<212> TYPE: PRT
<213> ORGANISM: Artificial Sequence
<220> FEATURE:
<223> OTHER INFORMATION: ProcA 3.5 SYNTHETIC LEADER POLYPEPTIDE SEQUENCE

<400> SEQUENCE: 67

Met Ser Glu Glu Gln Leu Lys Ala Phe Leu Glu Lys Val Lys Ala Asp
1               5                   10                  15

Thr Ser Leu Gln Glu Lys Leu Lys Ala Ala Asp Ser Asp Ala Val
                20                  25                  30

Leu Val Ile Ala Lys Asp Ala Gly Phe Ser Ile Ser Ala Asp Asp Leu
                35                  40                  45

Lys Asn Ala Gln Ser Glu Ile Ser Glu Glu Leu Glu Ser Val Ala
                50                  55                  60

Gly Gly Ala Gly Val Thr Glu Ala Thr Ile Asp Ala Gly Gly Gly Cys
65                  70                  75                  80

Thr Phe Asn Pro Cys Cys Arg
                85

<210> SEQ ID NO 68
<211> LENGTH: 101
<212> TYPE: PRT
<213> ORGANISM: Artificial Sequence
<220> FEATURE:
<223> OTHER INFORMATION: ProcA 4.1 SYNTHETIC LEADER POLYPEPTIDE SEQUENCE
```

<400> SEQUENCE: 68

Met Ser Glu Glu Gln Leu Lys Ala Leu Ile Ala Lys Val Gln Ala Asp
1               5                   10                  15

Thr Ser Leu Gln Glu Gln Leu Lys Ala Glu Gly Ala Asp Val Val Ala
            20                  25                  30

Ile Ala Lys Ala Ala Gly Phe Ser Ile Thr Thr Glu Asp Leu Lys Glu
        35                  40                  45

His Arg Gln Thr Leu Ser Val Gly Arg Gln Thr Leu Ser Glu Ser Glu
    50                  55                  60

Leu Glu Gly Leu Ala Gly Gly Gly Gly Ala Arg Thr Lys Thr Ala
65                  70                  75                  80

Asn Val Pro Ser Asp Leu Pro Val Arg Ala Pro Ala Met Ser Thr Phe
                85                  90                  95

Ala Glu Asn Gln Thr
            100

<210> SEQ ID NO 69
<211> LENGTH: 80
<212> TYPE: PRT
<213> ORGANISM: Artificial Sequence
<220> FEATURE:
<223> OTHER INFORMATION: ProcA 4.2 SYNTHETIC LEADER POLYPEPTIDE SEQUENCE

<400> SEQUENCE: 69

Met Ser Glu Glu Gln Leu Lys Ala Phe Ile Ala Lys Val Gln Ala Asp
1               5                   10                  15

Thr Ser Leu Gln Glu Gln Leu Lys Ala Glu Gly Ala Asp Pro Val Ala
            20                  25                  30

Ile Ala Lys Ala Ala Gly Phe Ser Ile Thr Thr Glu Asp Leu Lys Glu
        35                  40                  45

His Arg Gln Ala Leu Ser Asp Asp Asp Leu Glu Gly Val Ala Gly Gly
    50                  55                  60

Thr Ile Val Thr Val Thr Gly Ala Leu Ile Ser Ile Ala Ala Glu Cys
65                  70                  75                  80

<210> SEQ ID NO 70
<211> LENGTH: 77
<212> TYPE: PRT
<213> ORGANISM: Artificial Sequence
<220> FEATURE:
<223> OTHER INFORMATION: ProcA 4.3 SYNTHETIC LEADER POLYPEPTIDE SEQUENCE

<400> SEQUENCE: 70

Met Ser Glu Glu Gln Leu Lys Ala Phe Ile Ala Lys Val Gln Ala Asp
1               5                   10                  15

Thr Ser Leu Gln Glu Gln Leu Lys Ala Glu Gly Ala Asp Val Val Ala
            20                  25                  30

Ile Ala Lys Ala Ala Gly Phe Thr Ile Thr Thr Glu Asp Leu Asn Ser
        35                  40                  45

His Arg Gln Asn Leu Thr Asp Asp Glu Leu Glu Gly Val Ala Gly Gly
    50                  55                  60

Thr Ala Ser Gly Gly Cys Asp Thr Ser Met Phe Cys Tyr
65                  70                  75

<210> SEQ ID NO 71
<211> LENGTH: 85
<212> TYPE: PRT
<213> ORGANISM: Artificial Sequence
<220> FEATURE:
<223> OTHER INFORMATION: ProcA 4.4 SYNTHETIC LEADER POLYPEPTIDE SEQUENCE

<400> SEQUENCE: 71

```
Met Ser Glu Glu Gln Leu Lys Ala Phe Leu Glu Lys Val Lys Gly Asp
1               5                   10                  15

Thr Ser Leu Gln Glu Lys Leu Gln Ala Ala Asp Ser Asp Ala Val
            20                  25                  30

Leu Ala Ile Ala Lys Glu Ala Gly Phe Met Ile Ser Ala Asp Glu Leu
            35                  40                  45

Lys Lys Ala Gln Ser Glu Ile Ser Glu Glu Leu Glu Ser Ala Ala
        50                  55                  60

Gly Gly Arg Leu Lys Ser Gly Cys His Cys Gly Thr Val Ile Arg Ser
65                  70                  75                  80

Tyr Ser Lys Tyr Cys
                85
```

<210> SEQ ID NO 72
<211> LENGTH: 92
<212> TYPE: PRT
<213> ORGANISM: Artificial Sequence
<220> FEATURE:
<223> OTHER INFORMATION: ProcA S.1 SYNTHETIC LEADER POLYPEPTIDE SEQUENCE

<400> SEQUENCE: 72

```
Met Ser Glu Glu Gln Leu Lys Ala Phe Leu Glu Lys Val Lys Ala Asp
1               5                   10                  15

Thr Ser Leu Gln Glu Lys Leu Lys Ala Ala Asp Ser Asp Ala Val
            20                  25                  30

Leu Val Ile Ala Lys Asp Ala Gly Phe Ser Ile Ser Ala Asp Leu
            35                  40                  45

Lys Asn Ala Gln Ser Glu Ile Ser Glu Glu Leu Glu Ser Val Ala
        50                  55                  60

Gly Gly Ala Gln Ser Ala Gly Cys Gly Ile Cys Glu Cys Asp Asn
65                  70                  75                  80

Arg Gln Ser Thr Ser Cys His Tyr Pro Ser His Gly
                85                  90
```

<210> SEQ ID NO 73
<211> LENGTH: 98
<212> TYPE: PRT
<213> ORGANISM: Artificial Sequence
<220> FEATURE:
<223> OTHER INFORMATION: ProcA S.2 SYNTHETIC LEADER POLYPEPTIDE SEQUENCE

<400> SEQUENCE: 73

```
Met Ser Glu Glu Gln Leu Lys Ala Phe Leu Glu Lys Val Lys Ala Asp
1               5                   10                  15

Thr Ser Leu Gln Glu Lys Leu Lys Ala Ala Gly Ser Asp Ala Val
            20                  25                  30

Leu Ala Ile Ala Lys Ala Ala Gly Leu Met Ile Ser Ala Asp Leu
            35                  40                  45

Thr Lys Ala Gln Ser Glu Ile Ser Asp Ala Glu Leu Glu Asp Ala Ala
        50                  55                  60

Gly Gly Gly Ala Gln Gly Pro Ala Cys Cys Ala Ala Met Glu Ser Ser
65                  70                  75                  80

Asp Thr Arg Cys Gly Trp Val Ser Trp Val Leu Ser Glu Val Val Pro
                85                  90                  95
```

Pro Gln

<210> SEQ ID NO 74
<211> LENGTH: 67
<212> TYPE: PRT
<213> ORGANISM: Artificial Sequence
<220> FEATURE:
<223> OTHER INFORMATION: ProcA T.1 SYNTHETIC LEADER POLYPEPTIDE SEQUENCE

<400> SEQUENCE: 74

```
Met Gln Glu Gln Leu Lys Ala Glu Gly Ala Asp Val Ile Ala Ile Ala
1               5                   10                  15

Lys Ala Ala Gly Phe Ser Ile Thr Ile Glu Asp Leu Lys Glu His Arg
            20                  25                  30

Lys Thr Leu Ser Asp Ala Glu Leu Glu Gly Leu Ala Gly Gly Ala Phe
        35                  40                  45

Asn His Asp Trp Gly Gln Thr Thr Arg Asn Tyr Lys Cys Glu Thr Ser
    50                  55                  60

Tyr Cys Cys
65
```

<210> SEQ ID NO 75
<211> LENGTH: 19
<212> TYPE: PRT
<213> ORGANISM: Artificial Sequence
<220> FEATURE:
<223> OTHER INFORMATION: SYNTHETIC LIBRARY 1 ProA 2.8 LEADER POLYPEPTIDE
      SEQUENCE
<220> FEATURE:
<221> NAME/KEY: misc_feature
<222> LOCATION: (4)..(8)
<223> OTHER INFORMATION: Xaa can be any naturally occurring amino acid
<220> FEATURE:
<221> NAME/KEY: misc_feature
<222> LOCATION: (14)..(18)
<223> OTHER INFORMATION: Xaa can be any naturally occurring amino acid

<400> SEQUENCE: 75

```
Ala Ala Cys Xaa Xaa Xaa Xaa Xaa Ser Met Pro Pro Ser Xaa Xaa Xaa
1               5                   10                  15

Xaa Xaa Cys
```

<210> SEQ ID NO 76
<211> LENGTH: 20
<212> TYPE: PRT
<213> ORGANISM: Artificial Sequence
<220> FEATURE:
<223> OTHER INFORMATION: SYNTHETIC LIBRARY 2 ProA 2.8 LEADER POLYPEPTIDE
      SEQUENCE
<220> FEATURE:
<221> NAME/KEY: misc_feature
<222> LOCATION: (7)..(18)
<223> OTHER INFORMATION: Xaa can be any naturally occurring amino acid

<400> SEQUENCE: 76

```
Tyr His His Tyr Asn Ser Xaa Xaa Xaa Xaa Xaa Xaa Xaa Xaa Xaa Xaa
1               5                   10                  15

Xaa Xaa Cys Tyr
            20
```

<210> SEQ ID NO 77
<211> LENGTH: 64
<212> TYPE: PRT
<213> ORGANISM: Artificial Sequence
<220> FEATURE:
<223> OTHER INFORMATION: SYNTHETIC ProcA 2.8 LEADER POLYPEPTIDE SEQUENCE

<400> SEQUENCE: 77

Met Ser Glu Glu Gln Leu Lys Ala Phe Leu Thr Lys Val Gln Ala Asp
1               5                   10                  15

Thr Ser Leu Gln Glu Gln Leu Lys Ile Glu Gly Ala Asp Val Val Ala
            20                  25                  30

Ile Ala Lys Ala Ala Gly Phe Ser Ile Thr Thr Glu Asp Leu Asn Ser
        35                  40                  45

His Arg Gln Asn Leu Ser Asp Asp Glu Leu Glu Gly Val Ala Gly Gly
    50                  55                  60

<210> SEQ ID NO 78
<211> LENGTH: 19
<212> TYPE: PRT
<213> ORGANISM: Artificial Sequence
<220> FEATURE:
<223> OTHER INFORMATION: SYNTHETIC 2.8-1 POLYPEPTIDE SEQUENCE

<400> SEQUENCE: 78

Ala Ala Cys Phe Asn Val His Ile Ser Met Pro Pro Ser His Asn Asn
1               5                   10                  15

Val His Cys

<210> SEQ ID NO 79
<211> LENGTH: 19
<212> TYPE: PRT
<213> ORGANISM: Artificial Sequence
<220> FEATURE:
<223> OTHER INFORMATION: SYNTHETIC 2.8-10 POLYPEPTIDE SEQUENCE

<400> SEQUENCE: 79

Ala Ala Cys Val Asn His Leu Leu Ser Met Pro Pro Ser Leu Asn Asp
1               5                   10                  15

Leu Asn Cys

<210> SEQ ID NO 80
<211> LENGTH: 19
<212> TYPE: PRT
<213> ORGANISM: Artificial Sequence
<220> FEATURE:
<223> OTHER INFORMATION: SYNTHETIC 2.8-11 POLYPEPTIDE SEQUENCE

<400> SEQUENCE: 80

Ala Ala Cys Asp Val Asn Leu His Ser Met Pro Pro Ser Leu Asp Phe
1               5                   10                  15

Phe Val Cys

<210> SEQ ID NO 81
<211> LENGTH: 19
<212> TYPE: PRT
<213> ORGANISM: Artificial Sequence
<220> FEATURE:
<223> OTHER INFORMATION: SYNTHETIC 2.8-15 POLYPEPTIDE SEQUENCE

<400> SEQUENCE: 81

Ala Ala Cys Val Phe His Phe Asp Ser Met Pro Pro Ser Tyr Leu Asp
1               5                   10                  15

Asp Asp Cys

<210> SEQ ID NO 82
<211> LENGTH: 19
<212> TYPE: PRT

```
<213> ORGANISM: Artificial Sequence
<220> FEATURE:
<223> OTHER INFORMATION: SYNTHETIC 2.8-3 POLYPEPTIDE SEQUENCE

<400> SEQUENCE: 82

Ala Ala Cys Asn Ile Asp Phe Leu Ser Met Pro Pro Ser Ile His His
1               5                   10                  15

Ile Leu Cys

<210> SEQ ID NO 83
<211> LENGTH: 19
<212> TYPE: PRT
<213> ORGANISM: Artificial Sequence
<220> FEATURE:
<223> OTHER INFORMATION: SYNTHETIC 2.8-5 POLYPEPTIDE SEQUENCE

<400> SEQUENCE: 83

Ala Ala Cys Asn Ile Tyr Tyr Ile Ser Met Pro Pro Ser His His Phe
1               5                   10                  15

Val Tyr Cys

<210> SEQ ID NO 84
<211> LENGTH: 19
<212> TYPE: PRT
<213> ORGANISM: Artificial Sequence
<220> FEATURE:
<223> OTHER INFORMATION: SYNTHETIC HIT 3-3 POLYPEPTIDE SEQUENCE

<400> SEQUENCE: 84

Ala Ala Cys Leu His Phe Phe Leu Ser Met Pro Pro Ser His Val Leu
1               5                   10                  15

Asp Ile Cys

<210> SEQ ID NO 85
<211> LENGTH: 20
<212> TYPE: PRT
<213> ORGANISM: Artificial Sequence
<220> FEATURE:
<223> OTHER INFORMATION: SYNTHETIC 2C10 POLYPEPTIDE SEQUENCE

<400> SEQUENCE: 85

Tyr His His Tyr Asn Cys Tyr Asn Phe Asn Leu Phe Asn Asn Tyr Asn
1               5                   10                  15

Asn Asn Ser Tyr
            20

<210> SEQ ID NO 86
<211> LENGTH: 20
<212> TYPE: PRT
<213> ORGANISM: Artificial Sequence
<220> FEATURE:
<223> OTHER INFORMATION: SYNTHETIC 2C10S POLYPEPTIDE SEQUENCE

<400> SEQUENCE: 86

Tyr His His Tyr Asn Ser Tyr Asn Phe Asn Leu Phe Asn Asn Tyr Asn
1               5                   10                  15

Asn Asn Cys Tyr
            20

<210> SEQ ID NO 87
<211> LENGTH: 20
<212> TYPE: PRT
<213> ORGANISM: Artificial Sequence
<220> FEATURE:
```

```
<223> OTHER INFORMATION: SYNTHETIC 2C10-3 POLYPEPTIDE SEQUENCE

<400> SEQUENCE: 87

Tyr His His Tyr Asn Ser Asp Val Leu Leu Asp Leu Lys Lys Asn Asp
1               5                   10                  15

Leu Glu Cys Tyr
            20

<210> SEQ ID NO 88
<211> LENGTH: 20
<212> TYPE: PRT
<213> ORGANISM: Artificial Sequence
<220> FEATURE:
<223> OTHER INFORMATION: SYNTHETIC 2C10-10 POLYPEPTIDE SEQUENCE

<400> SEQUENCE: 88

Tyr His His Tyr Asn Ser Val Ile Asn His Leu Asn Asp Leu Gln Glu
1               5                   10                  15

Lys Leu Cys Tyr
            20

<210> SEQ ID NO 89
<211> LENGTH: 20
<212> TYPE: PRT
<213> ORGANISM: Artificial Sequence
<220> FEATURE:
<223> OTHER INFORMATION: SYNTHETIC 2C10-11 POLYPEPTIDE SEQUENCE

<400> SEQUENCE: 89

Tyr His His Tyr Asn Ser Gln Gln Val Val Ile Ile Gln Asp Asn Gln
1               5                   10                  15

Val Asp Cys Tyr
            20

<210> SEQ ID NO 90
<211> LENGTH: 20
<212> TYPE: PRT
<213> ORGANISM: Artificial Sequence
<220> FEATURE:
<223> OTHER INFORMATION: SYNTHETIC 2C10-14 POLYPEPTIDE SEQUENCE

<400> SEQUENCE: 90

Tyr His His Tyr Asn Ser Met Ile Lys His Lys Glu His Asp His Met
1               5                   10                  15

Ile Ile Cys Tyr
            20

<210> SEQ ID NO 91
<211> LENGTH: 45
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 91
ttggtctcat ccacaattcg aaaaactgca ggctagtggt ggtgg            45

<210> SEQ ID NO 92
<211> LENGTH: 53
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 92
```
cgaattgtgg atgagaccaa ttggatctac cttcaatcgt cgagctattg tcc    53

<210> SEQ ID NO 93
<211> LENGTH: 43
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 93
ttatatttcc agggtagcca gcaggaactg acaactatat gcg    43

<210> SEQ ID NO 94
<211> LENGTH: 45
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 94
gcagcggttt ctttaccaga ctcgatcaca acattcacc ttccc    45

<210> SEQ ID NO 95
<211> LENGTH: 44
<212> TYPE: DNA
<213> ORGANISM: Artificial Sequence
<220> FEATURE:
<223> OTHER INFORMATION: SYNTHETIC OLIGONULCEOTIDE

<400> SEQUENCE: 95
tggtgccgcg cggcagccat caggaactga caactatatg cgag    44

<210> SEQ ID NO 96
<211> LENGTH: 43
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 96
tgtcgacgga gctcgaattc ttagcactgg cttgtacact ttg    43

<210> SEQ ID NO 97
<211> LENGTH: 47
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 97
ctttaagaag gagatatacc atgaaggaac aaaactcctt caacttg    47

<210> SEQ ID NO 98
<211> LENGTH: 44
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 98
ggtggtggtg gtgctcgagt tcagtgatga tgatggtggt ggtg    44

<210> SEQ ID NO 99
<211> LENGTH: 51
<212> TYPE: DNA

<213> ORGANISM: Artificial Sequence
<220> FEATURE:
<223> OTHER INFORMATION: SYNTHETIC OLIGONUCLEOTIDE

<400> SEQUENCE: 99
atttcacacg agctcggtac ccgggccaga cgtaatctaa taaggaggta c        51

<210> SEQ ID NO 100
<211> LENGTH: 52
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 100
tcttctctca tccgccaaaa cagccttaat caacatatgg cattaagact cc        52

<210> SEQ ID NO 101
<211> LENGTH: 55
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 101
caatttcaca cgagctcagg agatatacca tggaaagtcc atcatcttgg aaaac        55

<210> SEQ ID NO 102
<211> LENGTH: 38
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 102
tccgccaaaa cagccttatt cagtaggcca gagaccag        38

<210> SEQ ID NO 103
<211> LENGTH: 55
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 103
agctcggtac ccggggatcc caggagatat accatgaaaa ctcctctaac aagtg        55

<210> SEQ ID NO 104
<211> LENGTH: 50
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 104
tctcatccgc caaaacagcc aagcttttat ctgtcatgaa ttctcaactc        50

<210> SEQ ID NO 105
<211> LENGTH: 27
<212> TYPE: PRT
<213> ORGANISM: Artificial Sequence
<220> FEATURE:
<223> OTHER INFORMATION: SYNTHETIC LACTINCIN 481 POLYPEPTIDE SEQUENCE
<220> FEATURE:
<221> NAME/KEY: MISC_FEATURE
<222> LOCATION: (9)..(9)
<223> OTHER INFORMATION: X is Abu.

```
<220> FEATURE:
<221> NAME/KEY: MISC_FEATURE
<222> LOCATION: (24)..(24)
<223> OTHER INFORMATION: X is dehydrobutyrine (Dhb).

<400> SEQUENCE: 105

Lys Gly Gly Ser Gly Val Ile His Xaa Ile Ala His Glu Ala Asn Met
1               5                   10                  15

Asn Ala Trp Gln Phe Val Phe Xaa Ala Ala Ser
            20                  25

<210> SEQ ID NO 106
<211> LENGTH: 19
<212> TYPE: PRT
<213> ORGANISM: Artificial Sequence
<220> FEATURE:
<223> OTHER INFORMATION: SYNTHETIC Cinnamycin POLYPEPTIDE SEQUENCE
<220> FEATURE:
<221> NAME/KEY: MISC_FEATURE
<222> LOCATION: (2)..(2)
<223> OTHER INFORMATION: X is Abu.
<220> FEATURE:
<221> NAME/KEY: MISC_FEATURE
<222> LOCATION: (9)..(9)
<223> OTHER INFORMATION: X is Abu.

<400> SEQUENCE: 106

Lys Xaa Asn Gly Asp Ala Val Phe Xaa Phe Pro Gly Phe Ala Ala Ala
1               5                   10                  15

Gln Arg Ala

<210> SEQ ID NO 107
<211> LENGTH: 26
<212> TYPE: PRT
<213> ORGANISM: Artificial Sequence
<220> FEATURE:
<223> OTHER INFORMATION: SYNTHETIC Haloduracin alpha SYNTHETIC
      POLYPEPTIDE
<220> FEATURE:
<221> NAME/KEY: MISC_FEATURE
<222> LOCATION: (16)..(16)
<223> OTHER INFORMATION: X is Abu.
<220> FEATURE:
<221> NAME/KEY: MISC_FEATURE
<222> LOCATION: (18)..(18)
<223> OTHER INFORMATION: X is Abu.

<400> SEQUENCE: 107

Ala Ile Asn Tyr Trp Ala Arg Leu Gly Asn Lys Gly Ala Tyr Ala Xaa
1               5                   10                  15

Leu Xaa Val Glu Ala Met Pro Ser Ala Asn
            20                  25
```

BIOSYNTHESIS AND ENGINEERING OF LANTHIPEPTIDES

CROSS-REFERENCE TO RELATED APPLICATIONS

The present application is the U.S. National Stage of International Patent Application No. PCT/US15/52724, filed Sep. 28, 2015, which claims benefit of priority under 35 U.S.C. 119 to U.S. provisional patent application Ser. No. 62/056,216, filed Sep. 26, 2014, and entitled "BIOSYNTHESIS AND ENGINEERING OF LANTHIPEPTIDES," the contents of which are herein incorporated by reference in its entirety.

STATEMENT OF GOVERNMENT INTEREST

This invention was made with government support under GM-58822 awarded by the National Institutes of Health. The government has certain rights in the invention.

SEQUENCE LISTING

The instant application contains a Sequence Listing that has been submitted in ASCII format via EFS-Web and is hereby incorporated by reference in its entirety. The ASCII copy, created on Sep. 25, 2015, is named UIU01-018-PCT_ST25.txt, and is 52,604 bytes in size.

FIELD

The present disclosure relates to molecular reagents and genetic methods of synthesizing engineered lanthipeptides in vivo from recombinant organisms.

BACKGROUND

Natural products produced by living organisms such as animals, plants, and microbes often have valuable biological activities and thus, they have been employed in a variety of areas including medicine, cosmetics, and the food industry. (Clardy, J., Fischbach, M. A., and Walsh, C. T. "New antibiotics from bacterial natural products," *Nat. Biotechnol.* 24:1541-1550 (2006).) The isolation and discovery of pharmaceutically valuable compounds for the use of humans began during the 1940's with the discovery of antibiotics and peaked in the period of 1970-1980. (Koehn, F. E., and Carter, G. T. "The evolving role of natural products in drug discovery," *Nat. Rev. Drug Discov.* 4:206-220 (2005); Fischbach, M. A., and Walsh, C. T. "Antibiotics for Emerging Pathogens," *Science* 325:1089-1093 (2009).) The lack of new approaches to isolate new natural products in addition to a long and expensive development process has caused pharmaceutical companies to retract from this field in recent years. (Koehn, F. E., and Carter, G. T. "The evolving role of natural products in drug discovery," *Nat. Rev. Drug Discov.* 4:206-220 (2005).)

A new urgency for the discovery of new antibiotics that operate with different mechanisms of action compared to current antibiotics emerged as antibiotic-resistant infectious bacterial strains, such as methicillin-resistant Staphyloccocus aureus (MRSA) and vancomycin-resistant Enterococci (VRE), have started to appear in clinical settings. ((Fischbach, M. A., and Walsh, C. T. "Antibiotics for Emerging Pathogens," *Science* 325:1089-1093 (2009).) Many studies have demonstrated a clear relationship between exposure time to an antibiotic and the appearance of resistant strains. (Tacconelli, E., De Angelis, G., Cataldo, M. A., Pozzi, E., and Cauda, R. "Does antibiotic exposure increase the risk of methicillin-resistant Staphylococcus aureus (MRSA) isolation? A systematic review and meta-analysis," *J. Antimicrob. Chemother.* 61:26-38 (2008).) Higher usage of an antibiotic leads to development of resistant bacterial strains, requiring the continual discovery of new pharmaceutically available antibiotics. A need therefore exists to create new methodology for discovering new antibiotics and other natural products having therapeutic or diagnostic value.

Lanthipeptide Biosynthesis

Nisin is a polycyclic antibacterial peptide with 34 amino acid residues and five cyclic thioether cross-links of varying sizes. After the precursor peptide NisA is synthesized by the ribosome, the cross-links are installed by sequential actions of the enzymes NisB and NisC on NisA (FIG. 1). Then, the mature lantibiotic is formed through the cleavage of the leader peptide located at the N-terminus of NisA by NisP, a serine protease (FIG. 1). (van der Meer, J. R., Polman, J., Beerthuyzen, M. M., Siezen, R. J., Kuipers, O. P., and de Vos, W. M. "Characterization of the Lactococcus lactis nisin A operon genes nisP, encoding a subtilisin-like serine protease involved in precursor processing, and nisR, encoding a regulatory protein involved in nisin biosynthesis," *J. Bacteria* 175:2578-2588 (1993).) NisB dehydrates threonines and serines in the core region of NisA whereas NisC forms the five thioether cross-links by Michael-type addition of cysteine thiols to the dehydrated Thr/Ser. Nisin specifically binds to the pyrophosphate group of lipid II and forms pores in the cell membrane to kill gram positive bacteria (Hsu, S. T., Breukink, E , Tischenko, E., Lutters, M. A., De Kruijff, B., Kaptein, R., Bonvin, A. M., and Van Nuland, N. A. "The nisin-lipid II complex reveals a pyrophosphate cage that provides a blueprint for novel antibiotics," *Nat. Struct. Mol. Biol.* 11:963-967 (2004)).

Cyclic peptides are promising candidates to use as molecular scaffolds for peptide libraries, which in turn may provide powerful tools for drug design and investigation and disruption of protein-protein interactions. The characteristic thioether crosslinks of lanthipeptides provide stability to different physical conditions (pH, temperature), resistance to proteases, and form scaffolds to selectively and tightly bind to small molecules such as lipid II and phosphotidylethanolamine (PE). (Oman, T. J., Lupoli, T. J., Wang, T. S. A., Kahne, D., Walker, S., and van der Donk, W.A. "Haloduracin α binds the peptidoglycan precursor lipid II with 2:1 stoichiometry," *J. Am. Chem. Soc.* 133:17544 (2011); Makino, A., Baba, T., Fujimoto, K., Iwamoto, K., Yano, Y., Terada, N., Ohno, S., Sato, S. B., Ohta, A., Umeda, M., Matsuzaki, K., and Kobayashi, T. "Cinnamycin (Ro 09-0198) promotes cell binding and toxicity by inducing transbilayer lipid movement," *J. Biol. Chem.* 278:3204-3209 (2003); Hasper, H. E., de Kruijff, B., and Breukink, E "Assembly and stability of nisin-lipid II pores," *Biochemistry* 43:11567-11575 (2004); Knerr, P. J., and van der Donk, W. A. "Discovery, Biosynthesis, and Engineering of Lantipeptides," *Annu. Rev. Biochem.* 81:479-505 (2012).) These crosslinks are necessary for the activity of antimicrobial lanthipeptides, called lantibiotics, as in the absence of these modifications, binding to their target is not observed. Previous studies showed that the solubility, stability, and therapeutic effect of lanthipeptides can be improved by replacement of amino acids at different positions in the sequence with natural and/or unnatural residues. (Knerr, P. J., Oman, T. J., Garcia De Gonzalo, C. V., Lupoli, T. J., Walker, S., and van der Donk, W. A. "Non-proteinogenic Amino Acids in Lacticin 481 Analogues Result in More Potent Inhibition of Peptidoglycan Transglycosylation," *ACS Chem. Biol.* 7:1791-1795 (2012); Field, D., Begley, M., O'Connor, P. M., Daly, K. M., Hugenholtz, F., Cotter, P. D., Hill, C., and Ross, R. P. "Bioengineered Nisin A Derivatives with Enhanced Activity against Both Gram Positive and Gram Negative Pathogens," *PLoS ONE* 7:e46884 (2012).) However, only a few systematic methods for discovery of new, pharmaceutically valuable lanthipeptides are available such as bacterial display, and in vitro non-ribosomal translation of lanthipeptides with designed ring structures. (Hofmann, F. T., Szostak, J. W., and Seebeck, F. P. "In Vitro Selection of Functional Lantipeptides," *J. Am. Chem. Soc.* 134:8038-8041 (2012); Bosma, T., Kuipers, A., Bulten, E., de Vries, L., Rink, R., and Moll, G. N. "Bacterial Display and Screening of Posttranslationally Thioether-Stabilized Peptides," *Appl. Environ. Microb.* 77:6794-6801 (2011).

Phage Display Systems

Phage display is widely used for identification of peptide/protein-binders from large libraries of peptides. (Sachdev S, S. (2001) Engineering M13 for phage display, Biomol. Eng. 18, 57-63 (2001); Bratkovič, T. "Progress in phage display: evolution of the technique and its applications," *Cell. Mol. Life Sci.* 67:749-767 (2010)). However, introduction of post-translational modifications onto the phage-displayed peptides is a fairly new concept. Three approaches can be used to introduce modifications on a phage-displayed peptide. One way to alter the structure of a phage-displayed peptide is chemical modification by reagents that selectively react with the peptide. (Li, K., Chen, Y., Li, S., Nguyen, H. G., Niu, Z., You, S., Mello, C. M., Lu, X., and Wang, Q. "Chemical Modification of M13 Bacteriophage and Its Application in Cancer Cell Imaging," *Bioconjugate Chem.* 21:1369-1377 (2010); Heinis, C., Rutherford, T., Freund, S., and Winter, G. "Phage-encoded combinatorial chemical libraries based on bicyclic peptides," *Nat. Chem. Biol.* 5:502-507 (2009); Ng, S., Jafari, M. R., and Derda, R. "Bacteriophages and Viruses as a Support for Organic Synthesis and Combinatorial Chemistry," *ACS Chem. Biol.* 7:123-138 (2011).) For example, in a recent study peptides containing three cysteine residues separated by several random amino acid residues were fused to the phage pIII protein and reacted with tris-(bromomethyl)benzene to form bicyclic peptide libraries on phage. (Heinis, C., Rutherford, T., Freund, S., and Winter, G. "Phage-encoded combinatorial chemical libraries based on bicyclic peptides," i Nat. Chem. Biol. 5:502-507 (2009).)

Another way to modify phage-displayed peptides is attachment of both the substrate peptide and the modifying enzyme onto the phage surface so that the enzyme catalyzes the formation of the product on phage. This method has been used to engineer enzymes catalyzing desired reactions through directed mutagenesis. (Love, K. R., Swoboda, J. G., Noren, C. J., and Walker, S. "Enabling Glycosyltransferase Evolution: A Facile Substrate-Attachment Strategy for Phage-Display Enzyme Evolution," *ChemBioChem* 7:753-756 (2006); Sunbul, M., Emerson, N., and Yin, J. "Enzyme-Catalyzed Substrate Attachment to Phage Surfaces for the Selection of Catalytic Activities," *ChemBioChem* 12:380-386 (2011).)

Finally, the third method that has been successful to modify the peptide displayed on phage is in vitro modification of the peptide by an enzyme. (Hess, G. T., Cragnolini, J. J., Popp, M. W., Allen, M. A., Dougan, S. K., Spooner, E., Ploegh, H. L., Belcher, A. M., and Guimaraes, C. P. "M13 Bacteriophage Display Framework That Allows Sortase-Mediated Modification of Surface-Accessible Phage Proteins," *Bioconjugate Chem.* 23:1478-1487 (2012).) The drawbacks of these methods include the necessity of reconstitution of the enzyme activity in vitro, and efficient substrate recognition and/or appropriate folding of the enzyme attached to the phage surface.

Previous studies showed that a naturally occurring enzyme in phage infected bacteria can modify peptides fused to a phage protein in vivo, which are then displayed on the newly formed phage. (Edgar, R., McKinstry, M., Hwang, J., Oppenheim, A. B., Fekete, R. A., Giulian, G., Merril, C., Nagashima, K., and Adhya, S. "High-sensitivity bacterial detection using biotin-tagged phage and quantum-dot nanocomplexes," *Proc. Nat. Acad. Sci. USA* 103:4841-4845 (2006).) For example, phage designed to display a specific 15 amino acid long substrate on their pIII protein was biotinylated by the *Escherichia coli* (*E. coli*) enzyme called biotin holoenzyme synthetase (BHS; product of the birA gene) in vivo. (Smelyanski, L., and Gershoni, J. "Site directed biotinylation of filamentous phage structural proteins," *Virol. J.* 8:495 (2011).)

SUMMARY

In a first aspect, a platform for bacterial phage display of a lanthipeptide is provided. The platform includes: a phagemid including a lanthipeptide display system; a helper phage; and a bacterial host organism configured to express one or more lanthipeptide biosynthesis enzymes.

In a second aspect, a phage for displaying a lanthipeptide is provided. The phage is made according to the platform of the first aspect. The phage is configured to infect a bacterial host organism including a Gram-positive bacterium.

In a third aspect, a platform for cell surface display of a lanthipeptide is provided. The platform includes: a lanthipeptide display system; and a yeast host organism configured to express one or more lanthipeptide biosynthesis enzymes.

In a fourth respect, a lanthipeptide display system is provided. The lanthipeptide display system includes a gene chimera encoding a fusion peptide including a lanthipeptide display peptide and a presentation peptide. The presentation peptide anchors the lanthipeptide display peptide on an outer biological surface.

In a fifth aspect, a lanthipeptide library display system is provided. The lanthipeptide library display system includes a lanthipeptide expression library having a plurality of gene chimeras. Each member of the plurality of gene chimeras encodes a fusion peptide including a lanthipeptide display peptide and a presentation peptide. The presentation peptide anchors the lanthipeptide display peptide on an outer biological surface.

In a sixth aspect, a method of identifying a lanthipeptide display peptide expressed in vivo from a biological host organism is provided. The method includes several steps. The first step includes preparing a biological host library, wherein each member of the biological host library expresses a gene chimera encoding a fusion peptide including a lanthipeptide display peptide and a presentation peptide. The presentation peptide anchors the lanthipeptide display peptide on an outer biological surface of the biological host organism. The second step includes sorting the biological host library to form a candidate subset of the biological hosts that express the lanthipeptide display peptide.

In a seventh aspect, a phagemid including a lanthipeptide display system is provided.

These and other features, objects and advantages of the present invention will become better understood from the description that follows. In the description, reference is made to the accompanying drawings, which form a part hereof and in which there is shown by way of illustration, not limitation, aspects of the invention.

BRIEF DESCRIPTION OF THE DRAWINGS

FIG. 4C depicts the molecular structure of nisin (for a shorthand notation, see FIG. 1). Trypsin cleavage sites within nisin are shown in red. When modifications are introduced trypsin does not readily cleave after the designated lysines. Hence, since the leader peptide ends in Arg, and since the last residue of nisin is Lys, treatment of nisin-displaying phage with trypsin, releases the mature nisin (provided it has been posttranslationally modified) as shown in FIG. 4B.

Calculated mass for M−2 H$_2$O+H for peptide 2.8-10: 2468.8−2*18+1=2432.8 Da, Obsrvd: 2432 Da.

Figure 7A:
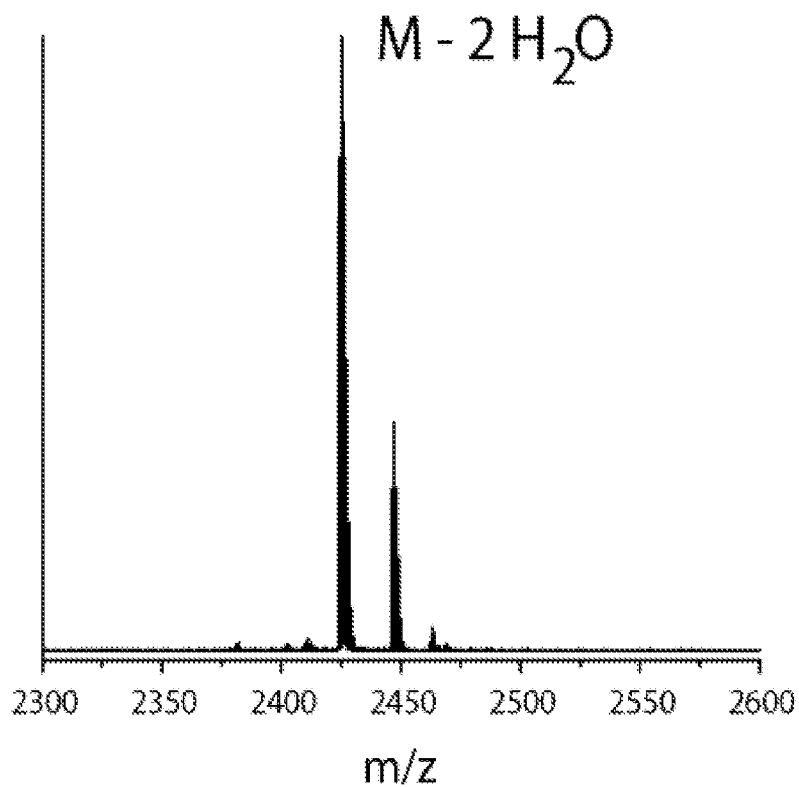
FIG. 7A depicts mass spectrometry analysis of the peptide 2.8-5 modified by ProcM in *E. coli* and treated with GluC. Calculated mass for M−2 H$_2$O+H for peptide 2.8-5: 2460.6−2*18+1=2425.6 Da, Obsrvd: 2424.1 Da.
Figure 7B:
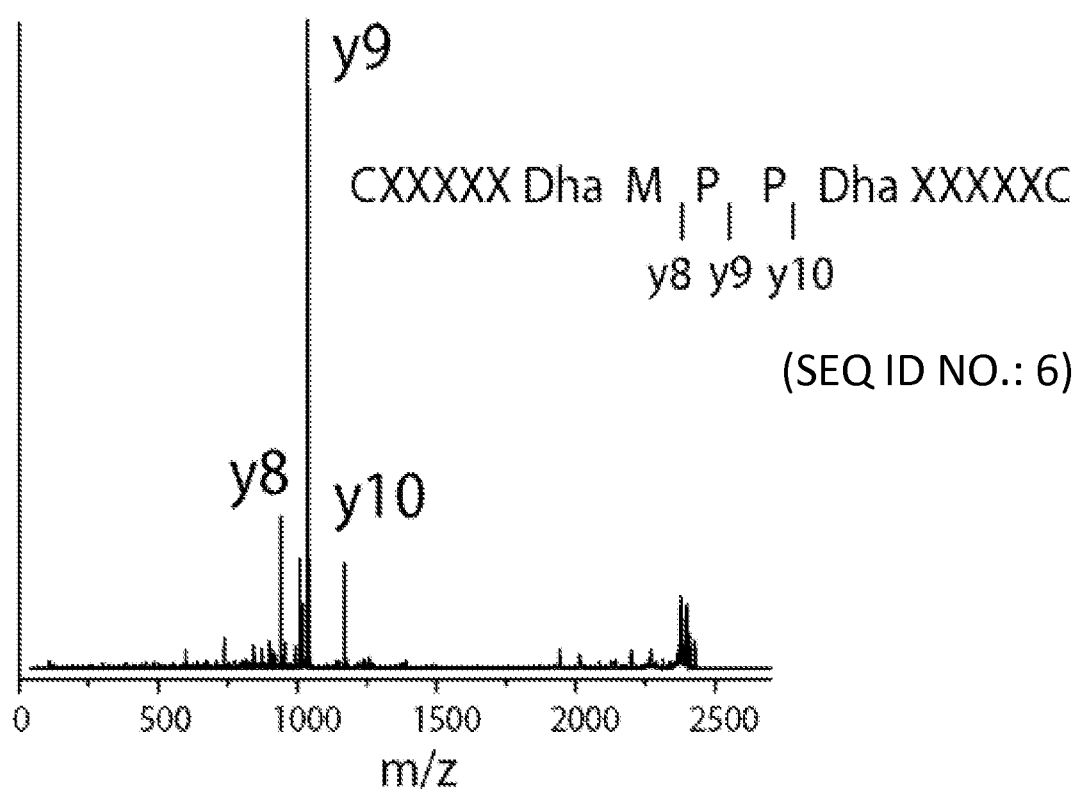
Figure 7C:
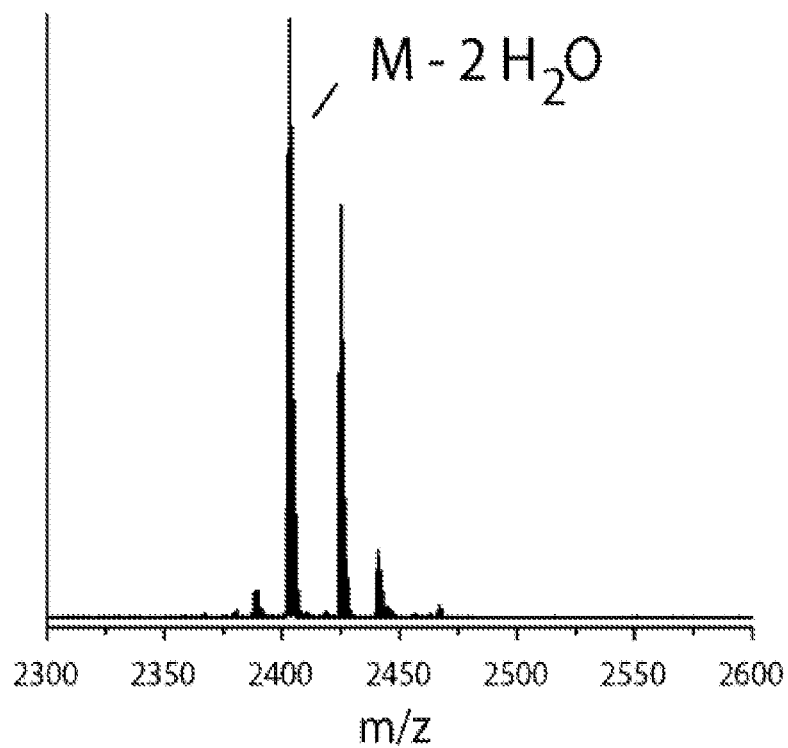
FIG. 7C depicts mass spectrometry analysis of the peptide 2.8-9 modified by ProcM in *E. coli* and treated with GluC. Calculated mass for M−2 H$_2$O+H for peptide 2.8-9: 2438−2*18+1=2403 Da, Obsrvd 2402 Da.
Figure 7D:
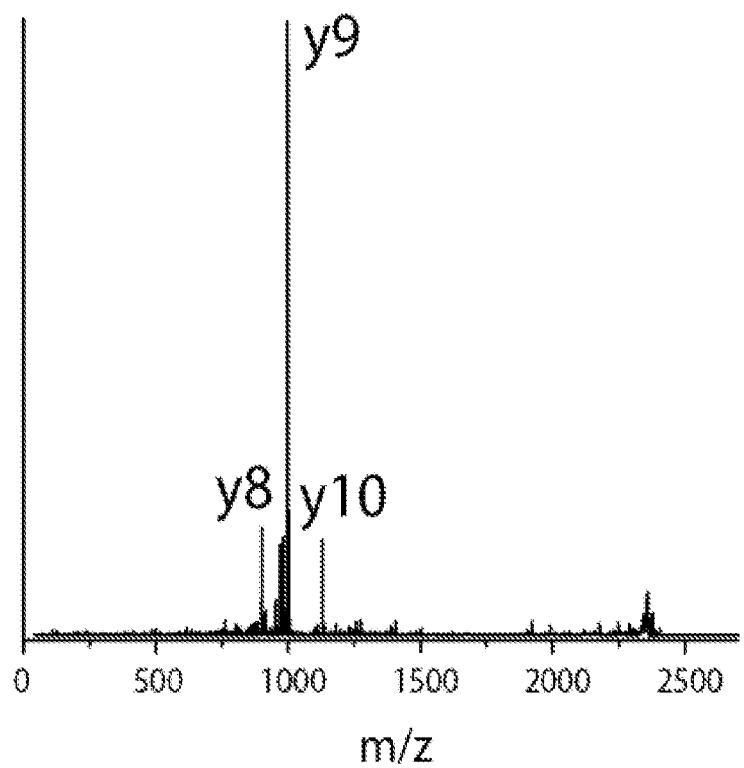
FIG. 7D depicts tandem mass spectrometry analysis of the peptide presented in FIG. 7C.
Figure 7E:
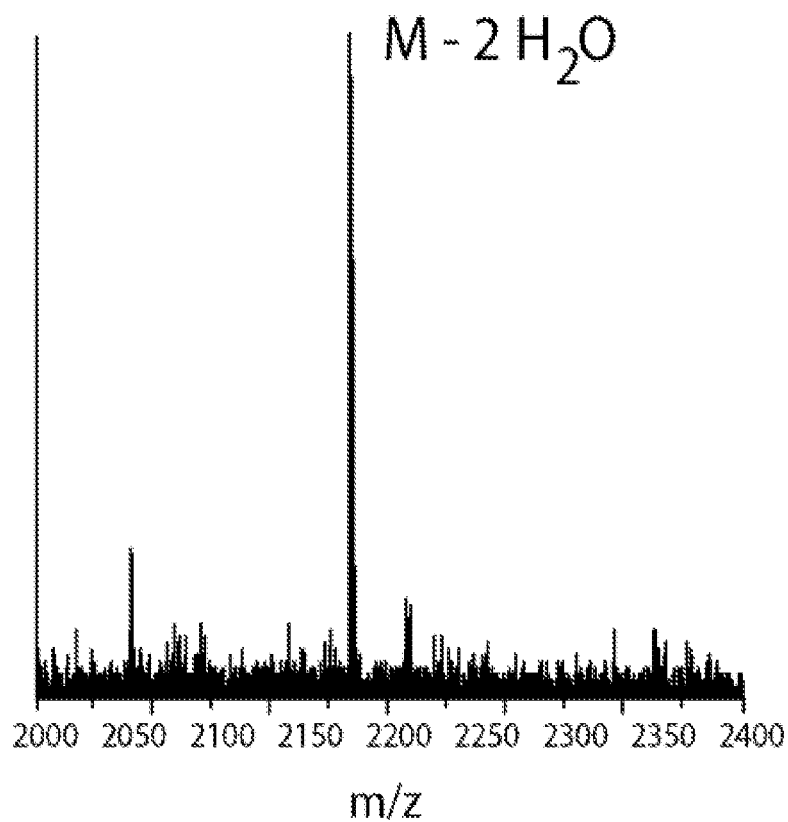
FIG. 7E depicts mass spectrometry analysis of the peptide 2.8-10 modified by ProcM in *E. coli* and treated with GluC.
Figure 7F:
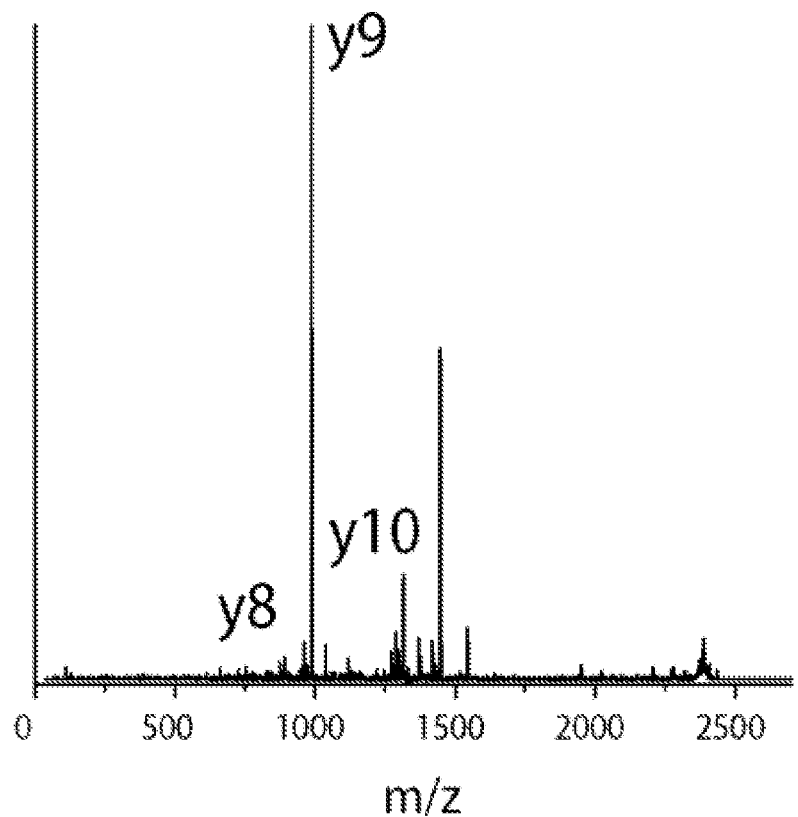
FIG. 7B depicts tandem mass spectrometry analysis of the peptide presented in FIG. 7A.

FIG. 7F depicts tandem mass spectrometry analysis of the peptide presented in FIG. 7E.

Figure 8A:
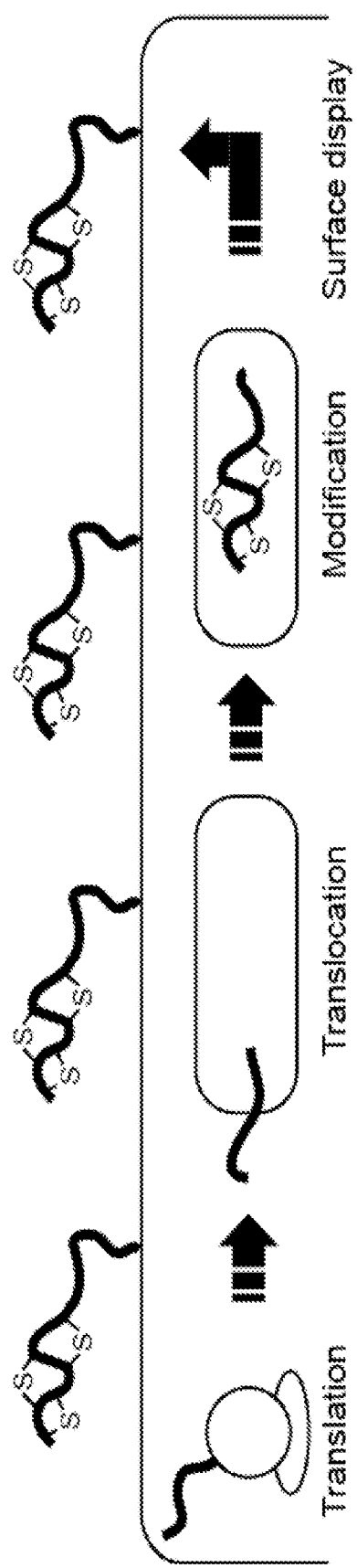

FIG. 8A depicts an approach for yeast surface display of lanthipeptides, wherein peptides must be heterologously expressed in yeast, transferred to the secretion machinery, and modified prior to being displayed on the yeast surface.

Figure 8B:
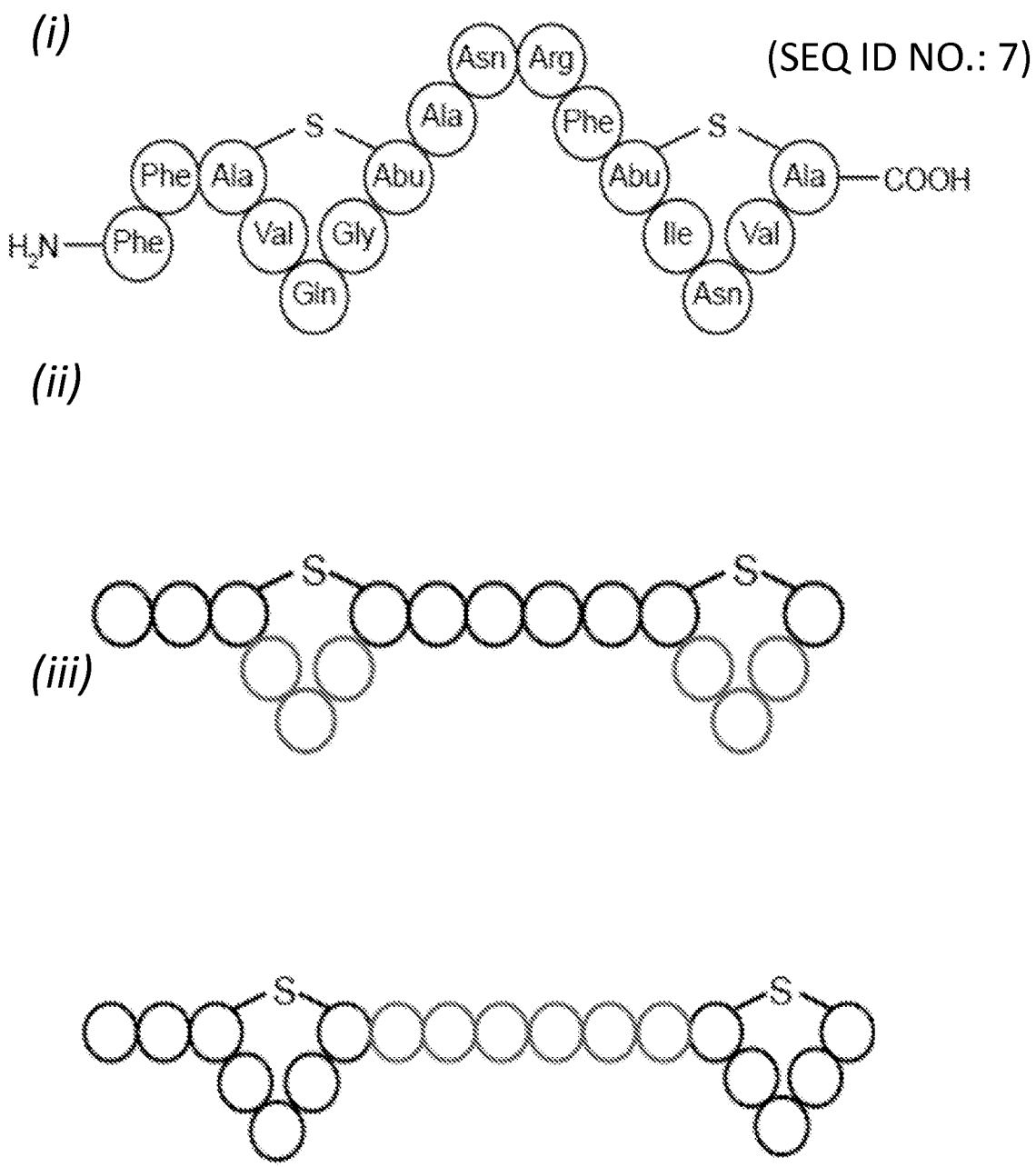

FIG. 8B depicts prochlorosin 1.1 (panel (i)), which can be used as scaffolds (panels (ii) and (iii)) for library production, with randomized amino acids incorporated at various locations within their structures (red circles). Sequences within rings or between rings can be randomized, or amino acids within rings or between rings can be deleted or inserted.

Figure 8C:
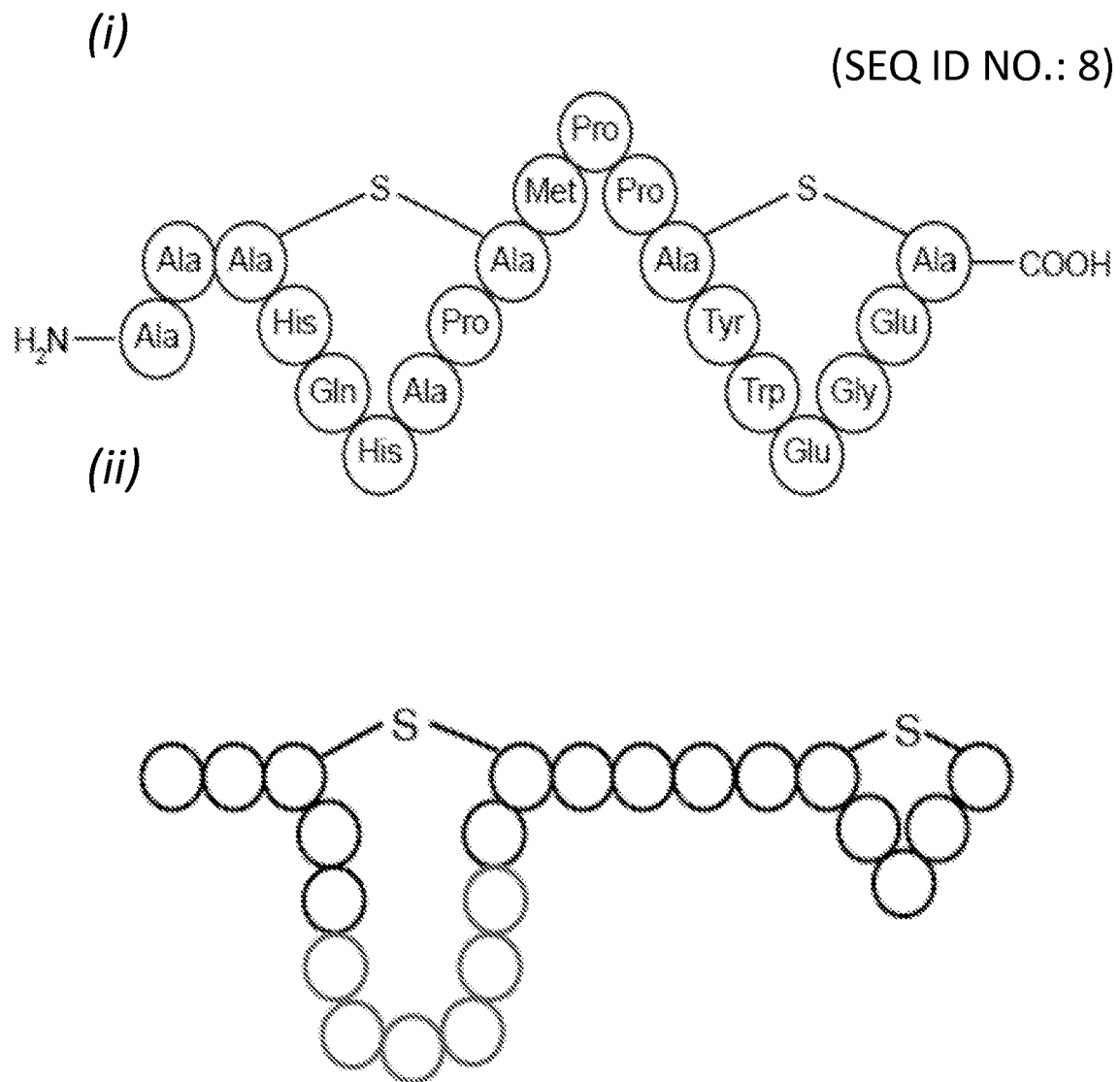

FIG. 8C depicts prochlorosin 2.8 (panel (i)), which can be used as scaffolds (panel (ii)) for library production, with randomized amino acids incorporated at various locations within their structures (red circles). An example is shown of inserting amino acids in the left ring and deleting amino acids in the right ring.

Figure 9A:
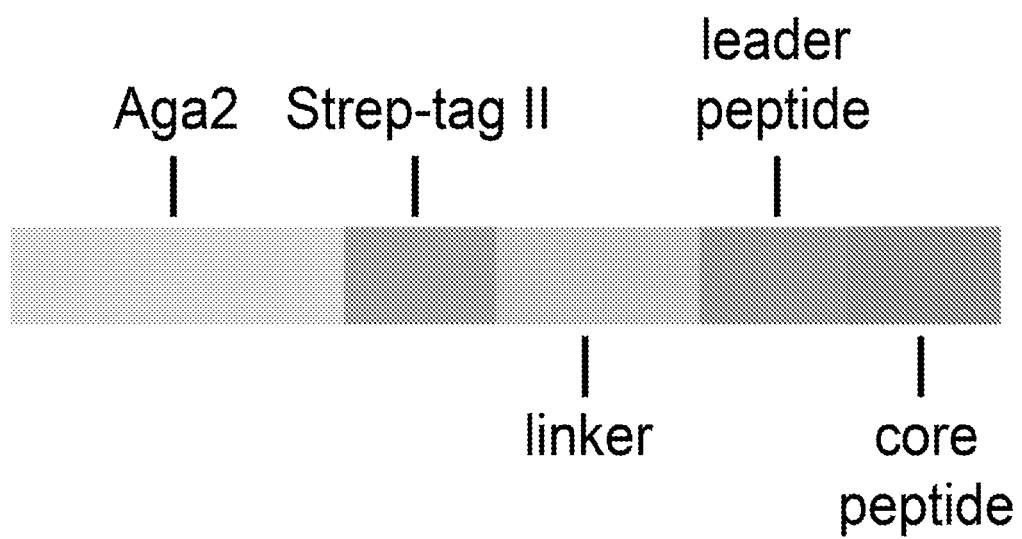

FIG. 9A depicts one construct for surface display of lanthipeptides, wherein the N-terminal LanA anchoring construct contains Aga2 followed by an Strep-tag II, a serine and glycine linker region, and the leader and core of the LanA (note that Aga2-LctA secretion is directed by Aga2's native secretion signal).

Figure 9B:
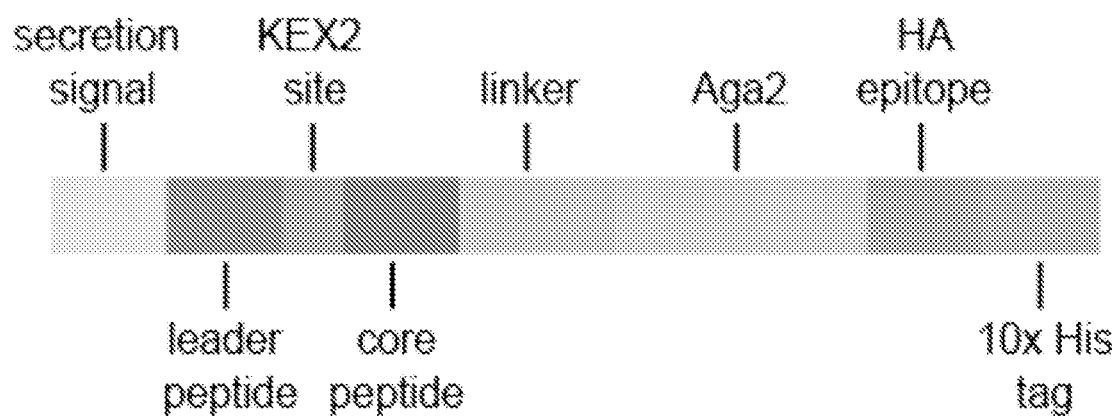

FIG. 9B depicts one construct for surface display of lanthipeptides, wherein the C-terminal LanA anchoring construct contains a secretion signal, the leader peptide of the LanA, a KEX2 cleavage site for in vivo removal of the leader peptide, the LanA core peptide, a serine and glycine linker region, Aga2, and HA epitope tad and a 10 histidine tag to facilitate purification.

Figure 9C:
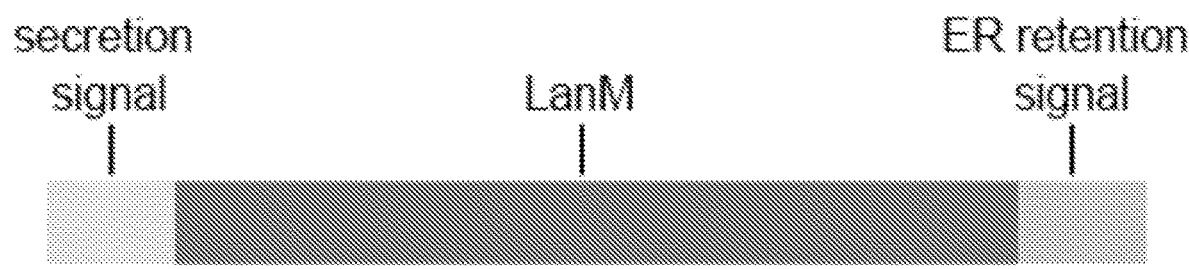

FIG. 9C depicts a representation for LanMs, wherein a secretion signal is present to target them to the ER and a retention tag to prevent them from being secreted.

Figure 10A:
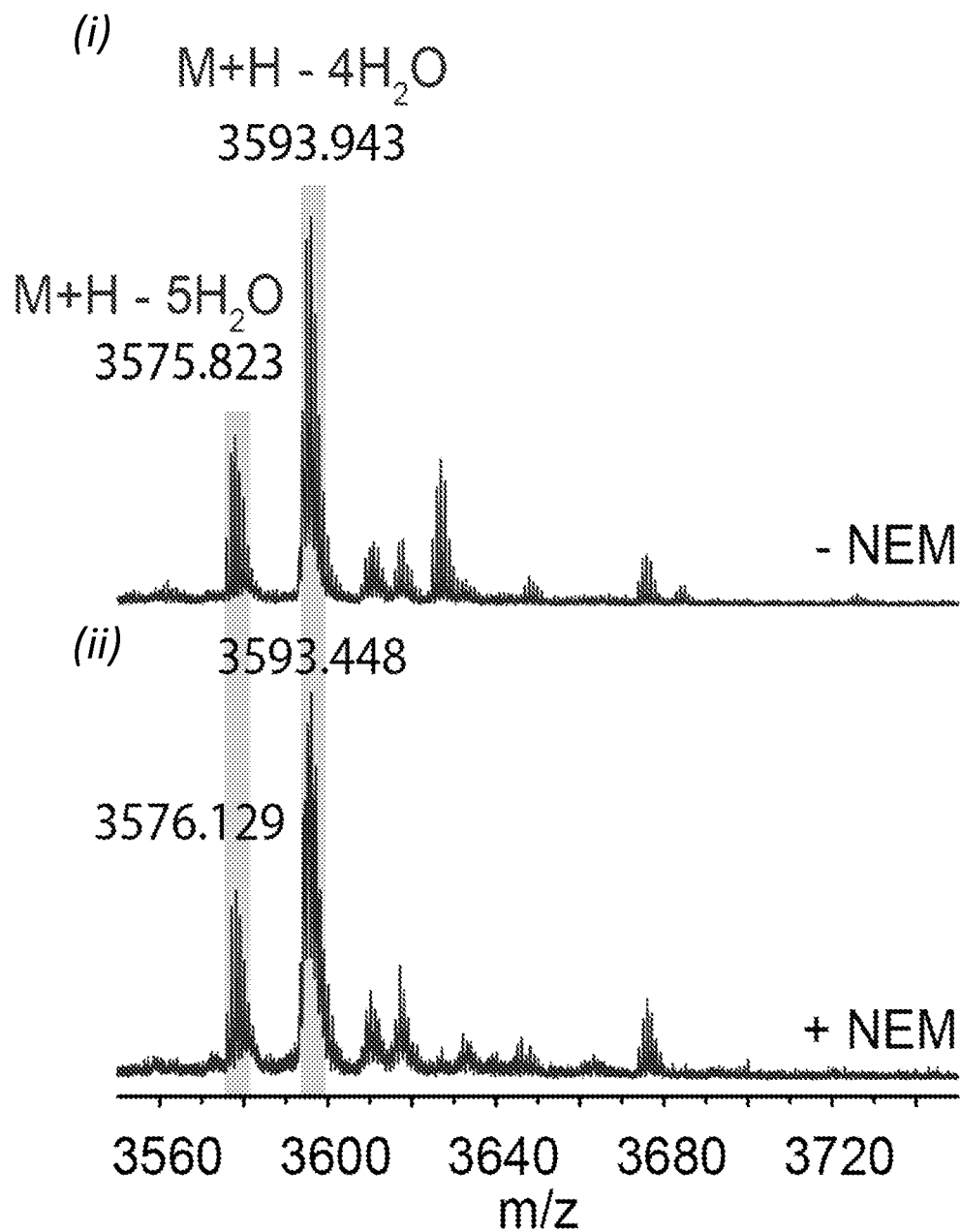

FIG. 10A depicts exemplary mass spectroscopy analysis of core peptides of Aga2-LctA N-terminal LanA fusion protein in the absence (panel (i)) or presence (panel (ii)) of N-ethylmaleimide (NEM) treatment. The N-terminal Aga2-LanA fusion construct exhibits the mass of the core peptide after protease digestion (LctA M+H: 3,594) with the expected losses of water (LctA: 4) and no NEM adducts illustrating full cyclization.

Figure 10B:
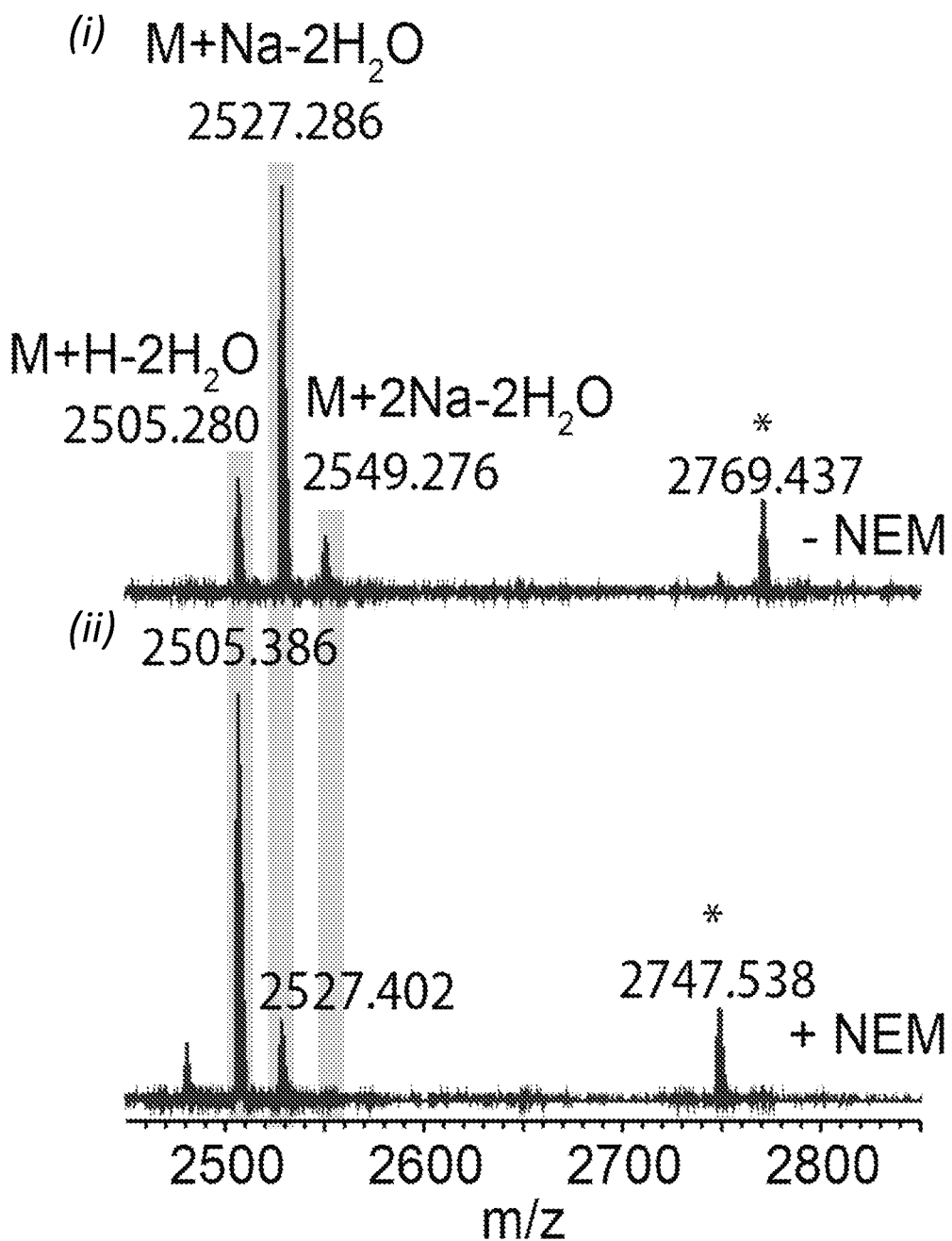

FIG. 10B depicts exemplary mass spectroscopy analysis of core peptides of Aga2-ProcA 2.8 N-terminal LanA fusion protein in the absence (panel (i)) or presence (panel (ii)) of N-ethylmaleimide (NEM) treatment. The N-terminal Aga2-ProcA 2.8 fusion construct exhibits the mass of the core peptide after protease digestion (ProcA 2.8 M+H: 2,527) with the expected losses of water (ProcA 2.8: 2) and no NEM adducts illustrating full cyclization.

Figure 10C:
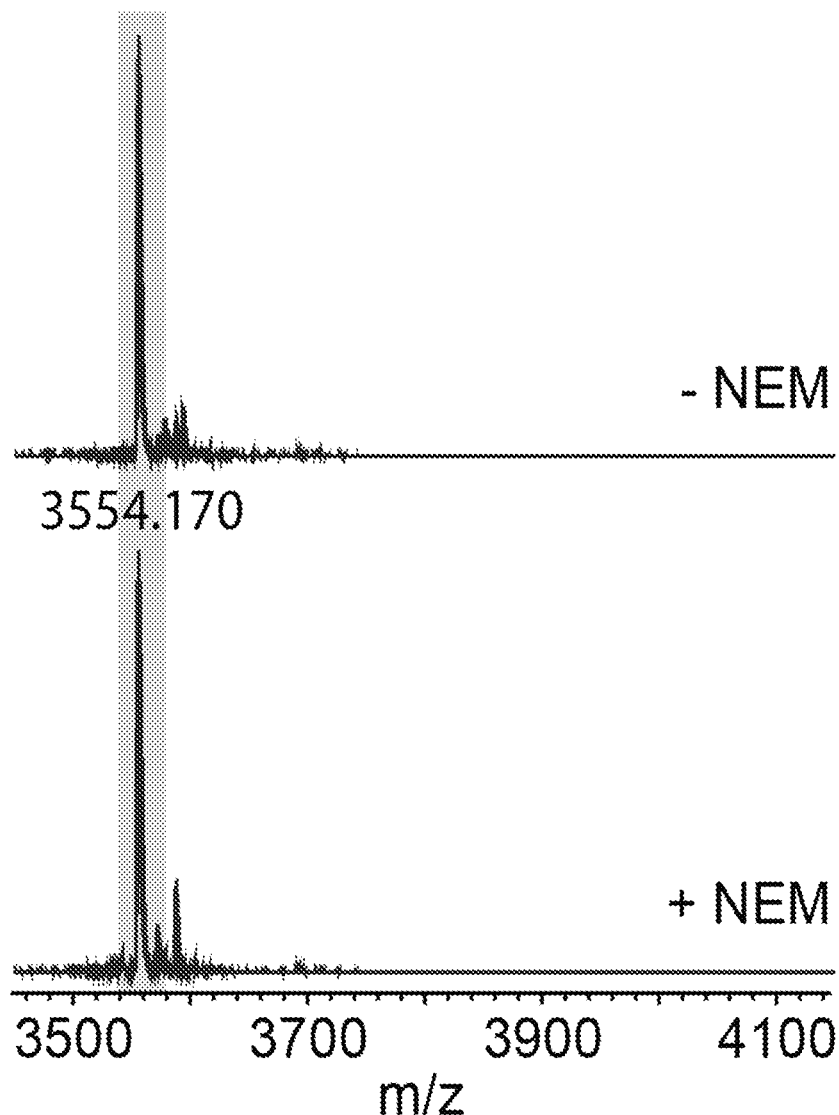

FIG. 10C depicts exemplary mass spectroscopy analysis of core peptides of Aga2-HalA2 2.8 N-terminal LanA fusion protein in the absence (panel (i)) or presence (panel (ii)) of N-ethylmaleimide (NEM) treatment. The N-terminal Aga2-HalA2 fusion construct exhibits the mass of the core peptide after protease digestion (HalA2 M+H: 3,554) with the expected losses of water (HalA2: 7) and no NEM adducts illustrating full cyclization.

Figure 10D:
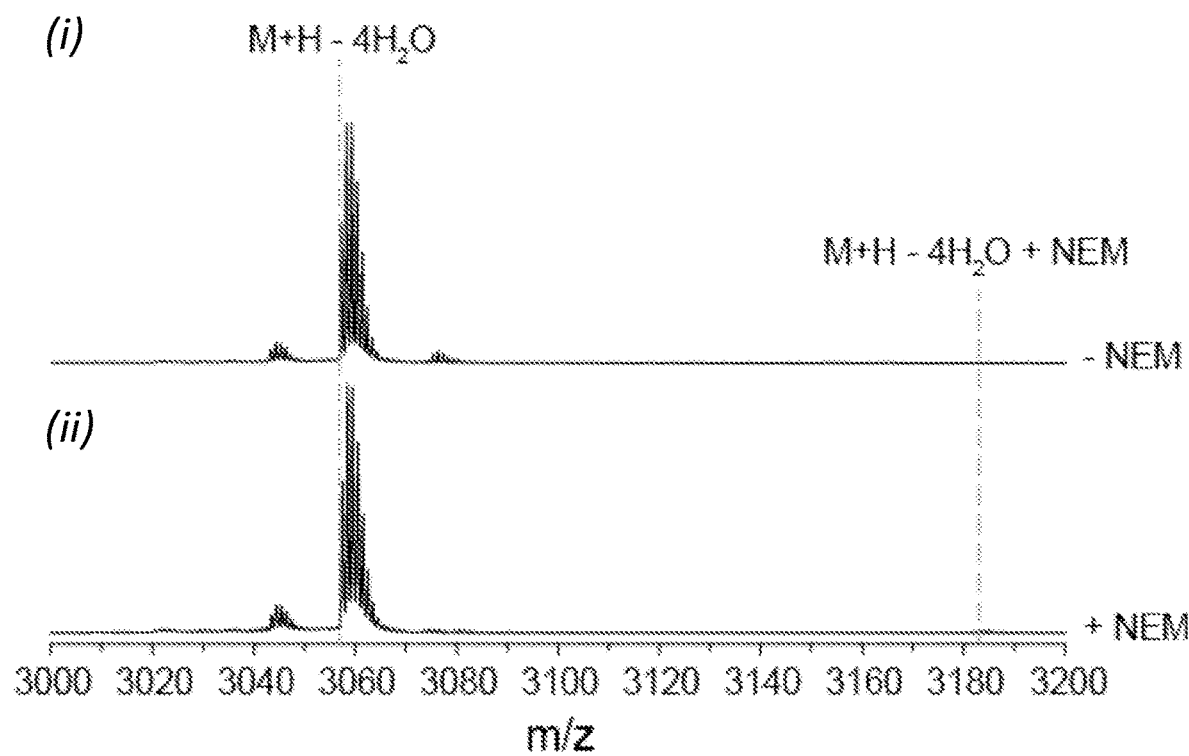

FIG. 10D depicts an exemplary mass spectroscopy analysis of core peptides of C-terminal LctA fusion proteins in the absence (panel (i)) or presence (panel (ii)) of N-ethylmaleimide (NEM) treatment. The LctA-Aga2 construct exhibits the mass of the core peptide following protease digestion (M+H: 3,129) with a loss of 4 waters and a small amount of a single NEM adduct.

Figure 1:
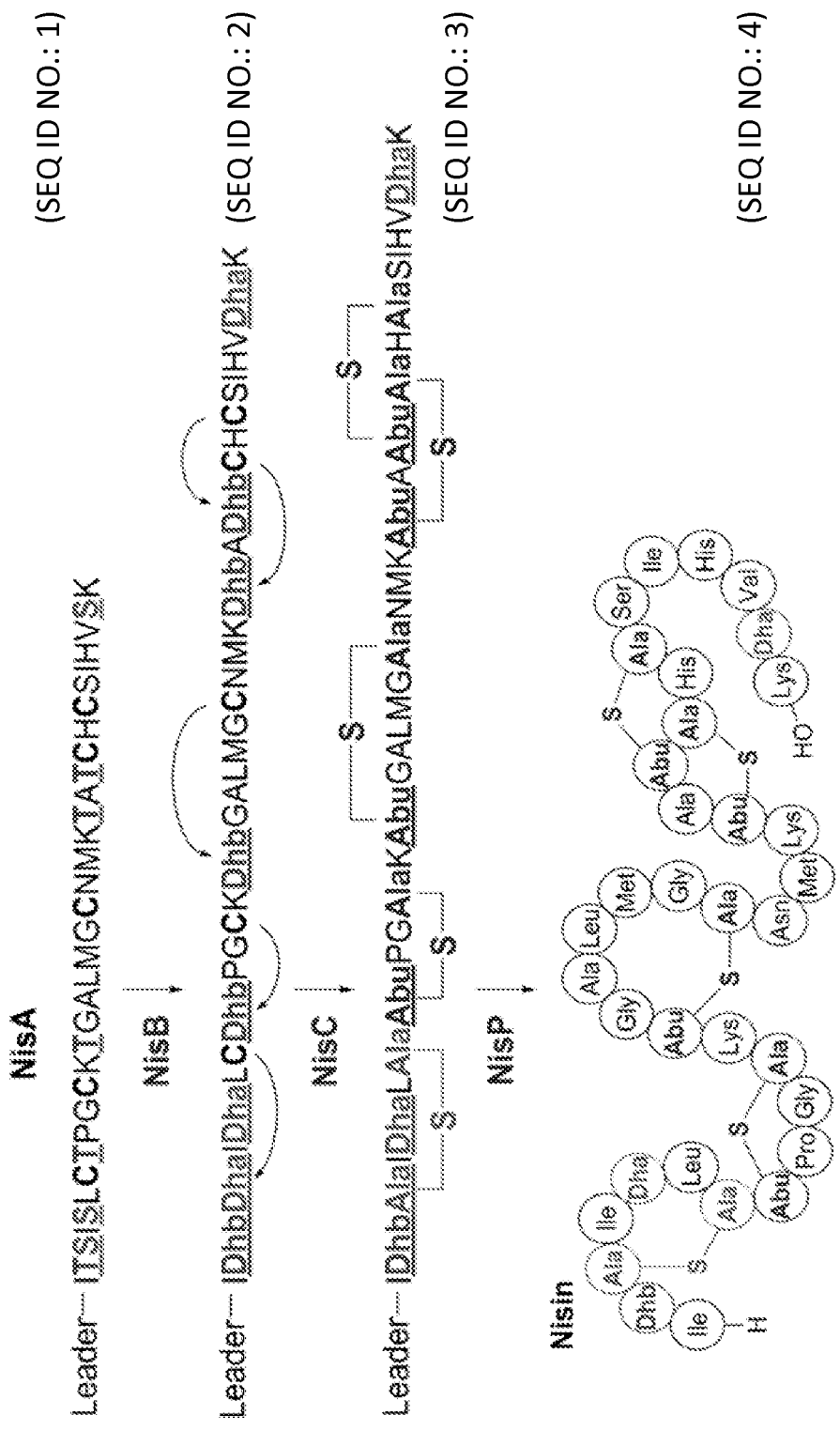
FIG. 1 depicts posttranslational modifications in nisin biosynthesis. NisB dehydrates eight threonines/serines in NisA, whereas NisC forms five thioether crosslinks by Michael-type addition of cysteine thiols onto the dehydrated amino acids. Dha, dehydroalanine; Dhb, dehydrobutyrine; Abu, 2-aminobutyric acid.
Figure 10E:
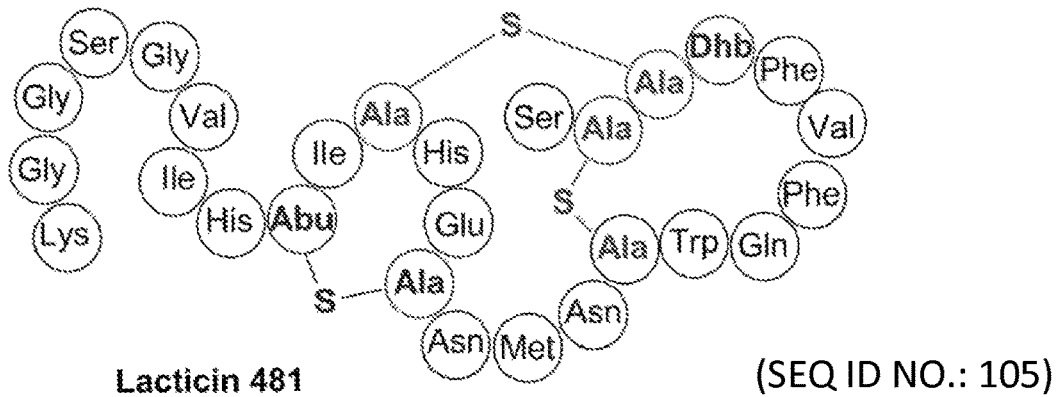
Figure 10E:
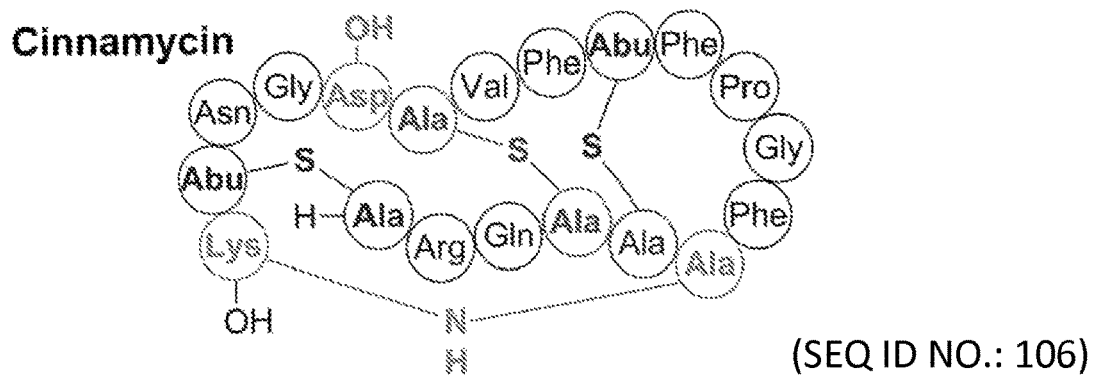
Figure 10E:
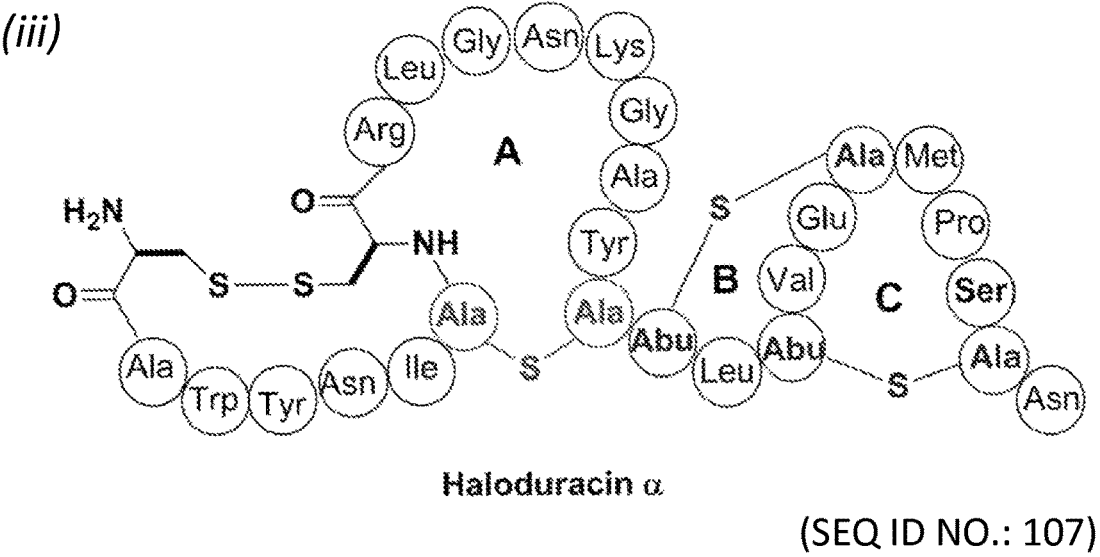

FIG. 10E depicts structural representation of lacticin 481 (panel (i)), cinnamycin (panel (ii)) and Hala (panel (iii)), one of the two components of haloduracin. Dha, dehydroalanine; Dhb, dehydrobutyrine; Abu, 2-aminobutyric acid. The shorthand notation introduced in FIG. 1 is used.

Figure 11A:
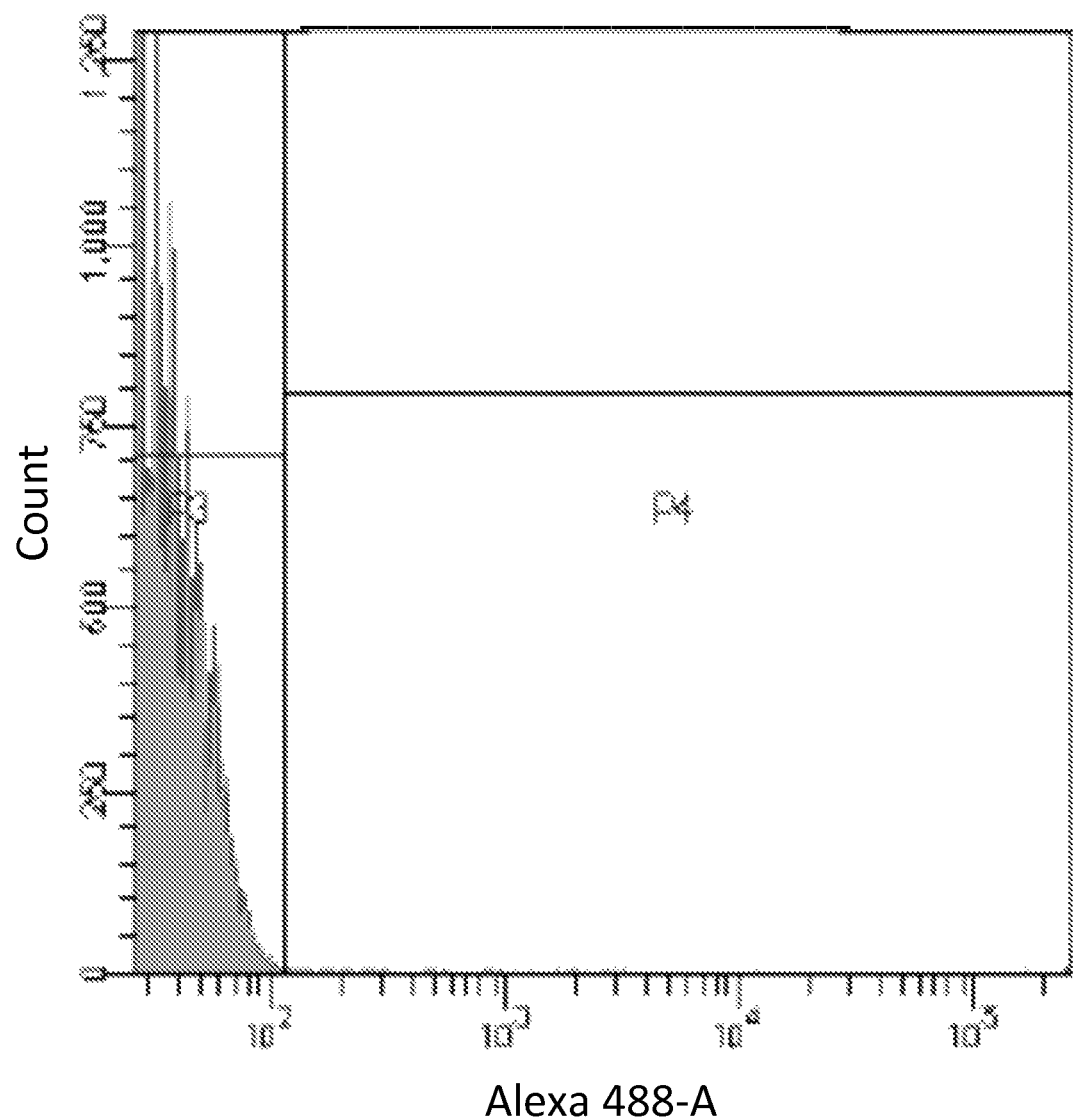

FIG. 11A depicts an exemplary flow cytometry analysis showing no Aga2-LctA presentation on the surface of uninduced yeast.

Figure 11B:
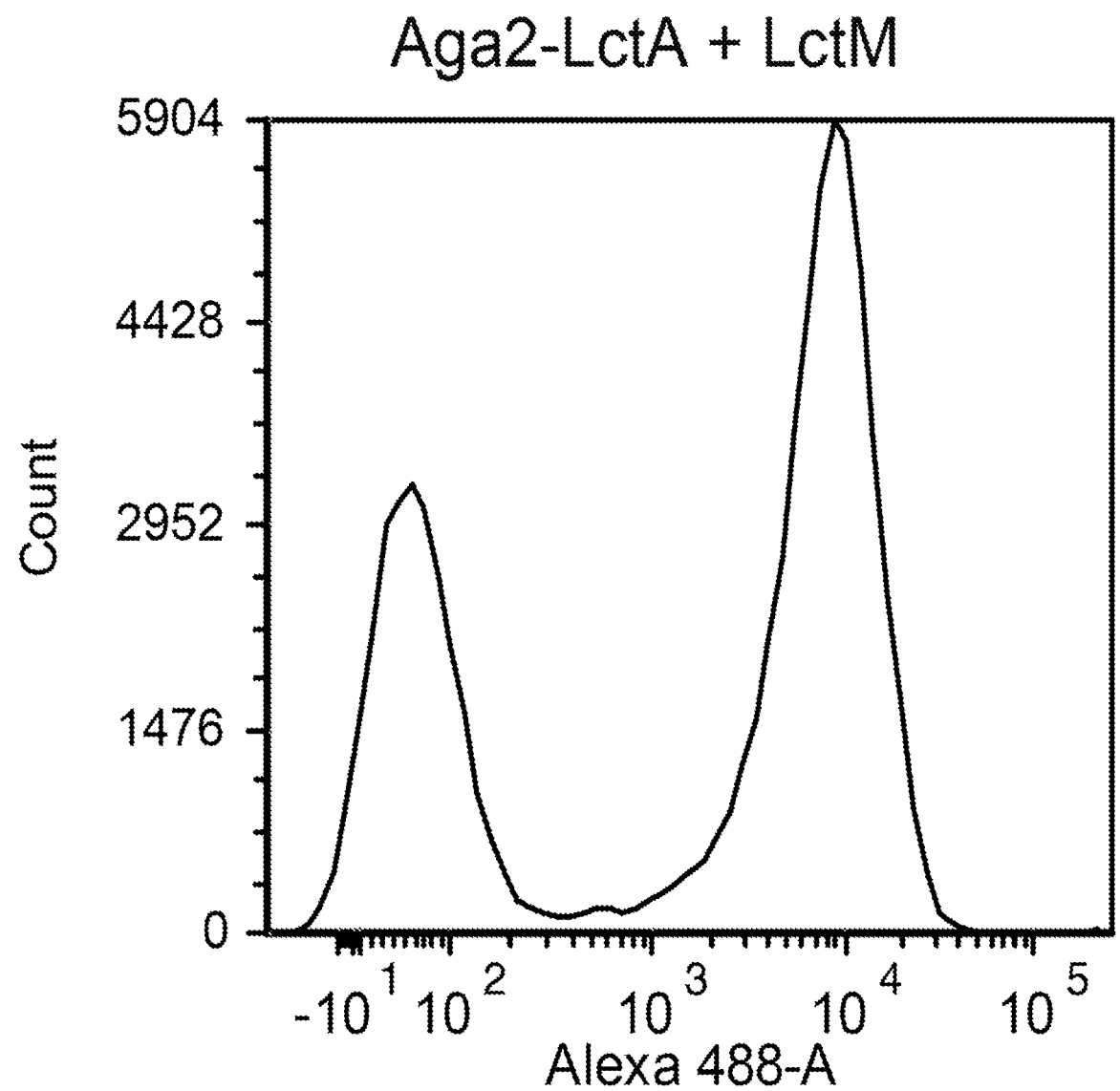

FIG. 11B depicts an exemplary flow cytometry analysis showing the Aga2-LctA construct is displayed on the surface of the yeast induced to co-express Aga2-LctA and the respective LctM.

Figure 11C:
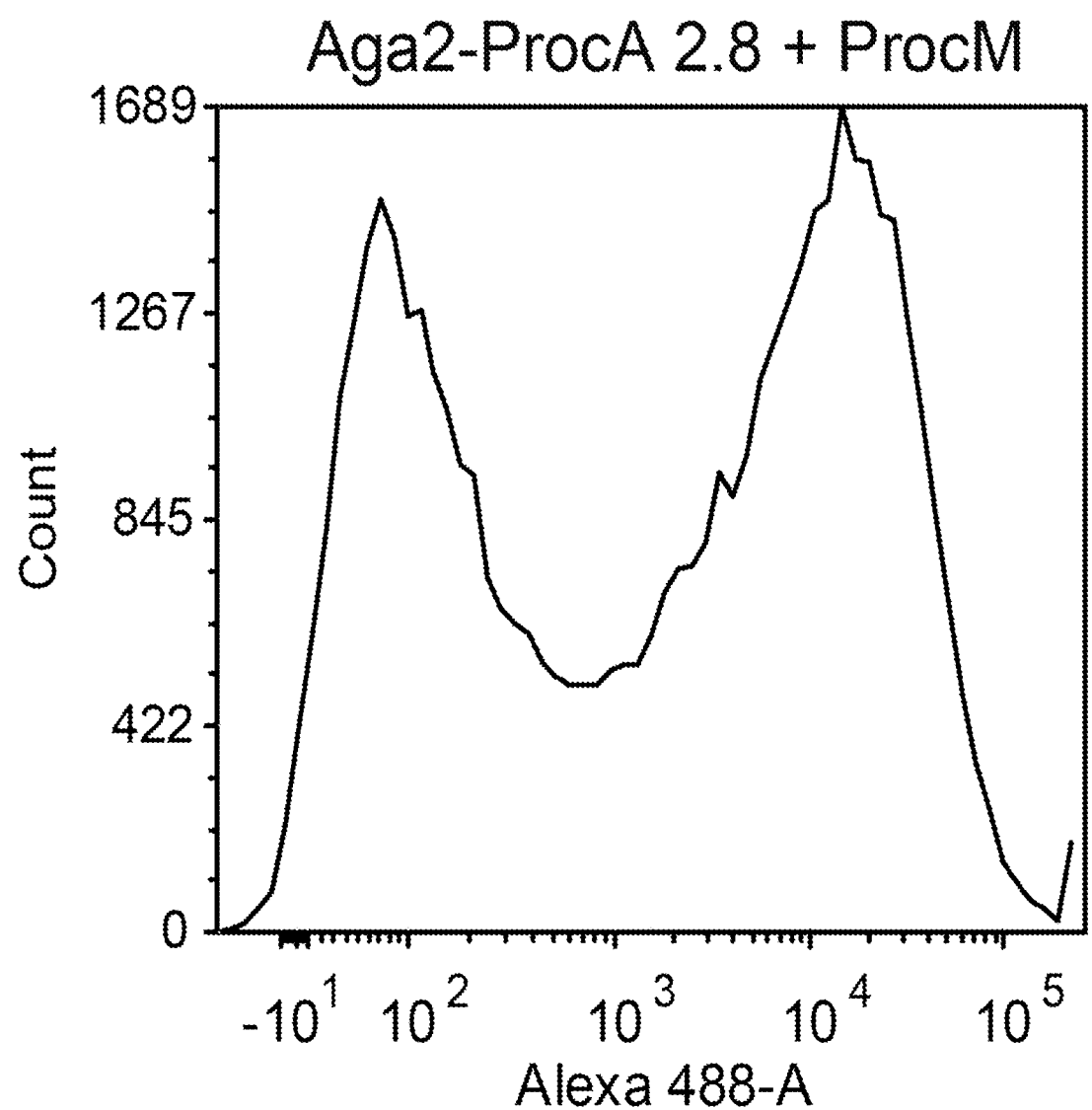

FIG. 11C depicts an exemplary flow cytometry analysis showing the Aga2-ProcA 2.8 construct is displayed on the surface of the yeast induced to co-express Aga2-ProcA 2.8 and the respective ProcM.

Figure 11D:
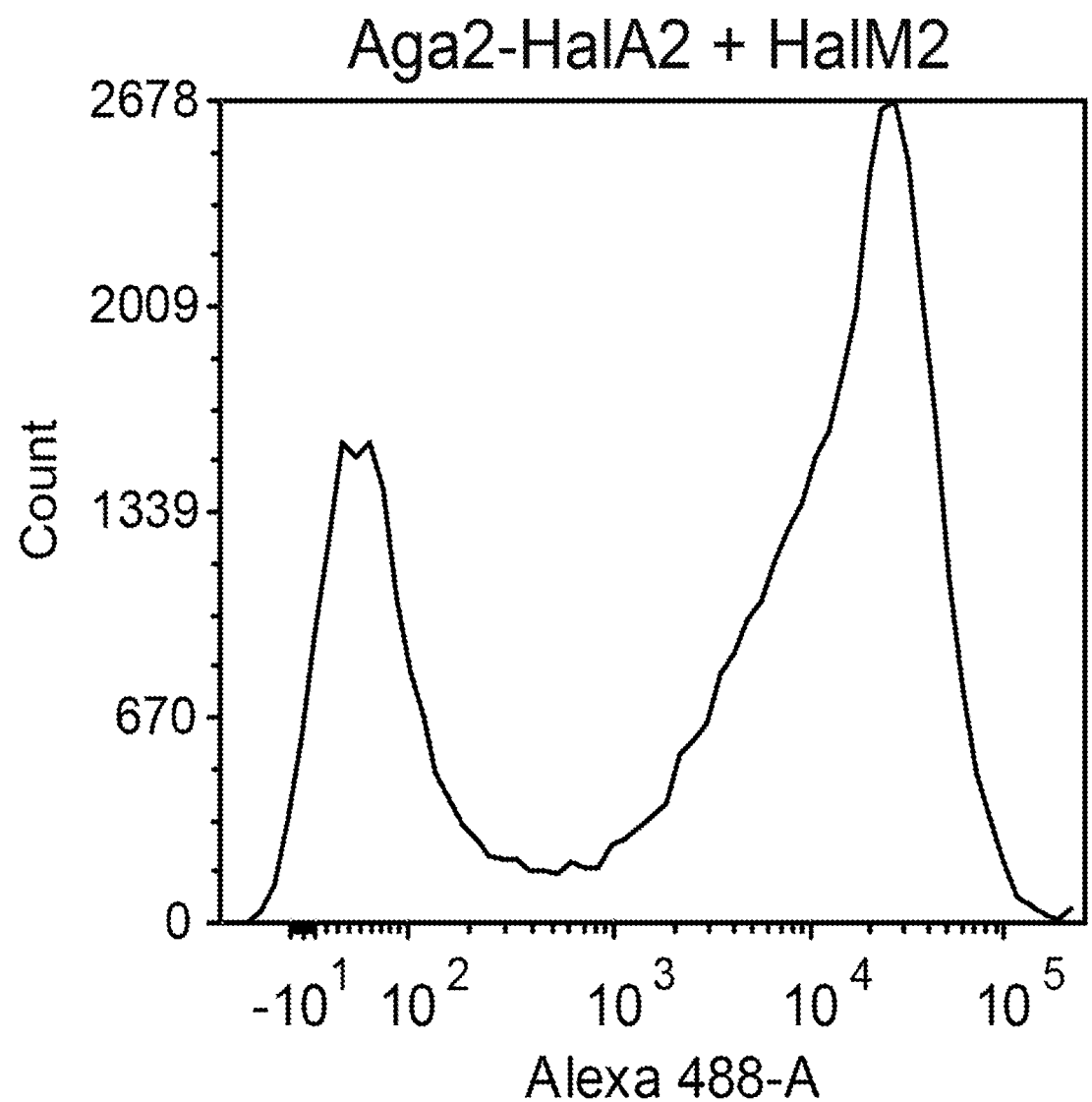

FIG. 11D depicts an exemplary flow cytometry analysis showing the Aga2-HalA2 construct is displayed on the surface of the yeast induced to co-express Aga2-HalA2 and the respective HalM2.

Figure 11E:
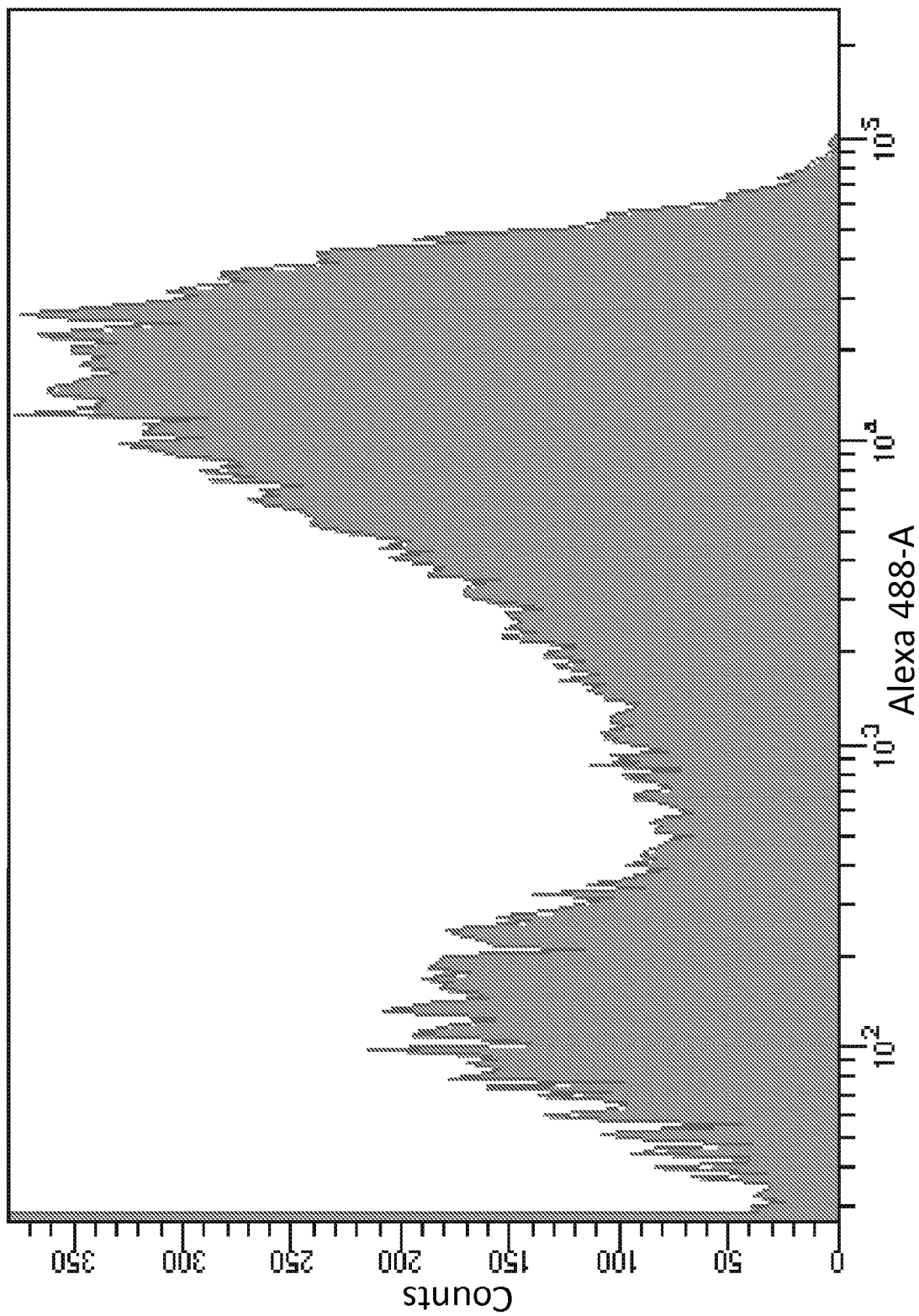

FIG. 11E depicts an exemplary flow cytometry analysis showing the LctA-Aga2 construct is displayed on the surface of the yeast induced to co-express LctA-Aga2 and LctM.

Figure 11F:
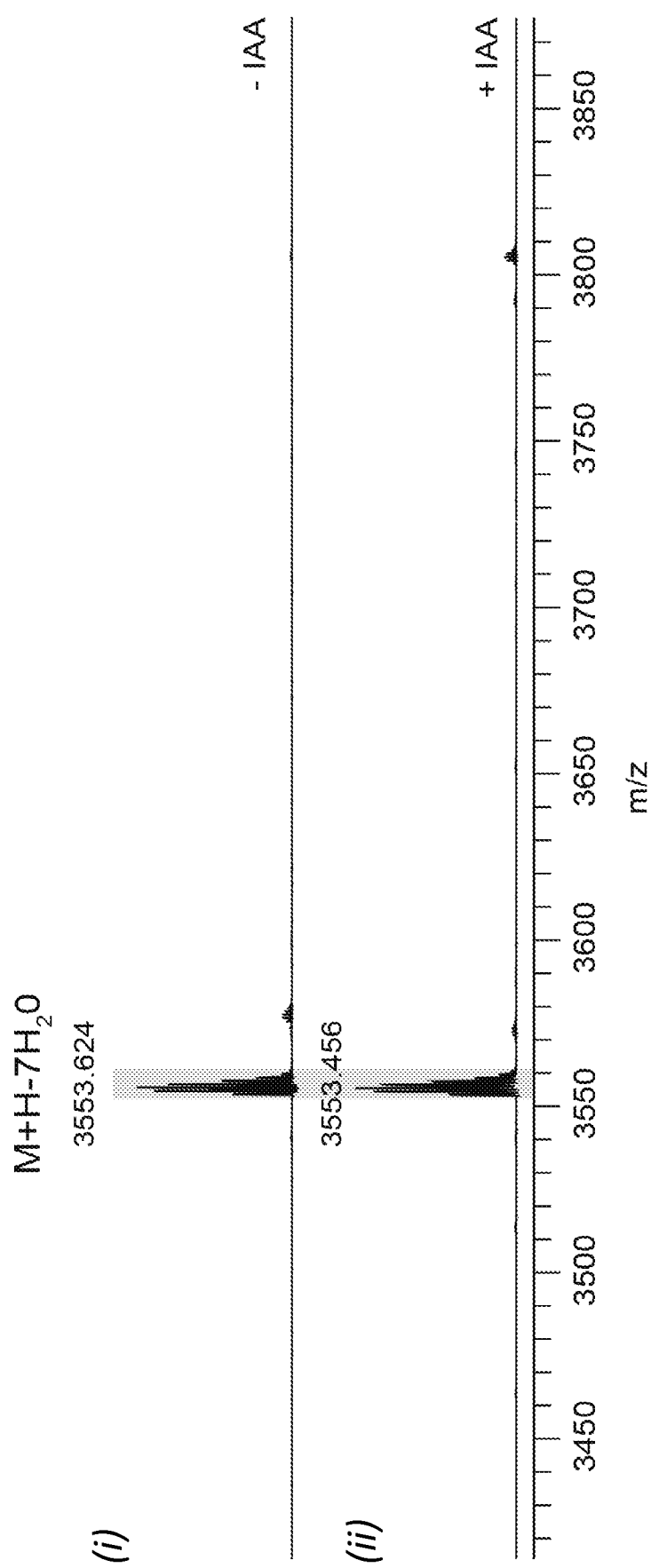

FIG. 11F depicts an exemplary MALDI-TOF MS analysis showing the core peptide from Aga2-HalA2 is 7-fold dehydrated and no iodoacetamide (IAA) adducts are observed indicating full cyclization.

While the present invention is amenable to various modifications and alternative forms, exemplary aspects thereof are shown by way of example in the drawings and are herein described in detail. It should be understood, however, that the description of exemplary aspects is not intended to limit the invention to the particular forms disclosed, but on the contrary, the intention is to cover all modifications, equivalents and alternatives falling within the spirit and scope of the invention as defined by the aspects above and the claims below. Reference should therefore be made to the aspects and claims herein for interpreting the scope of the invention.

DETAILED DESCRIPTION

The methods now will be described more fully hereinafter with reference to the accompanying drawings, in which some, but not all permutations and variations of aspects of the invention are shown. Indeed, the invention may be embodied in many different forms and should not be construed as limited to the aspects set forth herein. These aspects are provided in sufficient written detail to describe and enable one skilled in the art to make and use the invention, along with disclosure of the best mode for practicing the invention, as defined by the claims and equivalents thereof.

Likewise, many modifications and other aspects of the methods described herein will come to mind to one of skill in the art to which the invention pertains having the benefit of the teachings presented in the foregoing descriptions and the associated drawings. Therefore, it is to be understood that the invention is not to be limited to the specific aspects disclosed and that modifications and other aspects are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Certain terms are first defined. Additional terms are defined throughout the specification.

Terms used herein are intended as "open" terms (for example, the term "including" should be interpreted as "including but not limited to," the term "having" should be interpreted as "having at least," the term "includes" should be interpreted as "includes but is not limited to," etc.).

Furthermore, in those instances where a convention analogous to "at least one of A, B and C, etc." is used, in general such a construction is intended in the sense of one having ordinary skill in the art would understand the convention (for example, "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "from," "to," "up to," "at least," "greater than," "less than," and the like, include the number recited and refer to ranges which can subsequently be broken down into sub-ranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described aspects or features contained within the same. Where no options or choices are disclosed regarding a particular aspect or feature contained in the same, the modal verb "may" refers to an affirmative act regarding how to make or use and aspect of a described aspect or feature contained in the same, or a definitive decision to use a specific skill regarding a described aspect or feature contained in the same. In this latter context, the modal verb "may" has the same meaning and connotation as the auxiliary verb "can."

As used herein, the articles "a" and "an" refer to one or to more than one (for example, to at least one) of the grammatical object of the article.

"About" and "approximately" shall generally mean an acceptable degree of error for the quantity measured given the nature or precision of the measurements. Exemplary degrees of error are within 20-25 percent (%), typically, within 10%, and more typically, within 5% of a given value or range of values.

As used herein, "phagemid" or "phasmid" refers to a plasmid having at least a bacteriophage f1 origin of replication and optionally a bacterial origin of replication. As disclosed herein, phagemids or phasmids can include additional genetic elements, such as a gene encoding a polypeptide capable of conferring an antibiotic resistance phenotype to a recipient host organism, as well as genes encoding additional polypeptides or chimera polypeptides.

Headings, for example, (a), (b), (i) etc., are presented merely for ease of reading the specification and claims. The use of headings in the specification or claims does not require the steps or elements be performed in alphabetical or numerical order or the order in which they are presented.

The present disclosure describes robust platforms, systems and methods for synthesizing engineered lanthipeptides in vivo from recombinant organisms using phage display in bacteria and host surface display in yeast. The methods use lanthipeptide libraries as molecular reagents to survey diverse lanthipeptide species in which novel lanthipeptides are expressed in vivo in recombinant host organisms expressing lanthipeptide biosynthetic enzymes.

Lanthipeptide-Based Phage Display Platforms

In a first aspect, a platform for displaying lanthipeptides on M13 phage is provided. The utility of the platform is demonstrated for displaying the lantibiotic nisin on M13 phage. A previously developed nisin production system can be adapted for this purpose, in which the precursor peptide NisA is modified by the enzymes NisB and NisC in *E. coli*. (Shi, Y., Yang, X., Garg, N., and van der Donk, W. A. "Production of lantipeptides in *Escherichia coli*," *J. Am. Chem. Soc.* 133:2338-2341 (2010).) Phage display of nisin was envisioned by heterologous expression of the precursor peptide NisA fused to a phage display protein in the presence of the modifying enzymes NisB and NisC and the genes required for forming other phage components in *E. coli*. In this strategy, the NisA peptide fused to the phage display protein was modified in *E. coli* and incorporated with the phage components into phage displaying the corresponding lantibiotic. It is possible that the leader peptide of the modified NisA, once exported into the periplasm, may be cleaved by the OmpT protease. This would not affect the display of the nisin structure.

M13 phage contains three to five pIII proteins on M13 phage that are responsible for the attachment of phage on to the pilus of *E. coli* during the infection process with which the phage propagates. This protein is the most common protein used for display of peptides, however fusing a peptide onto pIII impairs its ability to recognize its native primary and secondary receptors. In conventional phage display, phagemid encodes for pIII proteins that are fused to the displaying peptide, whereas helper phage M13K07 or VCSM13 encode for wild type pIII sustaining the infection function.

Figure 2A:
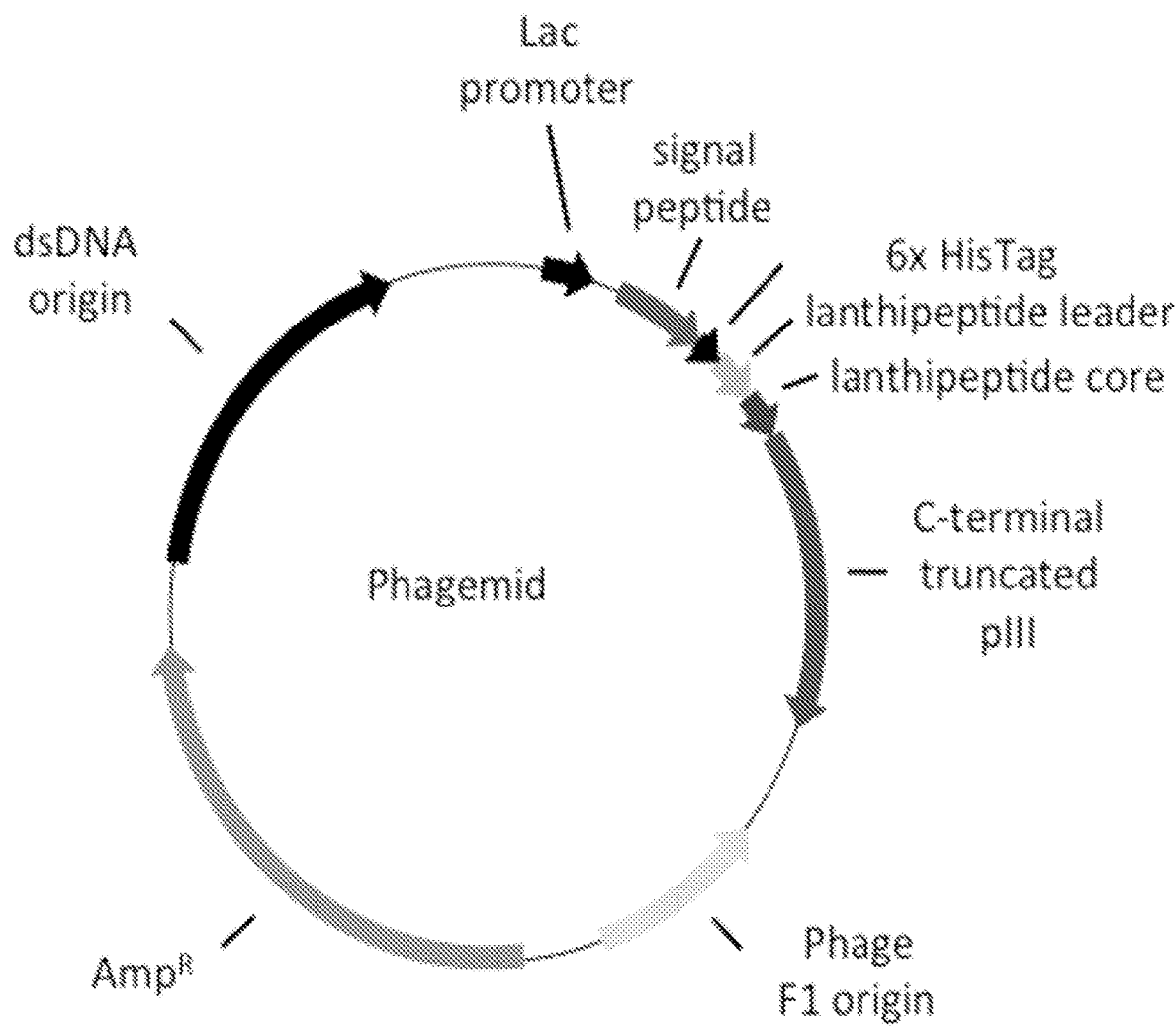
FIG. 2A depicts an exemplary phagemid engineered to encode for a fusion protein to pIII (encoded by gIII). It consists of an origin of replication in *E. coli* (dsDNA ori; double stranded DNA origin) and the f1 origin that is used for propagation of phage. Key: $Amp^R$: ampicillin resistance gene; and gIII: gene III.
Figure 2B:
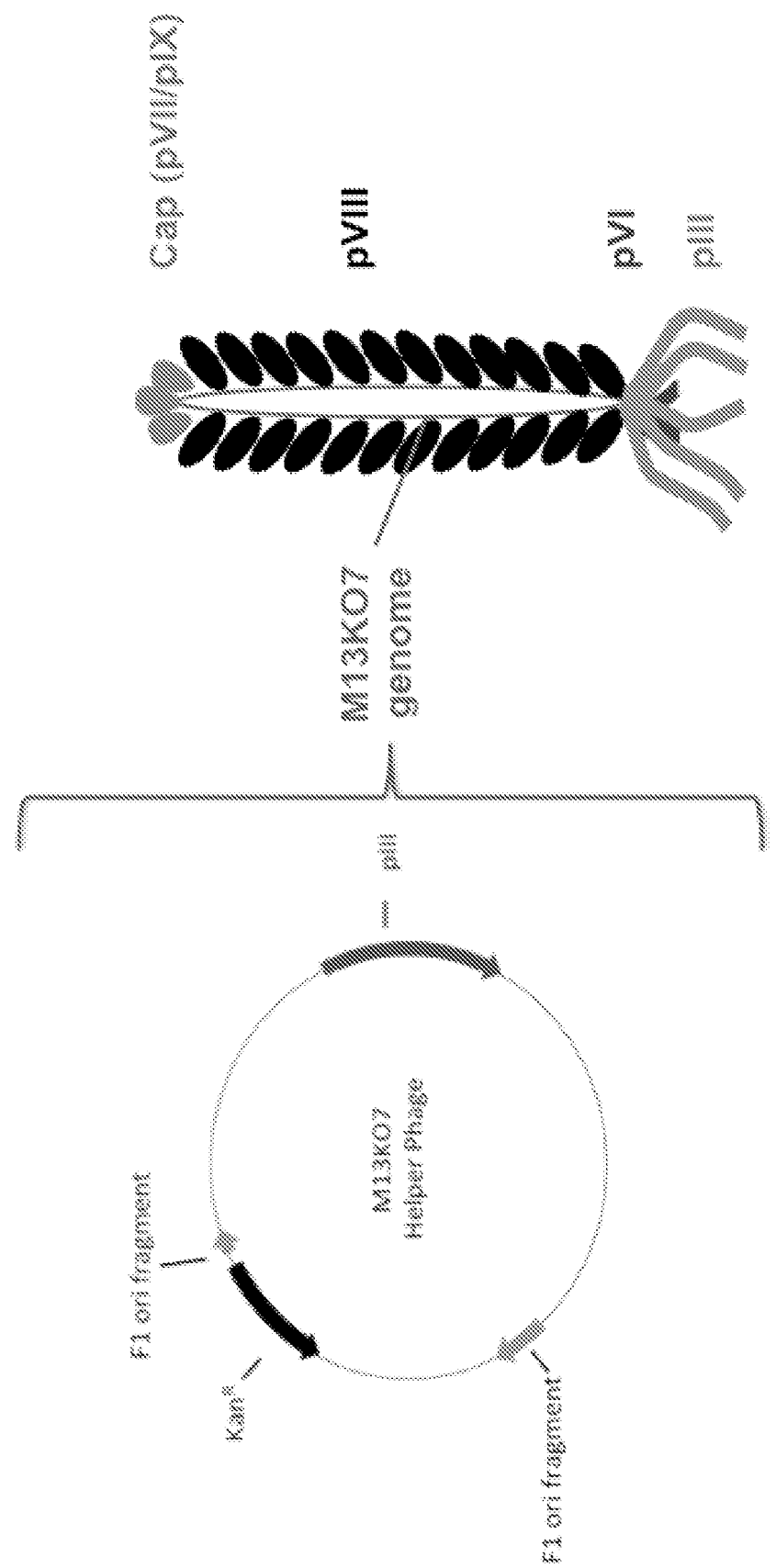
FIG. 2B depicts an exemplary helper phage including a single stranded DNA encoding for phage proteins including pIII, used for display of the lantibiotic nisin. M13KO7 helper phage genome is shown in red. Other genes on the genome are not shown. The phagemid depicted in FIG. 2A was used to display a peptide whose C-terminus is fused to the N-terminus of truncated pIII. Key: $Kan^R$: kanamycin resistance gene; gIII: gene III; pIII, protein III; pVII: protein VII; pIX: protein IX; pVIII: protein VIII; and pVI: protein VI.

The phage display technique generally utilizes two main components. One is a phagemid or phasmid, which is a plasmid that contains an f1 origin of replication enabling single stranded DNA replication observed in f1 phage as well as a double-stranded origin of replication, which allows propagation as a plasmid in a bacterial host. In other words, a phagemid can replicate as a plasmid, and also can provide single stranded DNA that can be packaged into viral particles (FIG. 2A). The second component is a helper phage M13KO7, which is an M13 phage derivative with the mutation Met40Ile in pII. This helper phage carries an origin of replication from the p15A plasmid and the kanamycin (Kan) resistance gene from Tn903 both inserted within the M13 origin of replication, thus disrupting the M13 origin (FIG. 2B). (Qi, H., Lu, H., Qiu, H.-J., Petrenko, V., and Liu, A. "Phagemid Vectors for Phage Display: Properties, Characteristics and Construction," *J. Mol. Biol.* 417:129-143 (2012).) M13KO7 contains an *E. coli* origin and can replicate; however, in the absence of phagemid DNA, M13KO7 will package the M13KO7 plasmid in produced phage. In the presence of a phagemid bearing a wild-type M13 or f1 origin, single-stranded phagemid is packaged preferentially over helper phage DNA and secreted into the culture medium.

Figure 2C:
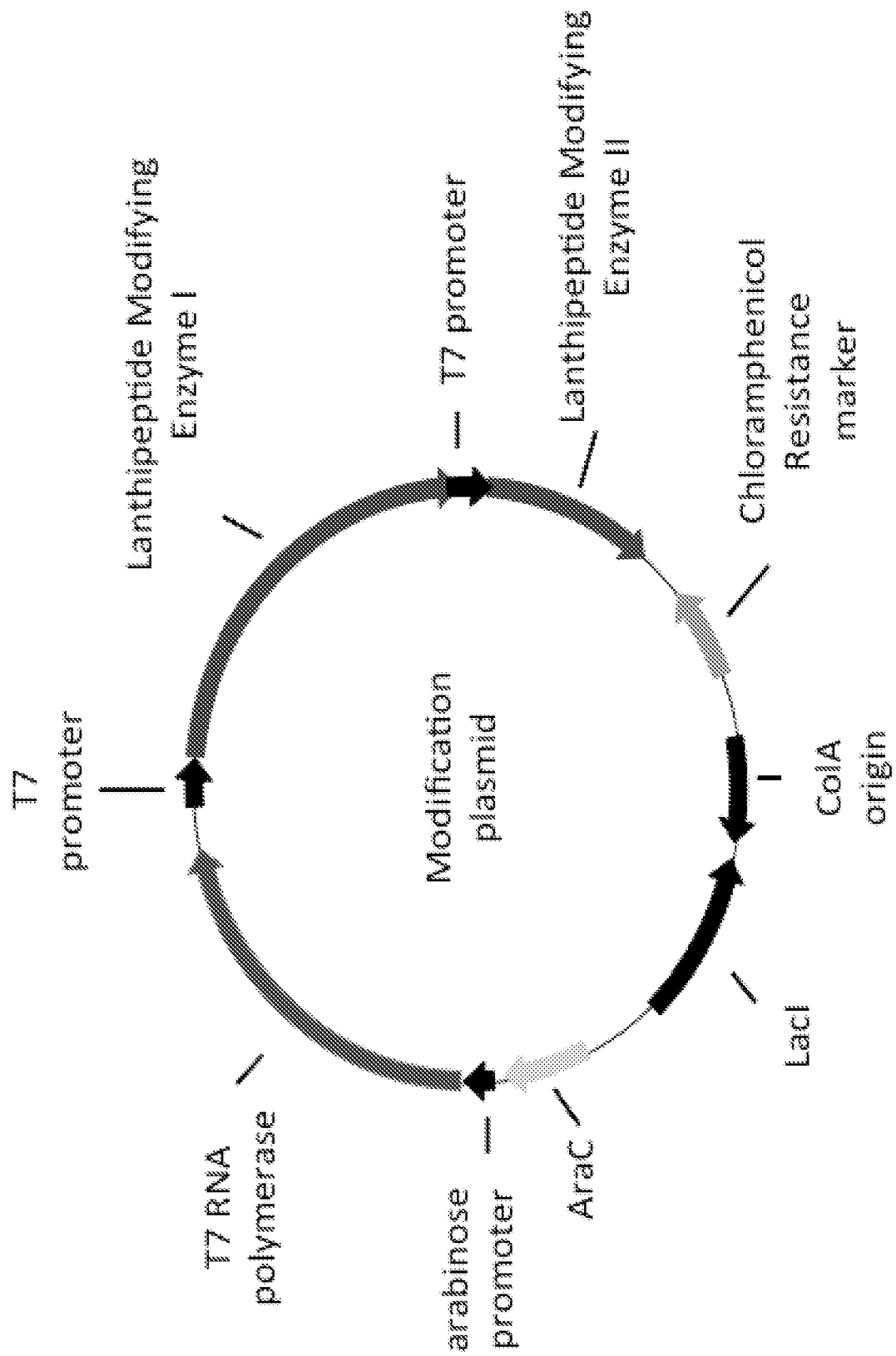
FIG. 2C depicts an exemplary schematic of a modification plasmid that provides biosynthetic genes necessary for modification of the LanA including but not limited to dehydration and thioether crosslink formation.

In phage display, the genetic material for synthesis of the phage structural genes is provided by infection of bacteria (for example E. coli cells), which are harboring a phagemid containing a fusion gene encoding the display peptide fused to a phage surface protein, by the helper phage (FIG. 2C). This approach allows expression of phage proteins and peptide-phage protein fusion in E. coli, which results in the assembly of phage displaying peptide-phage protein on their surfaces. In addition, preferential packaging of the phagemid over helper phage DNA is favored as packaging of wild-type M13 or f1 origin on the phagemid is more efficient than packaging of the helper phage genome due to its distorted phage origin (FIG. 2C).

Peptides can be displayed either fused directly to the N-terminus of truncated pIII via the peptide C-terminus or through fusion on the peptide N-terminus to a presentation peptide, which then hybridizes to the truncated pIII (Sachdev S, S. "Engineering M13 for phage display," Biomol. Eng. 18:57-63 (2001).) An N-terminal display was chosen through direct fusion of the C-terminus of NisA to the truncated pIII. It was believed such a fusion would still allow modification of NisA by NisB and NisC since modification of NisA fused to a membrane anchor protein has been previously reported (Bosma, T., Kuipers, A., Bulten, E., de Vries, L., Rink, R., and Moll, G. N. "Bacterial Display and Screening of Post-translationally ThioetherStabilized Peptides," Appl. Environ. Microb. 77:6794-6801 (2011)). Moreover, such a display would expose the N-terminus of NisA, thereby allowing it to interact with its natural target since the N-terminus of nisin binds to lipid II (Hsu, S. T., Breukink, E , Tischenko, E., Lutters, M. A., De Kruijff, B., Kaptein, R., Bonvin, A. M., and Van Nuland, N. A. "The nisin-lipid II complex reveals a pyrophosphate cage that provides a blueprint for novel antibiotics," Nat. Struct. Mol. Biol. 11:963-967 (2004)). Additionally, it would allow removal of the leader peptide, which could be accomplished either by cleavage from an endogenous protease in E. coli or through incubation of the final construct with a protease, while maintaining modified NisA fused to the phage. Previous studies showed that addition of N-terminal tags such as histidine tags to the lanthipeptide precursor peptides did not prevent the activity of lanthipeptide synthetases. (Chatterjee, C., Paul, M., Xie, L., and van der Donk, W. A. "Biosynthesis and Mode of Action of Lantibiotics," Chem. Rev. 105:633-684 (2005).) Therefore, the modifying enzymes were expected to accept their substrates fused directly to pIII and augmented on the N-terminus with a signal peptide and hexahistidine tag.

Phage propagates at 30° C. instead of 18° C., which is the temperature used for the E. coli coexpression system described for the lantibiotics employed in this study. (Okesli, A., Cooper, L. E., Fogle, E. J., and van der Donk, W.A. "Nine Post-translational Modifications during the Biosynthesis of Cinnamycin," J. Am. Chem. Soc. 133:13753-13760 (2011); Shi, Y., Yang, X., Garg, N., and van der Donk, W.A. "Production of lantipeptides in Escherichia coli," J. Am. Chem. Soc. 133:2338-2341 (2010).) Therefore, one potential concern was incomplete modification of the peptides displayed on phage due to non-functioning enzymes at 30° C. In order to test whether the enzymes can work at 30° C., NisA was coexpressed with NisB and NisC at 30° C. Analysis of the isolated NisA peptide by MALDI-ToF MS showed that the NisA was completely modified demonstrating that this temperature can be successfully employed for nisin production.

Figure 3:
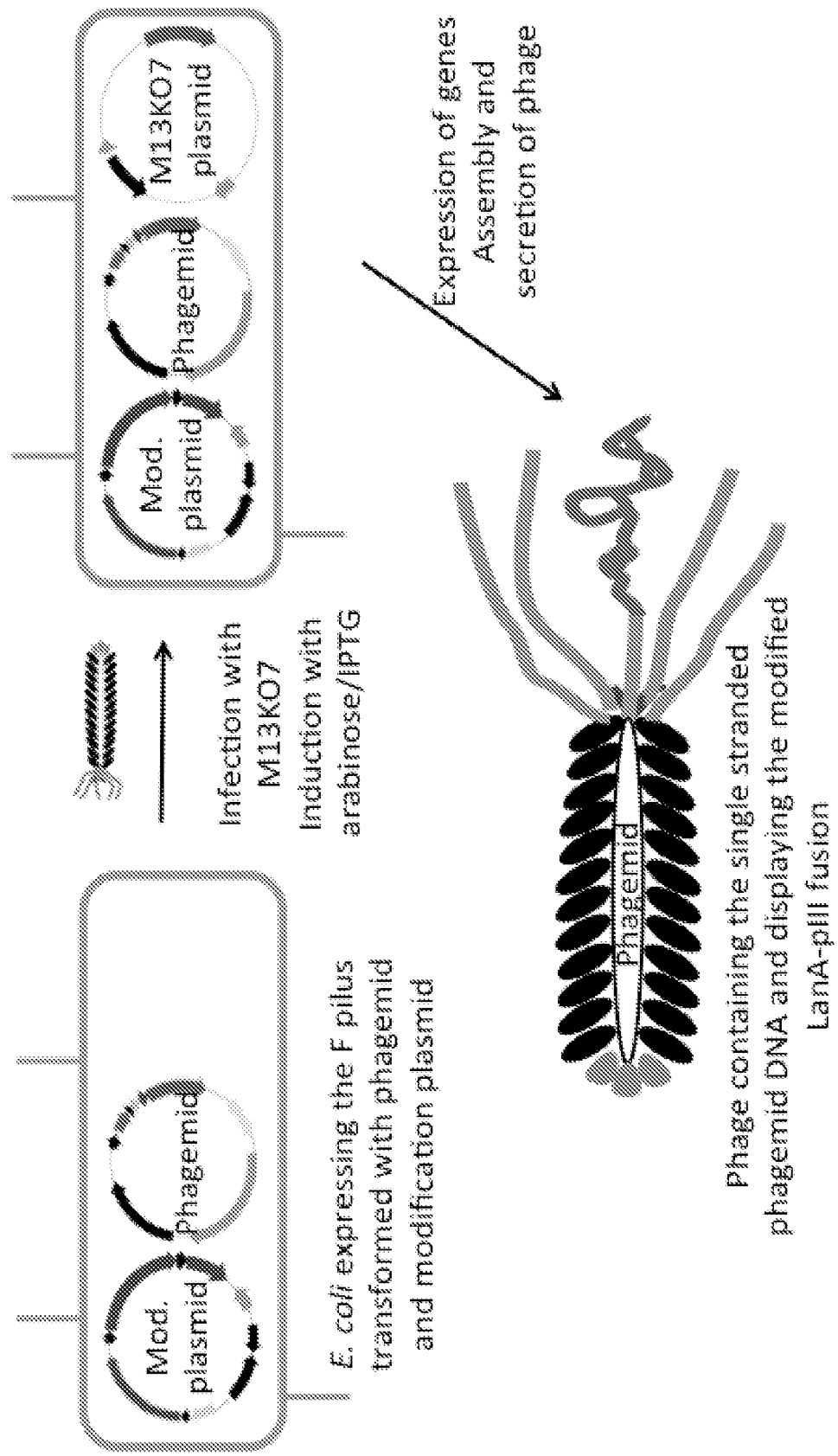
FIG. 3 depicts an exemplary schematic of precursor peptide synthesis, modification, and assembly on phage as well as ensuing phage propagation in M13 phage display via helper phage. The red part in the final drawing represents the posttranslationally modified NisA peptide (for structure see FIG. 1).

FIG. 3 depicts a preferred embodiment of the phage system. The gene encoding the precursor peptide NisA was successfully cloned into the designed phagemid. Modified NisA was displayed on phage by transforming E. coli SS320 with the phagemid and the modification plasmid, then growing the bacteria at 37° C. to $OD_{600nm}$ between 0.3 and 0.5 as the infectivity of the helper phage drops precipitously above $OD_{600nm}$=0.5. Then M13KO7 was added to a multiplicity of infection of approximately 7 to provide the phage structural genes, isopropyl β-D-1-thiogalactopyranoside (IPTG) was added to a final concentration of 0.8 mM to induced expression of the NisA-pIII fusion protein, and arabinose was added to a final concentration of 0.04% w/v to induce expression of T7 polymerase which in turn expressed NisB and NisC. Cells were then allowed to grow for one hour at 37° C. to ensure infection. Kanamycin was then added to kill any uninfected cells and the temperature was reduced to 30° C. to ensure optimal production of phage. The culture was allowed to continue to grow overnight, then the cells were removed by centrifugation. The phage was then isolated from the supernatant of the cell culture via PEG precipitation.

Figure 4A:
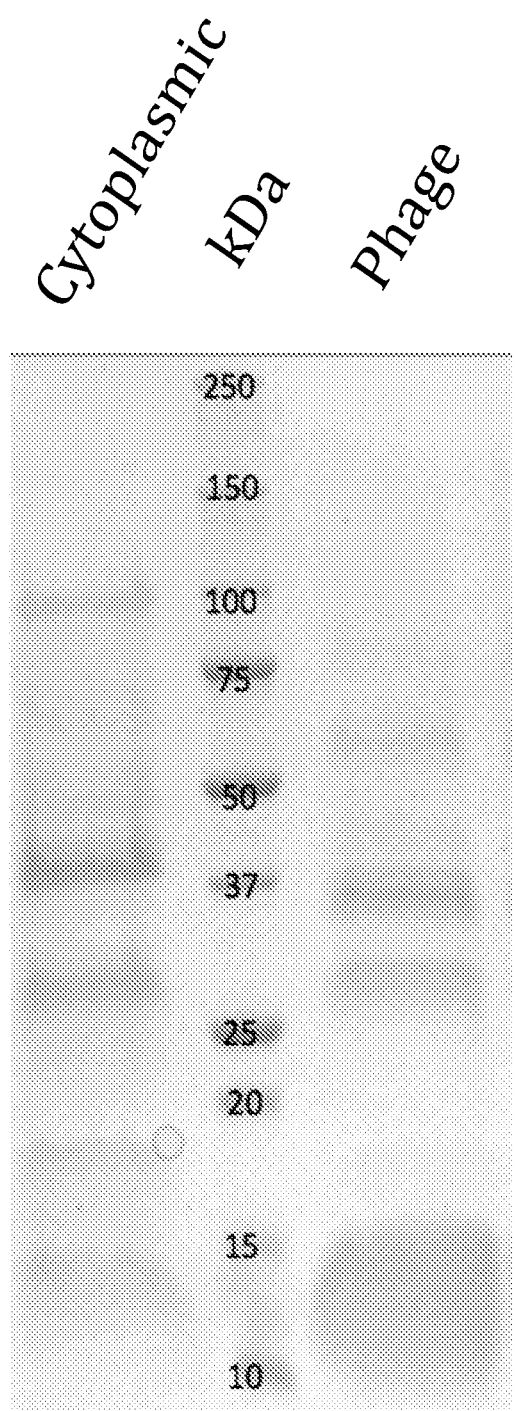
FIG. 4A depicts an exemplary SDS-PAGE analysis of an IMAC-purified cytoplasmic peptide from *E. coli* SS320 expressing the phagemid and the modification plasmid in the lane labeled "cytoplasmic." It also depicts SDS-PAGE analysis of phage created using the scheme outlined above in the lane labeled "phage." In addition to the expected NisA-pIII fusion peptide at ~25 kDa, the purified cytoplasmic fraction contains a band at ~40 kDa that likely corresponds to NisC and a band at ~100 kDa that likely corresponds to NisB. These proteins are frequently co-purified with NisA. In the phage lane, phage coat proteins pVI, pVII, pVIII, and pIX are observed as a smear between 10 and 15 kDa. The NisA-pIII fusion is again observed at ~25 kDa. Note that pIII runs at approximately 60 kDa, consistent with the literature (van Wezenbeek, P. M. G. F., Hulsebos, T. J. M., and Schoenmakers, J. G. G. "Nucleotide sequence of the filamentous bacteriophage M13 DNA genome: comparison with phage fd," *Gene.* 11:129-148 (1980)).

As the NisA-pIII fusion protein represents an exceedingly small portion of the total phage proteins isolated, the phage was resolved into its component proteins by SDS-PAGE prior to mass spectrometry analysis. Phage was denatured by boiling in Laemmli buffer for 5 minutes, and the denatured phage proteins were loaded onto a 4-20% Tris-glycine gel and separated by SDS-PAGE. Comparison of the bands separated via SDS-PAGE to a ladder of proteins of known molecular weight showed that both wild type pIII and the NisA-pIII fusion peptide were expressed and present on the phage (FIG. 4A). Additionally, comparison of the NisA-pIII fusion peptide to that isolated from the cytoplasm of a cell expressing the phagemid and modification plasmid but not infected with helper phage provided additional verification that the observed protein was indeed the expected fusion of NisA-pIII.

Figure 4B:
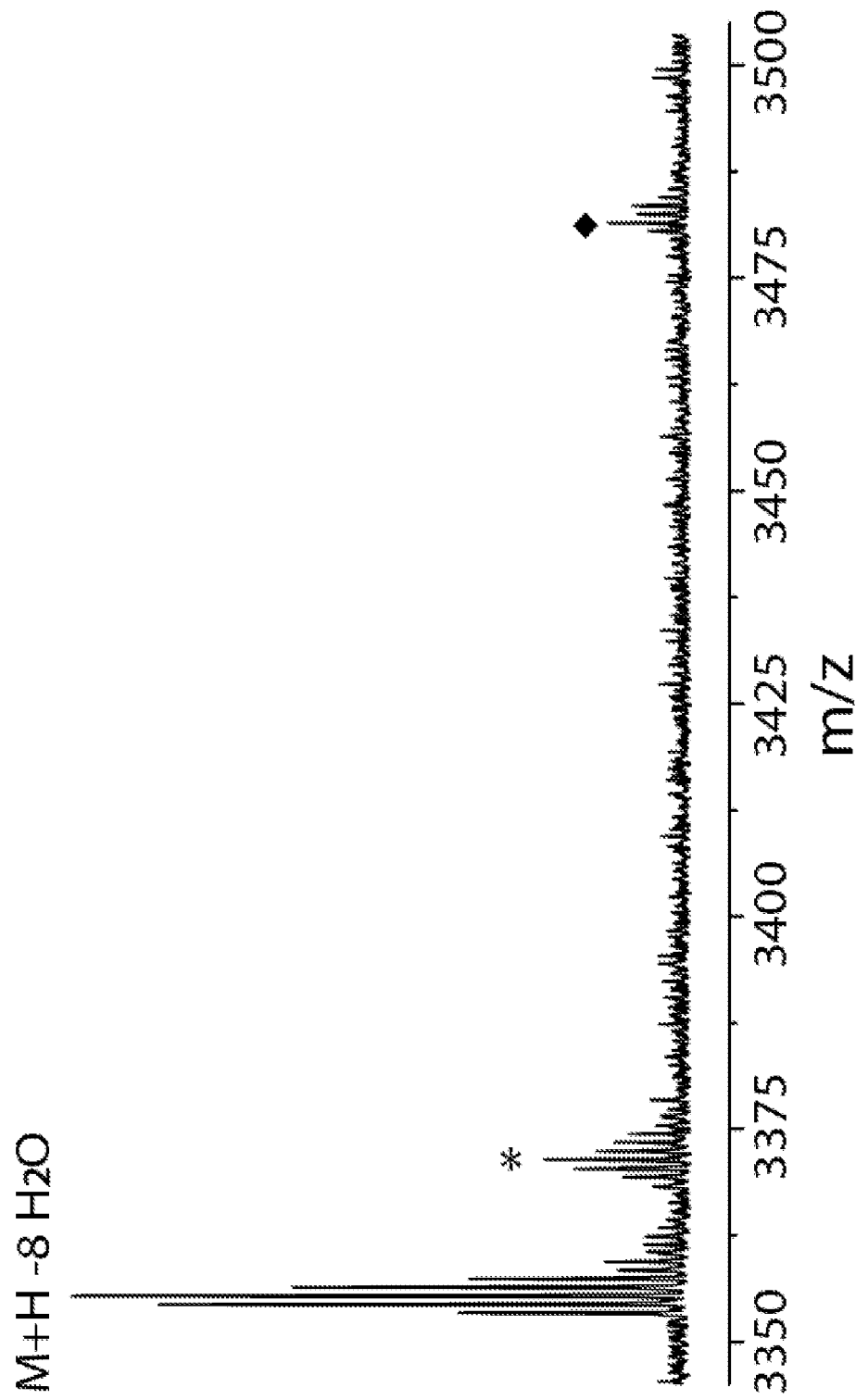
FIG. 4B depicts an exemplary MALDI-TOF-MS spectrum of modified NisA displayed on phage. The modified NisA was extracted from an excised, trypsin-digested SDS-PAGE gel fragment corresponding to NisA-pIII fusion. Expected mass of NisA [M+H-8H$_2$O] 3352.5 Da. Observed mass 3353.4 Da. The peak marked with * is an oxidation peak [M+H-8H$_2$O+16]. The peak marked with ♦ may represent a single dehydration of NisA or may be a trypsin-related peak.

In order to verify that the dehydration modification had indeed occurred, the band corresponding to the NisA-pIII fusion on phage was excised from the polyacrylamide gel. The excised gel slice was then digested with trypsin and the tryptic peptides extracted using a protocol adapted from the literature (Lavigne, R., Ceyssens, P.-J., Robben, J., "Phage Proteomics: Applications of Mass Spectrometry." In: Clokie, M. R. J., and Kropinski, A. M. (Eds.), Bacteriohpages: Methods and Protocols, Volume 2: Molecular and Applied Aspects, vol. 502. Humana Press, New York, N.Y., 2009, pp. 239-254). The excised slice was analyzed via MALDI-TOF-MS and contained a fragment corresponding to fully dehydrated NisA (FIG. 4B). Trypsin does not cut inside fully modified nisin (FIG. 4C).

SecA accepts unfolded proteins and threads them through the transmembrane channel and is known to not accept molecules larger than 2.8 nm. (Bonardi, F., Halza, E., Walko, M., Du Plessis, F., Nouwen, N., Feringa, B. L., and Driessen, A. J. M. "Probing the SecYEG translocation pore size with preproteins conjugated with sizable rigid spherical molecules," P. Natl. Acad. Sci. 108:7775-7780 (2011).) On the other hand the twin-arginine transport (tat) pathway, another major export pathway in E. coli, is known to transport large molecules such as proteins which are only fully-folded in the cytoplasm (Berks, B., Sargent, F., and Palmer, T. "The Tat protein export pathway," Mol Microbiol 35:260-274 (2000)), allowing more time in the cytoplasm before the export. (Thomas, J. D., Daniel, R. A., Errington, J., and Robinson, C. "Export of active green fluorescent protein to the periplasm by the twin-arginine translocase (Tat) pathway in Escherichia coli," Mol. Microbiol. 39:47-53 (2001).)

Therefore, in order to display fully-modified nisin on phage, we focused on transporting nisin via twin arginine transport (tat)-pathway. This would increase the contact time between NisA and the enzymes NisB and NisC before the export into the periplasm, and help the formation of fully-modified nisin before the export.

Figure 4D:
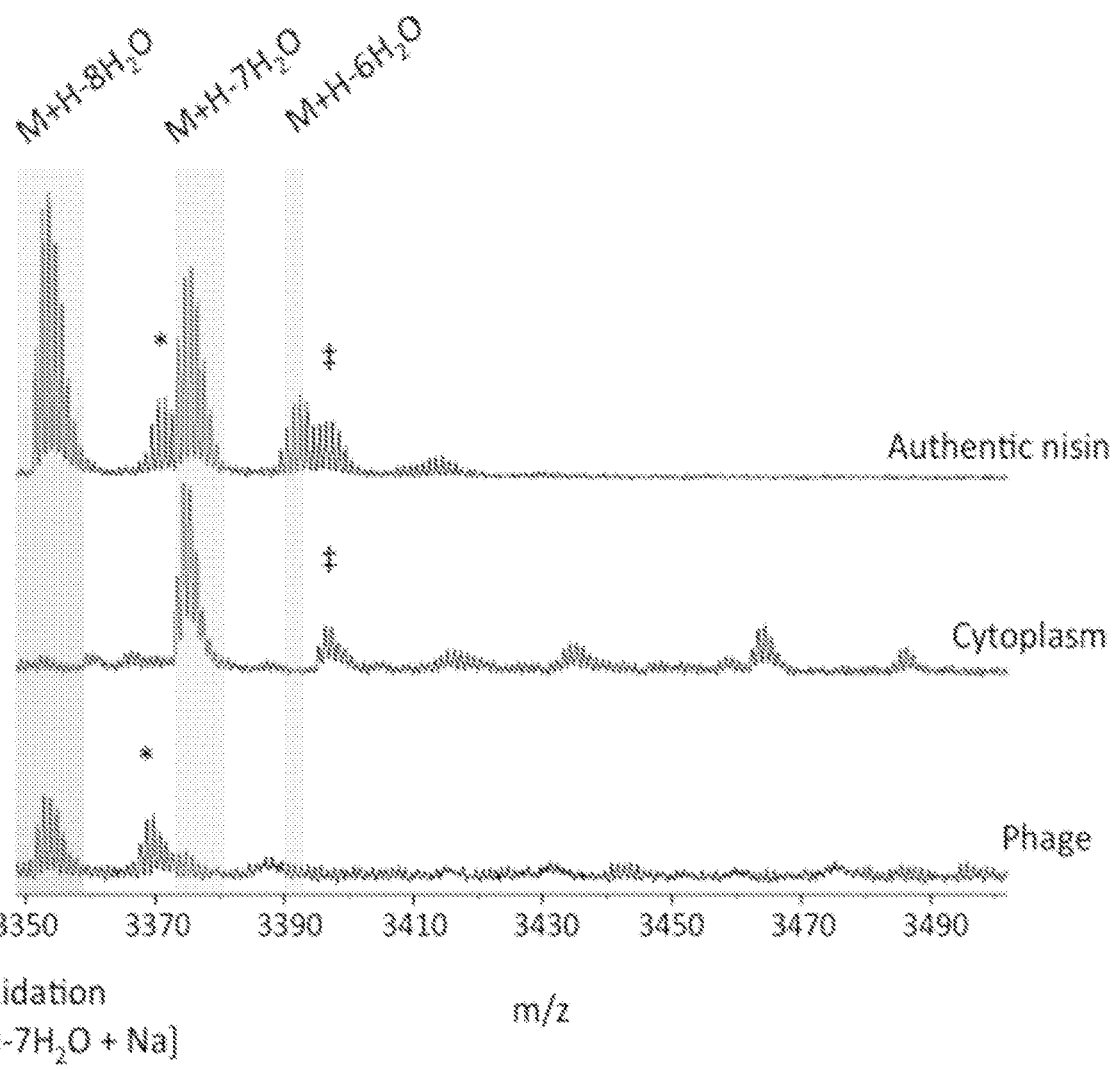
FIG. 4D depicts a comparison of exemplary MALDI-MS spectra of authentic nisin containing fully and partially dehydrated nisin, trypsin-digested nisin intermediates purified from the cytoplasmic portion of *E. coli* SS320 expressing the phagemid and the modification plasmid, and modified NisA extracted from an excised, trypsin-digested SDS-PAGE gel fragment corresponding to NisA-pIII fusion displayed on phage.

As a comparison to the peptide displayed on phage, E. coli SS320 was transformed with the phagemid and the modification plasmid. The bacterial culture was then grown at 37° C. to $OD_{600nm}$ between 0.3 and 0.5, after which isopropyl β-D-1-thiogalactopyranoside (IPTG) was added to a final concentration of 0.8 mM to induce expression of the NisA-pIII fusion protein, and arabinose was added to a final concentration of 0.04% w/v to induce expression of T7 polymerase which in turn expressed NisB and NisC. Cells were then allowed to grow overnight at 30° C. Then the cells were pelleted by centrifugation. The cells were resuspended in denaturing buffer (8M urea, 100 mM Tris-Cl, pH 8.0) and lysed by freezing at −80° C. and thawing. The lysate was clarified by centrifugation and then loaded onto Ni-NTA resin. The resin was washed with wash buffer (8M urea, 100 mM Tris-Cl, pH 6.3) and eluted in elution buffer (8M urea, 100 mM Tris-Cl, pH 4.5). The resulting eluent was diluted, digested with trypsin, and analyzed with MALDI-MS. Surprisingly, the analysis revealed a trypsin fragment, which corresponds to 7-fold dehydrated NisA rather than the full 8-fold dehydrated peptide, which was observed on the phage (FIG. 4D). The build up of 7-fold dehydrated NisA inside the E. coli cells but not on the phage suggests that the 7-fold dehydrated NisA is not readily exported via the Tat pathway. The absence of 8-fold dehydrated NisA inside the E. coli cells suggests that the fully dehydrated species is readily exported via the Tat pathway and hence not observed in the cytoplasmic fraction.

Figure 5A:
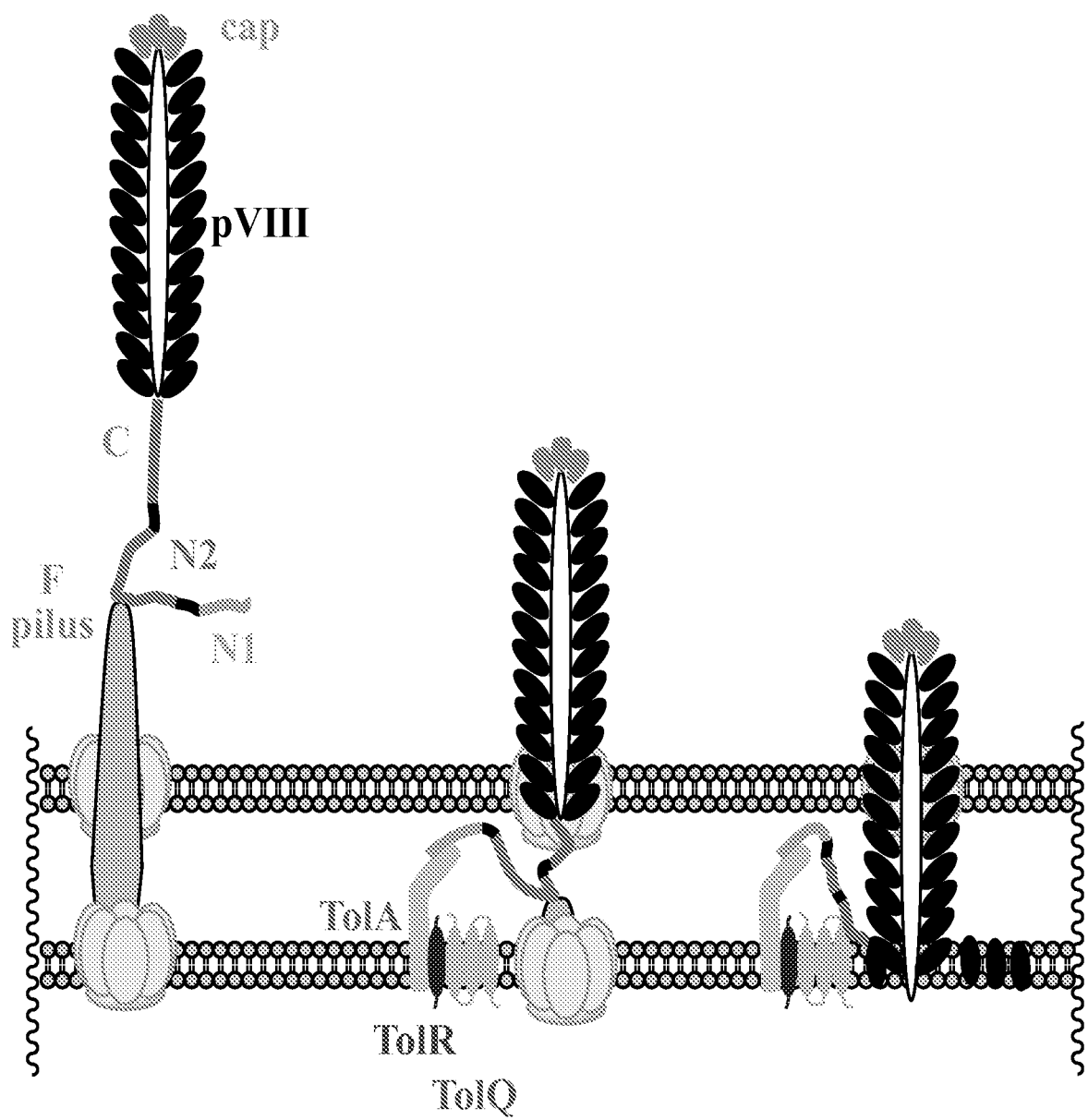
FIG. 5A depicts the process in which wild type M13 phage infects the Gram-negative bacteria *E. coli* that display the F pilus, adapted from Bennett, N. J.; Gagic, D.; Sutherland-Smith, A. J.; Rakonjac, J., "Characterization of a dual-function domain that mediates membrane insertion and excision of Ff filamentous bacteriophage," J. *Mol. Biol.* 411, 972-985 (2011).
Figure 5B:
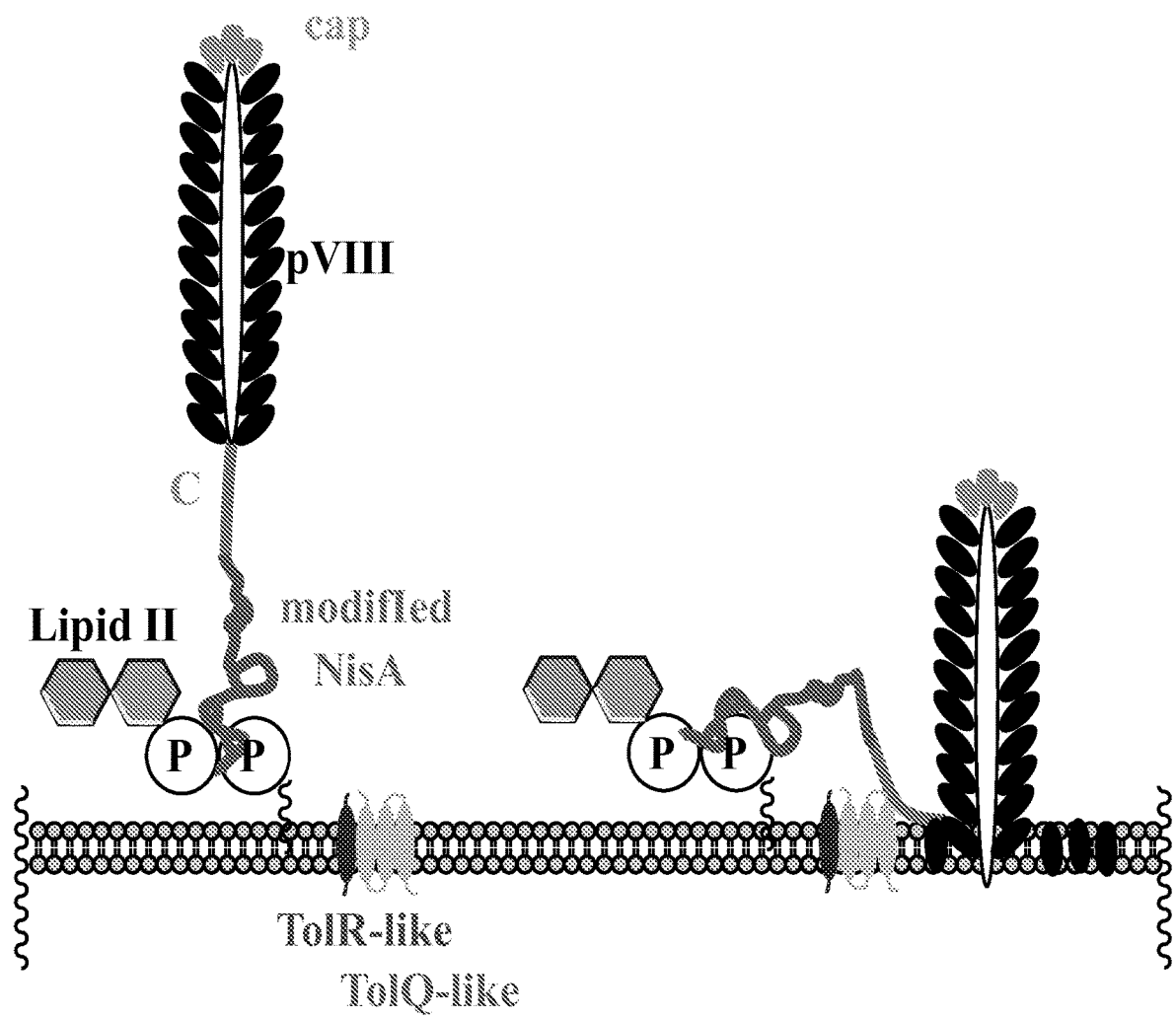
FIG. 5B depicts the proposed process in which phage displaying modified NisA may infect Gram-positive bacteria, leveraging the affinity of modified NisA for the diphosphate moiety of lipid II as a primary receptor in lieu of the F pilus.
Figure 5C:
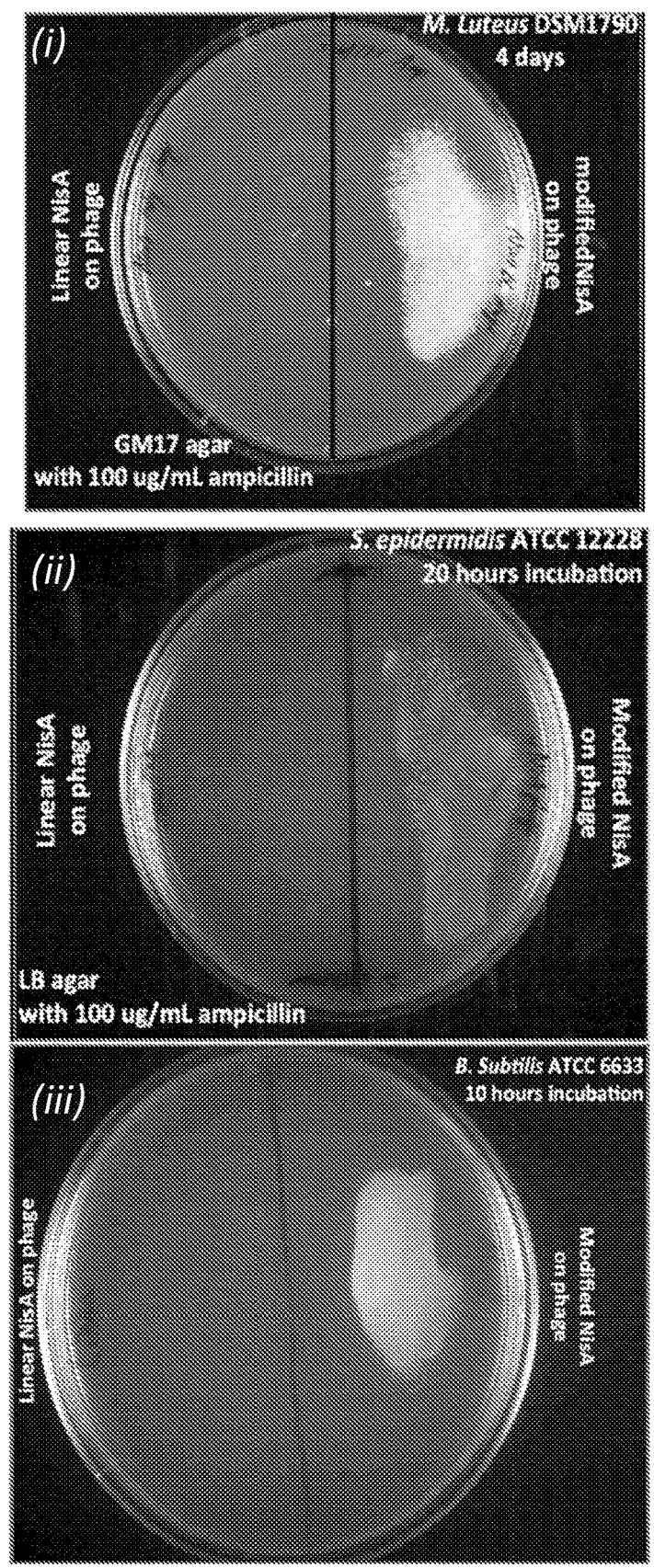
FIG. 5C depicts exemplary culture plates of *Micrococcus luteus* DSM1790, *Staphylococcus epidermidis* ATCC12228, and *Bacillus subtilis* ATCC 6633 infected with either phage displaying modified NisA or phage displaying unmodified (linear) NisA. The bacteria are grown on plates containing the antibiotic ampicillin, to which all three strains are sensitive. As the phage produced using the coexpression system designed above packages the phagemid which contains a beta lactamase gene, successful infection by the phage endows the bacteria with ampicillin resistance.

In wild type M13 bacteriophage, the N-terminal domains of pIII (denoted "N1" and "N2") recognize the TolA and F pilus receptors, respectively, and after engaging these secondary and primary receptors the C-terminal portion of pIII interacts with either the TolQ or TolR protein to insert into the inner membrane of E. coli and inject the DNA (FIG. 5A). Based on the known affinity of nisin for the diphosphate moiety of lipid II, it was believed that phage displaying modified NisA may be capable of infecting Gram-positive bacteria by using the diphosphate of lipid II as the primary receptor site and then allowing the C-terminal portion of pIII to mediate infection through the conserved TolQ/TolR proteins (FIG. 5B). Successful infection of bacteria by the phage would transfer the phagemid including its ampicillin resistance gene into the infected bacteria. Expression of this gene would lead to resistance in the bacteria against ampicillin. Phage was made as above then incubated with bacteria in exponential phase growth for 30 minutes to 1 hour. The bacteria were then pelleted, resuspended in a minimal amount of media, and spread on one half of an agar plate containing ampicillin (FIG. 5C). As a negative control, the modification plasmid was not transformed into the system and phage was thus made displaying the linear NisA-pIII peptide only. These cells were plated on the second half of the plate. Results indicated that the phage displaying modified NisA and not the phage displaying linear NisA was capable of infecting bacteria (FIG. 5C).

These results suggest that the posttranslational modifications to NisA are necessary for the infectivity of the phage, consistent with the interaction between lipid II and nisin displayed on phage mediating the transformation. Furthermore, a minimal biocontainment advantage is afforded by the system. Since the NisB and NisC genes are not on the phagemid that is packaged in the phage, any NisA produced in phage generations post nisin-mediated infection of a host would be in the linear form and unable to interact with its target, thus eliminating the general nisin-mediated infectivity. Non-infectivity is also ensured by the absence of phage genes on the phagemid.

Figure 5D:
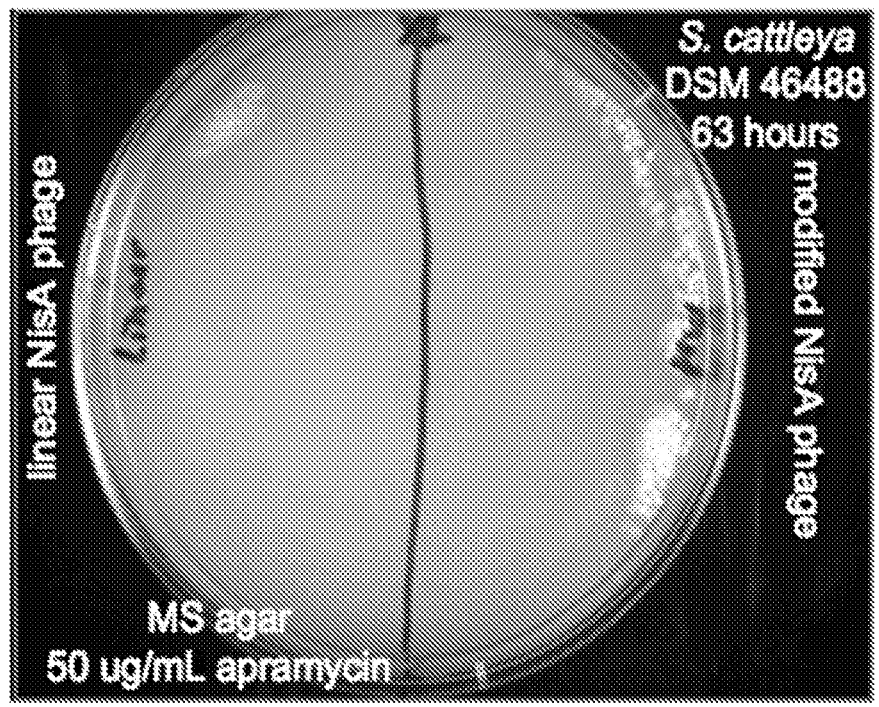
FIG. 5D depicts an exemplary culture plate of *Streptomyces cattleya* DSM46488. As the genus *Streptomyces* is naturally resistant to ampicillin, the phagemid construct here was augmented to include a *Streptomyces* origin pSG5 as well as an apramycin resistance cassette.

In order to broaden the range of bacteria which could be infected by the phage, the phagemid was augmented with the pSG5 origin and apramycin resistance cassette from the pCRISPomyces-2 plasmid (Cobb, R.E., Wang, Y., Zhao, H., "High-Efficiency Multiplex Genome Editing of Streptomyces Species Using an Engineered CRISPR/Cas System," ACS Synth. Biol., 4 (6), 723-728 (2015). Using procedures similar to those described above, phage was produced both with and without expression of the modification plasmid in order to generate phage displaying modified NisA and linear NisA respectively. Streptomyces cattleya DSM46488 was then incubated for 6 to 12 hours with the indicated phage and plated on selective media. The result again confirmed that the phage displaying the modified NisA was significantly more infective than the phage displaying the linear NisA (FIG. 5D).

Figure 5E:
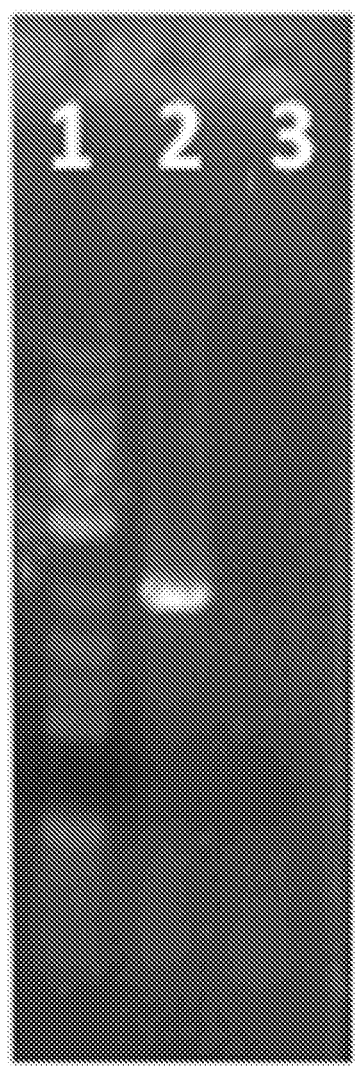
FIG. 5E depicts a 1% agarose electrophoresis gel amplifying the NisA through beta lactamase portion of the phagemid out of the *Bacillus subtilis* ATCC 6633 transformed by the phage system described above indicating successful transformation; lane key: 1, 2 log DNA ladder markers 2, phage-transformed *B. subtilis*; 3, non-transformed *B. subtilis*.

To demonstrate that the phagemid DNA was indeed transferred into the bacteria, a sample of B. subtilis ATCC6633 transformed by the phage displaying NisBC-modified NisA was grown overnight in a liquid culture of LB with 25 μg/mL ampicillin. A separate culture of B. subtilis ATCC6633 which was not incubated with phage was also grown overnight. A PCR reaction was then performed which amplified the phagemid DNA sequence from the start of the NisA gene to the end of the beta lactamase gene. Both of these cultures of B. subtilis ATCC6633 were used as a template in separate PCR reactions. A 2 kbp fragment was only amplified from the culture of B. subtilis ATCC6633 transformed with the phage (FIG. 5E). This suggests that the phagemid DNA is indeed delivered into the bacteria and is responsible for the resistance.

Figure 6:
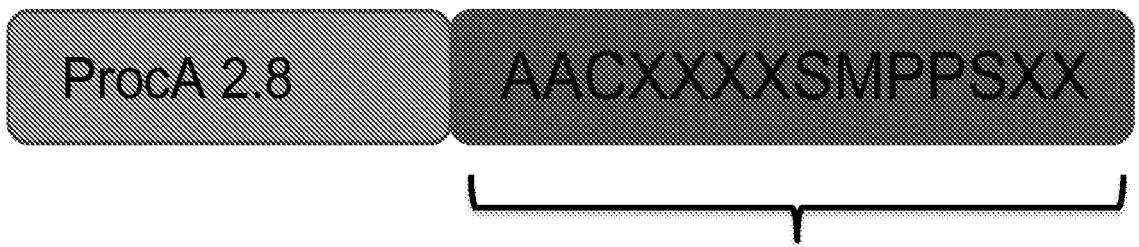
FIG. 6 depicts an exemplary peptide design for cyclic peptides containing a double ring structure in which a ProcA2.8 leader peptide was attached to a core region to lead to the formation of two rings.

Phage display libraries can be designed for use of the highly promiscuous enzyme ProcM. This enzyme has 30 natural substrates composed of a highly conserved leader domain attached to highly diverse core regions containing serines/threonines and cysteines at different positions. (Li, B., Sher, D., Kelly, L., Shi, Y., Huang K., Knerr P. J., Joewono I., Rusch D. Chisholm, S. W., and van der Donk, W. A. (2010) "Catalytic promiscuity in the biosynthesis of cyclic peptide secondary metabolites in planktonic marine cyanobacteria," Proc. Natl. Acad. Sci., USA 107:10430-10435 (2010) Zhang, Q., Yang, X., Wang, H., van der Donk, W. A. (2014) "High divergence of the precursor peptides in combinatorial lanthipeptide biosynthesis" ACS Chem. Biol. 2686-2694.) Therefore, ProcM was considered a good candidate for constructing a library of peptides containing two lanthionine crosslinks (FIG. 6).

The peptides in the library consisted of the ProcA2.8 wild type leader sequence attached to a core region coding for $C(X)_5SMPPS(X)_5C$ (SEQ ID NO.: 9), where X is an amino acid encoded by the NWY degenerate codon. The peptides were encoded in a pRSFDuet-1 vector containing the gene encoding for ProcM. The NWY codon was selected for the library because it does not encode for Cys or Ser/Thr, and therefore would not complicate lanthionine formation at the designed positions. Twenty clones were investigated as shown in Table 1.

TABLE 1

Randomized peptides possessing the ProcA 2.8 wild type leader peptide attached to a core region with the sequence C(X)₅SMPPS(X)₅C (SEQ ID NO.: 9).

| ID [SEQ ID NO.:_] | Core peptide sequence | Major dehydrations by MS | IAA/NEM alkylation | Conclusion |
|---|---|---|---|---|
| Library 2A | | | | |
| 2.8-1 [SEQ ID NO.: 10] | AACFNVHISMPPSHNNVHC | -2 H₂O | No IAA adduct | 2 rings |
| 2.8-2 [SEQ ID NO.: 11] | AACDVNLHSMPPSLDFFVC | -2 H₂O | No IAA adduct | 2 rings |
| 2.8-3 [SEQ ID NO.: 12] | AACVFHFDSMPPSYLDDDC | -2 H₂O | No IAA adduct | 2 rings |
| 2.8-4 [SEQ ID NO.: 13] | AACNIDFLSMPPSIHHILC | -2 H₂O | No NEM adduct | 2 rings |
| 2.8-5 [SEQ ID NO.: 14] | AACNIYYISMPPSHHFVYC | -2 H₂O | No NEM adduct | 2 rings |
| 2.8-6 [SEQ ID NO.: 15] | AACHDNNNSMPPSFYHIFC | -2 H₂O | No NEM adduct | 2 rings |
| 2.8-7 [SEQ ID NO.: 16] | AACHLNYNSMPPSFHILFC | -2 H₂O | No NEM adduct | 2 rings |
| 2.8-8 [SEQ ID NO.: 17] | AACLNNLVSMPPSNIVVYC | -2 H₂O | No NEM adduct | 2 rings |
| 2.8-9 [SEQ ID NO.: 18] | AACNIHIYSMPPSNNHFNC | -2 H₂O | No NEM adduct | 2 rings |
| 2.8-10 [SEQ ID NO.: 19] | AACHDINLSMPPSFLNVIC | -2 H₂O | No NEM adduct | 2 rings |
| 2.8-11 [SEQ ID NO.: 20] | AACILYLISMPPSNIFNDC | -2 H₂O | No NEM adduct | 2 rings |
| 2.8-12 [SEQ ID NO.: 21] | AACFFDINSMPPSDDLYLC | -2 H₂O | No NEM adduct | 2 rings |
| 2.8-13 [SEQ ID NO.: 22] | AACLIVDYSMPPSIDNHLC | -2 H₂O | No NEM adduct | 2 rings |
| 2.8-14 [SEQ ID NO.: 23] | AACHINRISMPPSDIVDFC | -2 H₂O | No NEM adduct | 2 rings |
| 2.8-15 [SEQ ID NO.: 24] | AACHHNNLSMPPSDYFVLC | -2 H₂O | No NEM adduct | 2 rings |
| 2.8-16 [SEQ ID NO.: 25] | AACNDNNISMPPSIVFDFC | -2 H₂O | No NEM adduct | 2 rings |
| 2.8-17 [SEQ ID NO.: 26] | AACIVNYHSMPPSLNILYC | -2 H₂O | No NEM adduct | 2 rings |
| 2.8-18 [SEQ ID NO.: 27] | AACHLHILSMPPSVYIFLC | -2 H₂O | No NEM adduct | 2 rings |
| 2.8-19 [SEQ ID NO.: 28] | AACNFLVDSMPPSLFVIIC | -2 H₂O | No NEM adduct | 2 rings |
| peptide 3-3 [SEQ ID NO.: 29] | AACLHFFLSMPPSHVLDIC | -2 H₂O | No NEM adduct | 2 rings |

¹The peptides shown were tested for dehydration and cyclization. See also Table 7 for more examples that were tested for dehydration and cyclization.

Peptides 2.8-5, 2.8-9, and 2.8-10 were coexpressed with ProcM and purified by IMAC followed by RP-HPLC. The analysis of the peptides by MALDI-ToF tandem mass spectrometry after GluC endoproteinase cleavage showed that ProcM dehydrated and cyclized all three peptides (FIG. 7A-F).

Previous attempts to produce nisin using export via sec-pathway in its producing strain *Lactococcus lactis* and in *B. subtilis* failed to isolate any bioactive material although fully-dehydrated NisA peptide was obtained from this system. (Kuipers, A., Wierenga, J., Rink, R., Kluskens, L. D., Driessen, A. J. M., Kuipers, O. P., and Moll, G. N. "Sec-Mediated Transport of Posttranslationally Dehydrated Peptides in Lactococcus lactis," *Applied and Environmental Microbiology* 72:7626-7633 ((2006).) In another study however, sec-pathway in *E. coli* was shown to export post-translationally biotinylated and phosphopantetheinylated recombinant proteins successfully, suggesting that sec-transport mechanism can carry post-translationally modified molecules across the membrane. (Chen, N., Hong, F. L., Wang, H. H., Yuan, Q. H., Ma, W. Y., Gao, X. N., Shi, R., Zhang, R. J., Sun, C. S., and Wang, S. B. "Modified Recombinant Proteins Can Be Exported via the Sec Pathway in *Escherichia coli*," *PLoS ONE* 7:e42519 (2012).)

Phage display of lanthipeptides can enable the preparation of thioether-containing cyclic peptide libraries to advance or alter current properties of lantibiotics and/or to select for binders to new targets. Phage display of nisin may be useful for finding binders to molecules with structures similar to the pyrophosphate on lipid II and/or to solve nisin's instability problem at physiological conditions by forming phage libraries displaying nisin-like peptides. To this end the inventors have successfully produced prochlorosins, cinnamycin, haloduracin, and lacticin 481 in *E. coli* and the processing enzymes have been shown to have high tolerance for different substrates. Especially ProcM, the lanthionine synthetase of prochlorosins, may be very valuable to prepare lanthionine-containing peptide libraries as it can naturally process 30 substrates with rings that vary in size and place. (Tang, W., and van der Donk, W. A. "Structural Characterization of Four Prochlorosins: A Novel Class of Lantipeptides Produced by Planktonic Marine Cyanobacteria," *Bio-* chemistry 51:4271-4279 (2012); Li, B. et al. (2010). Zhang, Q. et al. (2014)). In addition, as described above, ProcM successfully processed all 20 non-natural ProcA analogs tested. Therefore, this method can be expanded for phage display of other lanthipeptides, which would enable preparation of cyclic peptide libraries with thioether crosslinks providing different scaffolds.

Yeast Surface Display of Lanthipeptides

In another aspect, a platform for lanthipeptide expression by yeast surface display is provided. As lanthipeptides are genetically encoded, they lend themselves to the facile production of libraries through combinatorial DNA synthesis. The high throughput nature of yeast display and fluorescent activated cell sorting (FACS) in conjunction with the lanthipeptide biosynthetic machinery can provide for the directed evolution of new lanthipeptides that can disrupt specific protein-protein interactions.

Two obstacles must be overcome for the robust utilization of this technique. First, a system must be developed to install post-translational modifications in the peptides prior to their export and anchoring to the cell surface. Second, one must determine an appropriate scaffold or scaffolds to generate these cyclic peptide libraries (FIG. 8). The inventors have focused on a well-established method of yeast display where the protein of interest is fused to a subunit of the yeast mating protein, agglutinin. (Boder, E. T.; Wittrup, K. D. "Yeast surface display for screening combinatorial polypeptide libraries," *Nat Biotechnol* 15:553-7 (1997).) Agglutinin is a heterodimer with the two subunits covalently linked through two disulfide bridges. One subunit, Aga1, is covalently anchored to the cell wall and the other subunit, Aga2, is anchored to it via the disulfide linkages. Fusions can be made on the N-terminus or C-terminus of Aga2 for display. This system in conjunction with fluorescence-activated cell sorting (FACS) has been used successfully for the directed evolution of bioreceptors such as antibodies (Boder, E. T.; Midelfort, K. S.; Wittrup, K. D., "Directed evolution of antibody fragments with monovalent femtomolar antigen-binding affinity," *Proc Natl Acad Sci USA* 2000, 97:10701-5 (2000)) and T cell receptors (Kieke, M. C.; Shusta, E. V.; Boder, E. T.; Teyton, L.; Wittrup, K. D.; Kranz, D. M., "Selection of functional T cell receptor mutants from a yeast surface-display library," *Proc Natl Acad Sci USA* 96:5651-6 (1999)). This system is being used to display the well-characterized lanthipeptides lacticin 481, prochlorosin 2.8, and haloduracin β on the surface of yeast cells. By tuning the subcellular localization of the modifying enzymes, the timing of expression of these modifying enzymes and their substrate peptides, and their overall expression levels, fully modified lanthipeptides can be produced as determined by comparison to authentic standards. Our initial approach to library construction is to use the prochlorosins 1.1 and 2.8 as scaffolds as these have been shown to be robust and amenable to library generation. Libraries can be generated through degenerate DNA synthesis to encode for randomized amino acids within their native rings and between their rings, as well as insertions or deletions within their native rings and between their rings. Peptides from these libraries will be examined for their extent of cyclization and their ability to bind fluorescently labeled proteins or small molecules like lipid II will be determined using FACS.

Synthetic genes codon optimized for expression in *S. cerevisiae* encoding LanAs and LanMs have been produced for each system. Both N-terminal (FIG. 9A) and C-terminal (FIG. 9B) Aga2 fusions were tested for anchoring the LanA to the cell surface. The genes encoding LanMs contain an N-terminal secretion signal as well as a C-terminal endoplasmic reticulum (ER) retention signal (FIG. 9C). To determine whether the LanA-Aga2 fusion proteins are still a substrate for a LanM, the construct N-terminal anchoring of lacticin 481, Aga2-LctA, prochlorosin 2.8, Aga2-ProcA 2.8, and haloduracin β, Aga2-HalA2, and C-terminal anchoring of lacticin 481, LctA-Aga2, were cloned into *E. coli* expression plasmids and coexpressed with the cognate LanM, LctM, ProcM, and HalM2, respectively. After purification by immobilized metal affinity chromatography (IMAC), digestion by the appropriate proteases, trypsin for Aga2-LctA, Glu-C for Aga2-ProcA 2.8 and Aga2-HalA2, and trypsin and Glu-C for LctA-Aga2, and further purification by reverse phase chromatography, the LanA core peptides were examined my matrix-assisted laser desorption/ionization time of flight mass spectrometry (MALDI-TOF MS) to determine the extent of dehydration. All peptides exhibited masses corresponding to the expected number of dehydrations from the respective wild type lanthipeptides (FIG. 10A-E); the Aga2-LctA construct also exhibited a species corresponding to 5 dehydrations. Treatment with N-ethylmaleimide (NEM), which will react with cysteines not involved in thioether crosslinks, showed no changes in mass for the Aga2-LanA core peptides and a small amount of a single NEM adduct for the LctA-Aga2 core peptide (FIG. 10), indicating the core peptides are being cyclized as well as dehydrated.

With evidence of successful dehydration and cyclization in hand we proceeded to construct *S. cerevisiae* expression vectors for Aga2-LctA, Aga2-ProcA 2.8, Aga2-HalA2, and LctA-Aga2 with and without the respective LanM coexpression. After induction of expression, the yeast cells were assayed for the presence of surface displayed LanA by FACS based on detecting the HA epitope or Strep-Tag II. The presence of displayed protein was detected for all constructs (FIG. 11A-F). Aga2-HalA2 was then freed from the surface of the yeast by treatment with tris(2-carboxyethyl)phosphine (TCEP), enriched by streptactin chromatography, digested with Glu-C and analyzed by MALDI-TOF MS. A mass corresponding to the 7-fold dehydrated core peptide could be observed FIG. 11F), indicating dehydrated Aga2-HalA2 is being displayed on the yeast surface. Treatment with iodoacetamide (IAA), which will react with cysteines not involved in thioether crosslinks, showed no change in mass, suggesting Aga2-HalA2 displayed on the yeast surface is fully cyclized as well. These studies demonstrate the feasibility of displaying lanthipeptides on the surface of yeast cells to be used for the directed evolution of lanthipeptides capable of binding novel targets.

Clinical Applications

In addition to its potential as an agent for the transformation of bacteria in a laboratory setting, such infectious phage could be leveraged in a clinical setting as a novel means of bacteriophage therapy. Current strategies for bacteriophage therapies primarily leverage lytic phage to lyse the infectious bacteria. Such strategies share many liabilities, including the potential to induce septic shock in the patient by the rapid lysis and release of virulence factors from many bacteria, the uncertain concentration of the phage in the body following the initial dosing since the lytic phage uses its host bacteria to replicate, the narrow range of bacteria on which a given lytic phage can act due to its receptor specificity, and the rapid development of resistance to the phage (Labrie, S. J., Samson, J. E., Moineau, S., "Bacteriophage Resistance Mechanisms," *Nat. Rev. Microbiol.* 8: 317-327 (2010)). Filamentous phage displaying modified NisA overcomes many of these natural limitations of lytic phage. Since a filamentous phage can be engineered to introduce any desired gene into bacteria that it can infect, the filamentous phage can avoid the potential of wholesale lysis and release of infectious proteins by introducing a gene deletion system to target a specific virulence factor or a key metabolic pathway of a single species of bacteria. Such a phage would also introduce less stringent selective pressure for bacterial variants that could avoid phage infection since the phage would render the bacteria less harmful rather than kill it. Additionally, documented nisin resistance among Gram-positive bacteria is remarkably low and the phage leverages a nisin or nisin-like moiety for infection. Thus, a low incidence of resistance is expected despite the phage having a wide range of infectivity among Gram-positive bacteria. This offers the additional benefit to circumvent the clinical diagnosis challenge of determining which phage will effectively infect the pathogenic bacteria prior to treatment. Moreover, as the modified NisA-displaying phage is unable to replicate, the amount of phage dosed is the amount of phage present in the patient and biocontainment is assured.

In view of the foregoing, platforms, phage, phagemid, systems and methods are provided for identifying engineered lanthipeptide display peptides expressed in vivo from biological organisms.

In a first aspect, a platform for bacterial phage display of a lanthipeptide is provided. The platform includes: a phagemid including a lanthipeptide display system; a helper phage; and a bacterial host organism configured to express one or more lanthipeptide biosynthesis enzymes.

In the first respect, the lanthipeptide display system includes a fusion gene encoding an open reading frame having a N-terminal secretion signal, a lanthipeptide display peptide and a pIII protein. In one respect, the lanthipeptide display peptide includes a nisin peptide. In another respect, the phagemid is capable of being rescued by the helper phage, wherein the helper phage includes a M13 phage. In this respect, the M13 phage is M13K07. In several respects, the platform includes a bacterial host organism being *E. coli*. In several respects, the one or more lanthipeptide biosynthesis enzymes include NisB or NisC, or a combination thereof.

In a second aspect, a phage for displaying a lanthipeptide is provided. The phage is made according to the platform of any of the respects of the first aspect. The phage is configured to infect a bacterial host organism including a Gram-positive bacterium.

In a third aspect, a platform for cell surface display of a lanthipeptide is provided. The platform includes: a lanthipeptide display system; and a yeast host organism configured to express one or more lanthipeptide biosynthesis enzymes.

In one respect, the lanthipeptide display system includes a fusion gene encoding an open reading frame having a lanthipeptide display peptide and an Aga2 protein. In another respect, the yeast host organism is *S. cerevisiae*. In another respect, the one or more lanthipeptide biosynthesis enzymes include a LanM family enzyme.

In a fourth respect, a lanthipeptide display system is provided. The lanthipeptide display system includes a gene chimera encoding a fusion peptide including a lanthipeptide display peptide and a presentation peptide. The presentation peptide anchors the lanthipeptide display peptide on an outer biological surface. In one respect, the outer biological surface of the cell is selected from a phage surface or a host organism membrane. In another respect, the gene chimera encoding a fusion peptide including a lanthipeptide display peptide and a presentation peptide is expressed from one of a phagemid, a plasmid, a cosmid and a chromosome.

In a fifth aspect, a lanthipeptide library display system is provided. The lanthipeptide library display system includes a lanthipeptide expression library having a plurality of gene chimeras. Each member of the plurality of gene chimeras encodes a fusion peptide including a lanthipeptide display peptide and a presentation peptide. The presentation peptide anchors the lanthipeptide display peptide on an outer biological surface. In this latter respect, the outer biological surface is selected from a phage surface or a host organism membrane. In other respects, each member of the plurality of gene chimeras is expressed from a uniform lanthipeptide expression library selected from one system consisting of a phagemid, a plasmid, a cosmid, and a chromosome.

In a sixth aspect, a method of identifying a lanthipeptide display peptide expressed in vivo from a biological host organism is provided. The method includes several steps. The first step includes preparing a biological host library, wherein each member of the biological host library expresses a gene chimera encoding a fusion peptide including a lanthipeptide display peptide and a presentation peptide. The presentation peptide anchors the lanthipeptide display peptide on an outer biological surface of the biological host organism. The second step includes sorting the biological host library to form a candidate subset of the biological hosts that express the lanthipeptide display peptide. In some respects of the method, the sorting includes using fluorescence-activated cell sorting. In other respects of the method, the sorting includes using immunoassay.

In a seventh aspect, a phagemid including a lanthipeptide display system is provided. In some respects, the lanthipeptide display system includes a fusion gene encoding an open reading frame having a N-terminal secretion signal, a lanthipeptide display peptide and a pIII protein. In some respects, the lanthipeptide display peptide includes a nisin peptide. In other respects, the phagemid is capable of being rescued by the helper phage, wherein the helper phage includes a M13 phage. In these latter respects, the M13 phage is M13K07. In other respects, the phagemid is configured to produce a phage when propagated in a suitable bacterial host organism, wherein the phage is configured to infect a bacterial host organism including a Gram-positive bacterium.

EXAMPLES

Example 1

Molecular Reagents

Oligonucleotide primers for mutagenesis were synthesized by Operon Technologies or Integrated DNA Technologies. A listing of primers is provided in Tables 2 and 3.

TABLE 2

Primers for Phage Display Aspects

| Name [SEQ ID NO.: _] | SEQUENCE (5'→3') |
|---|---|
| KJH_pSG5_FP [SEQ ID NO.: 30] | GCGCGTTGGCCGATTCATTAATGCAGTCAAGCCCGCCGTAGCC |
| KJH_pSG5_RP [SEQ ID NO.: 31] | CCAGTCGGGAAACCTGTCGTGCCAGTTCACCTAGATCCTTTTGGTTCATGTGC |
| KJH_NisA_pTSP3H_FP [SEQ ID NO.: 32] | CCGACGCCGTAGCGGCCGCAGGCAGCAGCCATCACCATC |
| KJH_NisA_pTSP3H_RP [SEQ ID NO.: 33] | ATAATCAAAATCACCGGCGCCTTTGCTTACGTGAATACTACAATGACAAGTTG |
| KJH_pTSP3H_FP [SEQ ID NO.: 34] | ACGTAAGCAAAGGCGCCGGTGATTTTGATTATGAAAAGATGGCAAAC |
| KJH_pTSP3H_RP [SEQ ID NO.: 35] | ATGGCTGCTGCCTGCGGCCGCTACGGCGTCGGTGGCAG |
| ProcM in pRSFDUET-1 NdeI FP [SEQ ID NO.: 36] | GGTTGGTTCATATGGAAAGTCCATCATCTTGG |
| ProcM in pRSFDUET-1 KpnI RP [SEQ ID NO.: 37] | AAGTAGTTGGTACCTTATTCAGTAGGCCAGAGAC |
| Flag_2.8_ProcA_1dr_pSEX81_NcoI_FP [SEQ ID NO.: 38] | AGCCGGCCATGGCCATGGATTATAAGGATGACGACGATAAATTCATGTCAGAAGAACAACTC |
| 2.8_ProcA_1dr_Xiao_library_pept._1_pSEX81_NotI_RP [SEQ ID NO.: 39] | TCCAAACGTGCGGCCGCGCAGTGAACGTTATGTGGGATGGAG |
| 2.8_ProcA_1dr_Xiao_library_pept._1/Factor Xa/pSEX81_NotI RP [SEQ ID NO.: 40] | TCCAAACGTGCGGCCGCGCAGTGAACGTTATTGTGGGATGGAG |

TABLE 3

Primer sequences for random lanthipeptide libraries 1 and 2 (5'-3')[a]

| Name [SEQ ID NO.: _] | SEQUENCE (5'→3') |
|---|---|
| Lib2.8_2_EcoRI-5' [SEQ ID NO.: 41] | AGC CAG GAT CCG AAT TCG ATG TCA GAA GAG CAA CTG AAG GCA TTC CTC AC |
| Lib2.8_leader_NotI-3' [SEQ ID NO.: 42] | TCC CCC AGC CAC ACC TTC CAG CTC |
| Lib1_2.8_NWY_NotI-3' [SEQ ID NO.: 43] | TAA ATA TTG CGG CCG CTT AGC ARW NRW NRW NRW NGG ATG GAG GCA TAG ARW NRW NRW NRW NAC AGG CCG CTC CCC CAG CCA CAC |
| Lib2_2C10S_VWK_NotI-3' [SEQ ID NO.: 44] | TAA ATA TTG CGG CCG CTT AGT AGC A W BMW BMW BMW BMW BMW BMW BMW BMW BAC TGT TGT AGT GAT GGT ATC CCC CAG CC |

[a] N = A, T, C, G (25% molar ratio of each base); R = A, G (50% molar ratio of each base); W = A, T (50% molar ratio of each base); B = C, G, T (33.3% molar ratio of each base).

Taq and Platinum Pfx DNA polymerases, DpnI, restriction endonucleases, and bacteriophage T4 DNA ligase were purchased from Invitrogen. Phusion DNA polymerase was purchased from New England Biolabs (NEB). Cloning vectors (pET and pDuet) were obtained from Novagen. Agarose gel extraction, plasmid mini-prep, and PCR purification kits were purchased from Qiagen. HisTrap IMAC resin was purchased from GE Healthcare Life Sciences. Strep-Tactin resin was purchased from IBA. M13K07 helper phage (NO315S), and anti-M13 pIII monoclonal antibody (E8033S) were obtained from NEB. Monoclonal anti-flag M2 antibody produced in mouse was purchased from Sigma (F3165). HA epitope tag antibody was purchased from Thermo Fisher Scientific. Alexa Fluor 488 goat anti-mouse antibody was purchased from Life Technologies. StrepMAB classic anti-StrepTag II antibody was purchased from IBA. ELISA plates (Nunc), and substrate for enzyme horseradish peroxidase (HRP) in ELISA studies, 1-step ultra TMB-ELISA (34028), was obtained from Thermo Fisher Scientific. Substrate for the HRP for western blot analysis was clarity western ECL substrate from Bio-rad (170-5060). All strains were grown in media acquired from Difco laboratories or Fisher Scientific. Other items procured include isopropyl-1-thio-D-galactopyranoside (IPTG, CalBiochem), iodoacetamide (IAA, Acros Organics), tris(2-carboxyethyl) phosphine hydrochloride (TCEP, Aldrich), and dithiothreitol (DTT, Sigma). Endoproteinases LysC, trypsin, GluC, and Factor Xa were purchased from Roche Applied Science.

Example 2

General Methods

Molecular biological manipulations were carried out using standard techniques. PCR was performed using an automatic thermocycler (PTC 150, MJ Research) and DNA sequencing was performed at the Biotechnology Center of the University of Illinois at Urbana-Champaign (UIUC) or by ACGT, Inc. *E. coli* DH5α cells (UIUC Cell Media Facility) or DH10B-T1$^R$ (New England BioLabs) were used for plasmid preparation. *E. coli* SS320 (Lucigen Corporation) was used for phage production, and *E. coli* BL21 (DE3) cells (Stratagene) were used for protein expression. *S. cerevisiae* EBY100 cells were used for yeast surface display. MALDI-ToF MS analyses were conducted at the Mass Spectrometry Facility (UIUC) using an UltrafleXtreme TOF/TOF (Bruker Daltonics). Liquid chromatography electrospray ionization tandem mass spectrometry (LC/ESI-MS/MS) was carried out and processed using a Synapt ESI quadrupole ToF Mass Spectrometry System (Waters) equipped with an Acquity Ultra Performance Liquid Chromatography (UPLC) system (Waters). ELISA readings were performed with a Synergy H4 reader. Flow cytometry was carried out using a LSR II Flow Cytometer (BD Biosciences).

Example 3

Construction of a NisA-Containing Phagemid

The Tat signal peptide-hexahistidine tag-NisA construct was cloned out of a synthetic gene block (Integrated DNA Technologies) containing the Tat signal sequence from the trimethylamine N-oxide reductase protein followed by a hexahistidine tag and the precursor NisA peptide gene. The pJF3H phagemid was used to provide the backbone of the phagemid including the truncated pIII protein (containing only residues 274-424), phage origin, beta lactamase, and dsDNA origin genes. Primers KJH_NisA_pTSP3H_FP and KJH_NisA_pTSP3H_RP were used to clone the Tat-His$_6$-NisA gene. Primers KJH_pTSP3H_FP and KJH_pTSP3H_RP were used to clone the necessary genes from pJF3H. The PCRs (50 μL) included 1× HF buffer (NEB), Phusion DNA Polymerase (NEB) (0.02 unit/μL), dNTPs (1 mM), template DNA, and primers (0.5 μM each). The amplification was conducted via 30 to 34 cycles of denaturing (98° C. for 15 s), annealing (temperature determined based on the NEB annealing temperature calculator and annealed for 30 s), and extending (72° C. for 45 to 120 s depending on the length of the amplified fragment), then a final elongation step (72° C. for 10 minutes). Both fragments were purified on a 1% agarose gel, purified using the QIAquik gel purification kit (QIAGEN), and a Gibson assembly was then performed to anneal the two cloned fragments into a singe phagemid. The entire Gibson reaction was then transformed into chemically-competent *E. coli* DH10B cells via heat shock, plated on an LB agar plate with 100 μg/mL ampicillin, and grown at 37° C. for 8-18 h. Colonies were picked and incubated in 5 mL of LB-ampicillin medium at 37° C. for 12-20 h, followed by isolation of the plasmids using a QIAprep Spin Miniprep Kit (QIAGEN). The sequences of the resulting plasmids were confirmed by DNA sequencing.

Example 4

Preparation of the Constructs for Peptides Attached to the ProcA Leader 2.8

Cloning of the genes encoding the library of peptides attached to the ProcA 2.8 leader peptide (Table 1) into pSEX81 was performed by using NcoI and NotI cut sites using the primers in Table 5.2, Flag_2.8_ProcA_ldr_pSEX81_NcoI_FP and 2.8_ProcA_ldr_Xiao_library_pept._1pSEX81_NotI_RP (or 2.8_ProcA_ldr_Xiao_library_pept._1/Factor Xa/pSEX81_NotI RP) primers were used as forward and reverse primers to amplify the ProcA 2.8 leader peptide library 1 sequence from template 2.8-peptide_1/pRSF-Duet-1 (see Table 2). The PCRs (50 μL) included 1× HF buffer (Finnzymes), DMSO (4%), Fusion DNA Polymerase (Finnzymes) (0.02 unit/μL), dNTPs (1 mM), template DNA, and primers (1 μM each). The amplification was conducted via 30 cycles of denaturing (98° C. for 10 s), annealing (60° C. for 30 s), and extending (72° C. for 15 s). The final PCR product was confirmed by 2% agarose gel electrophoresis, and the products were purified using QIAquick PCR purification kits (QIAGEN). The resulting DNA fragment and the pSEX81 vector were digested in 1× NEBuffer 4 (New England Biolabs) with NcoI-HF and NotI-HF at 37° C. (for 15 h). The digested products were purified by agarose gel electrophoresis followed by use of a QIAquick gel extraction kit (QIAGEN). The resulting DNA insert was ligated with the digested pSEX81 vector at 16° C. for 15 h using T4 DNA ligase. The ligation reaction mixture was diluted 5 times with water prior to transformation. *E. coli* DH5α cells were transformed with the ligation product via heat shock, plated on LB-ampicilin/0.2% glucose agar plates, and grown at 37° C. for 15 h. Colonies were picked and incubated in 5 mL of LB-ampicillin medium at 37° C. for 15 h, followed by isolation of the plasmids using a QIAprep Spin Miniprep Kit (QIAGEN). The correct sequences of the resulting plasmids were confirmed by DNA sequencing.

Example 5

Preparation of Phage-Displaying NisA and Modified NisA

Chemically competent E. coli SS320 cells (50 µL) were transformed with 50-100 ng of phagemid containing the desired gene, and plated on an LB agar plate containing Amp (100 µg/ml), Tet (10 µg/ml), and 1% w/v glucose. In this step, Amp is required for the phagemid, Tet is required for the F episome coding for the F pilus, which is needed for helper phage infection, and glucose is to prevent the expression of NisA-pIII since it slows down the cell growth overnight at 37° C. After the plates were incubated overnight at 37° C., a colony was picked and grown in 5 mL of 2×YT media (1.6% tryptone, 1.0% yeast extract, 0.5% NaCl, pH: 7, autoclaved) supplemented with Amp (100 µg/ml), Tet (5 µg/ml), and 1% glucose with shaking at 37° C. Then, a 1:20 inoculation of overnight liquid culture into fresh 2×YT media supplemented with Amp (100 µg/ml) was performed to make a culture of total volume 50 or 100 mL. The culture was grown to O.D.$_{600nm}$ of 0.3-0.5. Then M13KO7 was added to a multiplicity of infection of approximately 7 to provide the phage structural genes and isopropyl β-D-1-thiogalactopyranoside (IPTG) was added to a final concentration of 0.8 mM to induced expression of the NisA-pIII fusion protein. Cells were then allowed to grow for one hour with shaking at 37° C. to ensure infection. Kanamycin was then added to kill any uninfected cells and the temperature was reduced to 30° C. to ensure optimal production of phage. The culture was allowed to continue to grow overnight, then the cells were removed by centrifugation at 10500×g. The supernatant was then filtered through 0.22 µM sterile filter to remove any remaining E. coli SS320 contamination and the phage was precipitated from the culture supernatant by adding back ¼ of the total volume as 2.5 M NaCl/20% w/v PEG8000. This was mixed well and allowed to precipitate on ice overnight. The phage was then pelleted by centrifugation at 10500×g. The supernatant was aspirated off and the phage was resuspended in 1.5 mL tris-buffer saline (TBS; 50 mM Tris-Cl (pH 7.5), 250 mM NaCl, autoclaved) solution. The phage was precipitated a second time by adding back ¼ of the total volume as 2.5 M NaCl/20% w/v PEG8000. This was mixed well and allowed to precipitate on ice for at least one hour. The phage was then collected by centrifugation at 10500xg followed by aspiration of the supernatant. The phage pellet was resuspended in a minimal amount of TBS, generally 0.25 to 0.5 mL, and the concentration was determined via a previously determined UV measurement technique (Wiseman, R. L., Berkowitz, S. A. and Day, L. A., "Different arrangements of protein subunits and single-stranded circular DNA in the filamentous bacterial viruses fd and Pf1," J. Mol. Biol., 102, 549-561 (1976); Smith, G. P., "Absorption Spectroscopy and Quantitation of Filamentous Phage" from http://www.biosci.missouri.edu/smithgp/PhageDisplayWebsite/AbsorptionSpectrum.doc accessed on 19 Aug. 2015).

For coexpression of NisA and NisB/C, chemically competent E. coli SS320 cells (50 µL) were transformed with 50-100 ng of phagemid containing the desired gene, and plated on an LB agar plate containing Amp (100 µg/ml), Tet (10 µg/ml), chloramphenicol (25 µg/ml), and 1% w/v glucose. In this step, Amp is required for the phagemid, Tet is required for the F episome coding for the F pilus, which is needed for helper phage infection, and glucose is to prevent the expression of NisA-pIII since it slows down the cell growth overnight at 37° C. After the plates were incubated overnight at 37° C., a colony was picked and grown in 5 mL of 2×YT media (1.6% tryptone, 1.0% yeast extract, 0.5% NaCl, pH: 7, autoclaved) supplemented with Amp (100 µg/ml), Tet (5 µg/ml), chloramphenicol (25 µg/ml), and 1% glucose with shaking at 37° C. Then, a 1:20 inoculation of overnight liquid culture to fresh 2×YT media supplemented with Amp (100 µg/ml) and chloramphenicol (25 µg/ml) was performed to make a culture of total volume 50 or 100 mL. The culture was grown to O.D.$_{600nm}$ of 0.3-0.5. Then M13KO7 was added to a multiplicity of infection of approximately 7 to provide the phage structural genes, arabinose was added to a final concentration of 0.04% w/v, and isopropyl β-D-1-thiogalactopyranoside (IPTG) was added to a final concentration of 0.8 mM to induce expression of the NisA-pIII fusion protein. Cells were then allowed to grow for one hour at 37° C. with shaking to ensure infection. Kanamycin was then added to kill any uninfected cells and the temperature was reduced to 30° C. to ensure optimal production of phage. The culture was allowed to continue to grow overnight, then the cells were removed by centrifugation at 10500×g. The supernatant was then filtered through 0.22 µM sterile filter to remove any remaining E. coli SS320 contamination and the phage was precipitated from the culture supernatant by adding back ¼ of the total volume as 2.5 M NaCl/20% w/v PEG8000. This was mixed well and allowed to precipitate on ice overnight. The phage was then pelleted by centrifugation at 10500×g. The supernatant was aspirated off and the phage was resuspended in 1.5 mL TBS solution. The phage was precipitated a second time by adding back ¼ of the total volume as 2.5 M NaCl/20% w/v PEG8000. This was mixed well and allowed to precipitate on ice for at least one hour. The phage was then collected by centrifugation at 10500×g followed by aspiration of the supernatant. The phage pellet was resuspended in a minimal amount of TBS, generally 0.25 to 0.5 mL, and the concentration was determined via a previously determined UV measurement technique.

Example 6

SDS-PAGE Analysis and Band Excision

Phage (15 µL, 1×10$^{12}$ to 1×10$^{13}$ phage/mL) was mixed with Laemmli protein loading dye. After 5 min incubation at 100° C., 15 µL of this solution was loaded on a 4-20% Tris-Glycine polyacrylamide gel (Bio-Rad). After electrophoresis, the gel was stained with Coomassie blue dye for 15 to 30 minutes then destained for 2 hours or overnight. Bands of interest were excised with a razor blade and placed in separate eppendorf tubes. The Coomassie stain was removed by covering the gel slice in a solution of 50 mM NH$_4$HCO$_3$ in 50% acetonitrile 10 minutes, then aspirating all of the liquid. This step was repeated until the wash liquid no longer appeared blue. Next, the gel slice was flash-frozen and lyophilized until dry, typically 3 hours to overnight. The band was then removed from the lyophilizer and submerged in an ice-cold solution of 100 mM NH$_4$HCO$_3$ with 0.0125 mg/mL trypsin. This mixture was placed on ice and allowed to swell the gel for 1 hour. The tube containing the gel slice swelled in the trypsin digestion mixture was then placed at 37° C. for 12 to 24 hours. After completion of digestion, the digestion mixture was removed and set aside for later analysis. The slice was then submerged in 20 mM NH$_4$HCO$_3$ and sonicated in a water bath for 20 minutes. This solution was then removed and set aside for later analysis. The gel slice was then submerged in 5% formic acid in 50% acetonitrile and again sonicated in a water bath for 20 minutes. This solution was then either spotted directly for MALDI analysis or lyophilized to dryness to save for later analysis.

Example 7

Mass Spectrometry Analysis of Phage Displayed Peptides

Aqueous trypsin-digested peptide solutions extracted from the gel were concentrated via Zip Tip (Millipore) then eluted directly onto the MALDI plate in a 2,5-dihydroxy-benzoic acid matrix (DHB; 20 μg/μL DHB in 70:30 ACN: 0.1% trifluoroacetic acid). The extract from the SDS-PAGE excised band in 5% formic acid in 50% acetonitrile was directly spotted (1 μL) into 2,5-dihydroxybenzoic acid matrix (1 μL) and analyzed via MALDI-ToF MS.

Example 8

Coexpression Studies for Nisin, Lacticin 481, Haloduracin, and Prochlorosins

Production of lanthipeptides nisin, lacticin 481, haloduracin, and prochlorosins and their derivatives such as ProcA2.8-pIII in *E. coli* was performed as described before (Shi, Y. et al. (2012)); however, instead of using 18° C., the cells were grown at 30° C. overnight.

Example 9

Considerations for Lanthipeptide Library Construction

A set of cyclic lanthipeptide libraries were generated by taking advantage of the great sequence tolerance of ProcM. The ProcA peptides contain a leader peptide that is not modified and a core peptide where the posttranslational modifications take place. The modification process of ProcM is likely guided by the conserved leader sequence of the 29 ProcA substrates (Table 4). Therefore, multiple libraries of lanthipeptide substrates were generated by replacing the ProcA core sequence with a peptide sequence of similar length with a partially randomized sequence, while the leader sequence was kept unchanged.

TABLE 4

Sequence alignment of naturally occurring ProcAs.[1]

| | Leader sequence |
|---|---|
| 1.1 | MSEEQLKAFIAKVQADTSLQEQLKAEG--ADVVAIAKAAGFSITTEDL--EKEHR------QTLSDDELEGVAGG |
| 1.2 | MSEEQLKAFIAKVQADPSLQEQLKAEG--ADVVSIAKAAGFSITTEDL--N-SHIT----TKLNLS ELEGVAG |
| 1.3 | MSEEQLK F SKVQSDASLQEQLKVEG--ADVVAIAKAAGFSITTEDL--N-SHR------QNLS DELEGVAGG |
| 1.4 | MSEEQLK F TKVQADTSLQEQLKAEG--ADPVAIAKAAGFAITTEDL--N-SHRQ------NLSDDELEGVAGG |
| 1.5 | MSEEQLK FIAKVQADTSLQEQLKVEG--ADVVAIAKAAGFSITTEDL--N-THR------QNLLSDDELEG HG |
| 1.6 | MSEEQLKAFIAKVQADTSLQEQLKVEG--ADVVAIAKAAGFSIII DFERN-THR------QTLSDDELEGVAGG |
| 1.7 | MSEEQLKAFIAKVQADTSLQEQLKVEG--ADVVAIAKASGEAITTEDL--K-AHQAN---SQKNLSDAELEGVAGG |
| 2.1 | MSEEQLKAFIAKVQAD SLQEQLKAEG--ADVVAIAKAAGFSITTEDW--D-QRP------VRTLSD ELEGAAGG |
| 2.2 | MSEEQLKAFIAKVQADPSLQEQLKAEG--ADTVAIAKAAGFSITTEDL--K-EHRQ------TLSDDELESVAGG |
| 2.3 | MSEEQLKAF EKVKADTSLKEKLKAAKSPEDVV LAKEHGHEFLA K------------SQLS ELEGVAGG |
| 2.4 | MSEEQLKAF AKVQADASLQEQLKAEG--ADVVAIAKAAGFSITTEDL--N-SHRQ------IE DDELEGVAGG |
| 2.5 | MSEEQLKAFIAKVQ DTSLQEQLKAEG--ADVVAIAKAAGEAIIEA---K-AYQ------TRNLSD EL EVAGG |
| 2.6 | MSEEQLKAFIAKVQADTSLQEQLKAEG--ADVVAIAKAAGFAII IEDL--N-NHRQ------NLSDDELEGVAGG |
| 2.7 | MSEEQLKAFIAKVQADTSLQEQLKAEG--ADVVAIAKAAGFSIA EDL--K-THR------QTLSDDD EGVAGG |
| 2.8 | MSEEQLKAF TKVQADTSLQEQLKIEG--ADVVAIAKAAGFSITTEDL--N-SHR------QNLSDDELEGVAGG |
| 2.9 | MSEEQLKAFIAKVQADPSLQEQLKAEG--ADVVAIAKAAGF ITTEDL--K-TAR------QTLSDD LEGVAGG |
| 2.10 | MSEEQLKAFIAKVQAD SLQEQLKAEG--ADPVSIAKAAGF ITTEDL--N-SHRQ------NLSD ELEGAAGG |

TABLE 4-continued

Sequence alignment of naturally occurring ProcAs.[1]

| | |
|---|---|
| 2.11 | MSEEQLKAFIAKVQADTSLQEQLKAEG--ADVVAIAKAAGEAIIKEDL--N-SHR------QTLS DELESVAGG |
| 3.1 | MSEEQLKAFIAKVQADASLQEQLTEG--ADVVAIAKAAGESITTEDL--N-SHRQ------NLSDDELEGVAGG |
| 3.2 | MSEEQLKAFIAKVQADASLQEQLTEG--ADVVAIAKAAGESITTEDL--N-SHRQ------NLSDDELEGVAGG |
| 3.3 | MSEEQLKAFIAKVQ D SLQEQLKAEG--ADVVAIAKAAGE LKQQDL--N-AA------ASELSD ELE ASGG |
| 3.4 | MSEEQLKAFIAKVQ DSLQEQLKAEG--ADVVAIAKAAGESITTEDL--N-THR------QTLSDRELEGVAGG |
| 3.5 | MSEEQLKAF EKVKADTSLQEK LKAA DSDAV VLAKDAGESI A DL--K-NAQ------SE S ELESVAGG |
| 4.1 | MSEEQLKAL IAKVQADTSLQEQLKAEG--ADVVAIAKAAGESITTEDL--K-EHRQTLSVGRQTLS SELEG AGG |
| 4.2 | MSEEQLKAFIAKVQADTSLQEQLKAEG--ADPVAIAKAAGESITTEDL--K-EHRQ------ALSDD LEGVAGG |
| 4.3 | MSEEQLKAFIAKVQADTSLQEQLKAEG--ADVVAIAKAAGE ITTEDL--N-SHRQ------NL DDELEGVAGG |
| 4.4 | MSEEQLKAF EKVK DTSLQEKIQAA DSDAV AIAKEAGEMI A L--K-KAQ------SE S ELESAAGG |
| s.1 | MSEEQLKAF EKVKADTSLQEKLKAA DSDAV VLAKDAGESI A DL--K-NAQ------SE S ELESVAGG |
| s.2 | MSEEQLKAF EKVKADTSLQEKLKAA DSDAV AIAKAAGLMI A DL--T-KAQ------SE SDAELEDAAGG |
| t.1 | -----------------MQEQLKAEG--ADV AIAKAAGESITIEDL--K-EHRK------TLSDAELEGVAGG |

| Core peptide | |
|---|---|
| 1.1 | FFCVQGTANRFTINVC---------------- |
| 1.2 | MDCVSSTAQQTECRPGGPRASYCWDDLR---- |
| 1.3 | GLCTLTSNLAAVCCGGCRRATSE--------- |
| 1.4 | GSSYRNGKCTFGPACPS--------------- |
| 1.5 | GPGCTGGWWAFTDCTAGGGSCEG--------- |
| 1.6 | KSTNGCGCKPGHTLSSFLCTLECWL------- |
| 1.7 | TIGGTIVSITCETCDLLVGKMC---------- |
| 2.1 | CCITGESPGSAPTNDYKCTKGRGPGGCY---- |
| 2.2 | GNDTVITKEYSCYVTSDKGCC----------- |
| 2.3 | MQAGSCNWICFVNGVYINDGRMANKAI----- |
| 2.4 | GCGLGARRETAQCWLSH--------------- |
| 2.5 | APCRPFTDPIYCWRKGEQTIIGRGRSCLYPE- |
| 2.6 | GICVYVNCVLSIRETPSVI------------- |
| 2.7 | AGCYPICDWTSPTRS----------------- |
| 2.8 | AACHNHAPSMPPSYWEGEC------------- |
| 2.9 | TEDGDYTKSISIVVACCRF------------- |
| 2.10 | AGGTIPSLMTGCGWLTGLCVR----------- |
| 2.11 | GRIDTCPAGGGTSEQTGTCC------------ |
| 3.1 | GGKMTVRGRDMSCGCQDYWEDDY--------- |
| 3.2 | GGCDGIRITDKQTVADNTIVPCSCFHQ----- |
| 3.3 | GDTGIQAVLHTAGCYGGTKMCRA--------- |

TABLE 4-continued

Sequence alignment of naturally occurring ProcAs.[1]

3.4  TTAFTGVDTESIAFCCS---------------

3.5  AGVTEATIDAGGGCTFNPCCR----------

4.1  GGGARTKTANVPSDLPVRAPAMSTFAENQT--

4.2  TIVTVTGALISIAAEC----------------

4.3  TASGGCDTSMFCY------------------

4.4  AQSAGGCGICECDNRQSTSCHYPSHG------ s.1  GAQGPACCAAMESSDTRCGWVSWVLSEVVPPQ s.2  AFNHDWGQTTRNYKCETSYCC---------- t.1

[1]The N-terminal leader sequence has high sequence identity, while the C-terminal core peptide is hypervariable. The SEQ ID NOs. for these sequences are as follows: 1.1 [SEQ ID NO.: 45]; 1.2 [SEQ ID NO.: 46]; 1.3 [SEQ ID NO.: 47]; 1.4 [SEQ ID NO.: 48]; 1.5 [SEQ ID NO.: 49]; 1.6 [SEQ ID NO.: 50]; 1.7 [SEQ ID NO.: 51]; 2.1 [SEQ ID NO.: 52]; 2.2 [SEQ ID NO.: 53]; 2.3 [SEQ ID NO.: 54]; 2.4 [SEQ ID NO.: 55]; 2.5 [SEQ ID NO.: 56]; 2.6 [SEQ ID NO.: 57]; 2.7 [SEQ ID NO.: 58]; 2.8 [SEQ ID NO.: 59]; 2.9 [SEQ ID NO.: 60]; 2.10 [SEQ ID NO.: 61]; 2.11 [SEQ ID NO.: 62]; 3.1 [SEQ ID NO.: 63]; 3.2 [SEQ ID NO.: 64]; 3.3 [SEQ ID NO.: 65]; 3.4 [SEQ ID NO.: 66]; 3.5 [SEQ ID NO.: 67]; 4.1 [SEQ ID NO.: 68]; 4.2 [SEQ ID NO.: 69]; 4.3 [SEQ ID NO.: 70]; 4.4 [SEQ ID NO.: 71]; s.1 [SEQ ID NO.: 72]; s.2 [SEQ ID NO.: 73]; and t.1 [SEQ ID NO.: 74].

Considering that lanthipeptides are ribosomally synthesized peptides, we focused on constructing a genetically encoded library, by co-expressing the precursor lanthipeptide substrates with ProcM in heterologous host cells, which generated the modified lanthipeptides in vivo. This library can be directly applied to in vivo selection system such as genetic reverse two-hybrid system (RTHS), which couples disruption of protein complexes to the expression of reporter genes required for cell survival, or it can be used to display peptides on the surface of the host or phage.

To ensure the quality of ring formation, our initial strategy utilized a fixed scaffold of specific thioether ring structures, while randomizing the amino acid sequence within the rings. For this example, scaffolds were developed based on ProcA2.8 and 2C10S, which generated two 7-amino acid rings and one 14-residue ring, respectively (Table 5).

TABLE 5

Types of lanthipeptide libraries

| Name [SEQ ID NO.:] | Leader sequence | Rationale[1] |
|---|---|---|
| Library 1 procA2.8 leader[2] [SEQ ID NO.: 75] | A A C X X X X X S M P P S X X X X X C | X = NWY (Based on ProcA2.8 scaffold) |
| Library 2 procA2.8 leader [SEQ ID NO.: 76] | Y H H Y N S X X X X X X X X X X X X C Y | X = VWK (Based on 2C10S scaffold) |

[1]For triplet codons, X = NWY, wherein N is A, G, C or T;

W is A or T; and

Y is T or C, and

X = VWK where V is G, C or A;

W is A or T; and

K is G or T.

[2]procA2.8 leader: MSEEQLKAFLTKVQADTSLQEQLKIEGADVVAIAKAAGFSITTEDLNSHRQNLSDDELEGVAGG [SEQ ID NO.: 77].

These scaffolds were employed to construct two libraries with rings at fixed positions. Other scaffolds based on the other 28 ProcA sequences can readily be devised.

The next step was to design the DNA triplet codons that encode the randomized amino acids within the rings. There are four criteria that need to be met to ensure the quality of the libraries: (1) the randomized amino acids preferably do not contain Ser/Thr/Cys that might disturb the original ring scaffold by forming additional/alternative rings; (2) the randomized amino acids do not contain potential stop codons that will result in truncated peptides; (3) there should not be significant bias encoding certain amino acids over others. In other words, all encoded amino acids should be as equally represented as possible in a first round; (4) we strived for reasonable diversity of the library, ideally close to or greater than $10^8$ library variants which is normally the limitation resulting from transformation efficiency in E. coli.

Taking all four considerations together, the initial optimized DNA triplet codons that encode each randomized amino acid were designed as NWY (GATC, AT, TC) for library 1 and VWK (GCA, AT, GT) for library 2, resulting in the utilization of unique sets of amino acids as shown in Table 6A, B. Other triplet codon sets can easily be devised.

TABLE 6A

Predicted amino acid composition for each library codon for Library 1[a]

| | Amino acid | | Number of codons |
|---|---|---|---|
| D | Asp | Aspartic acid | 2 |
| F | Phe | Phenylalanine | 2 |
| H | His | Histidine | 2 |
| I | Ile | Isoleucine | 2 |
| L | Leu | Leucine | 2 |
| N | Asn | Asparagine | 2 |
| V | Val | Valine | 2 |
| Y | Tyr | Tyrosine | 2 |

[a]NWY, wherein N = GACT, W = AT, Y = TC; number of possible codon variants: 16; number of possible amino acid variants: 8.

TABLE 6B

Predicted amino acid composition for each library codon for Library 2[b]

| | Amino acid | | Number of codons |
|---|---|---|---|
| D | Asp | Aspartic acid | 1 |
| E | Glu | Glutamic acid | 1 |
| H | His | Histidine | 1 |
| I | Ile | Isoleucine | 1 |
| K | Lys | Lysine | 1 |
| M | Met | Methionine | 1 |
| N | Asn | Asparagine | 1 |
| Q | Gln | Glutamine | 1 |
| L | Leu | Leucine | 2 |
| V | Val | Valine | 2 |

[b]VWK, wherein V = GAC, W = AT, K = GT; number of possible codon variants: 12; number of possible amino acid variants: 10.

Example 10

Construction of Lanthipeptide Library

The pRSFDuet-1 vector with procM inserted into MCS2 was used for library vector construction. pRSFDUET-1 vector containing the procA2.8 leader sequence was used as template for PCR amplification of ProcA2.8 leader followed by randomized library sequences. Library PCR primers (Table 3, synthesized using the hand-mixing option and PAGE purification by IDT) were designed that added an EcoRI restriction site to the 5' end and a NotI restriction site to the 3' end. The PCR products were digested with the appropriate restriction enzymes and purified using a Qiagen PCR purification kit. The pRSFDUET-1 vector was digested with the same restriction enzymes and an additional enzyme SbfI to minimize vector self-ligation, dephosphorylated with alkaline phosphatase, and gel-purified. The digested vector was added to a ligation reaction containing T4 ligase and the insert DNA. Electrocompetent E. coli DH5α cells were transformed with the ligation mixture and plated on LB-agar containing kanamycin (50 mg $L^{-1}$) to screen for positive clones. Clones were sequenced at ACGT, Inc.

Example 11

Overexpression, Purification and Modification Assay for Library Samples

The library samples were overexpressed and purified using the method described in Shi, Y. Yang, X. Garg, N.; van der Donk, W. J Am Chem Soc. 133:2338-41 (2011). Soluble peptides typically yielded about 10 mg of final product per liter of overexpressed cells from LB broth.

To monitor dehydration, select purified library peptides were dissolved (final concentration 1 mg $mL^{-1}$) in LysC or GluC assay buffer containing 50 mM HEPES, pH 7.5-8.0. LysC/GluC was added to a final concentration of 0.05 mg $mL^{-1}$ to remove most of the leader peptide. Cleavage reactions were incubated at RT for 3 h and subjected to MALDI-ToF MS analysis.

To monitor cyclization, a chemical modification step following the enzymatic assay is required since cyclization does not result in a change in mass. For most applications using MALDI-TOF MS, modification has been accomplished using the thiol modification agents iodoacetamide (IAA) or N-ethylmaleimide (NEM) that allow analysis of cyclization at two different pH values. A 5-μL aliquot of the above assay mixture was added to 15 μL of IAA assay buffer with a final concentration of 50 mM Tris, 50 mM IAA, 1-3 mM TCEP, pH 8.5, or NEM assay buffer with a final concentration of 50 mM Tris, 25 mM NEM, 1-3 mM TCEP, pH 6.3. The assay solution was incubated in the dark at RT for 4 h (for IAA assay) or 37° C. for 10 min (for NEM assay) and subjected to MALDI-ToF MS. Non-enzymatic cyclization under these conditions is very slow and not important (Mukherjee S, van der Donk WA: Mechanistic Studies on the Substrate-Tolerant Lanthipeptide Synthetase ProcM. J. Am. Chem. Soc. 2014, 136:10450-10459).

The ring topology of select lanthipeptides can be deduced from their MS fragmentation pattern. A sample of 5 μL of each protease cleavage reaction mixture was injected to a BEH C8 column (1.7 μm, 1.0×100 mm), and the fully modified product was purified by UPLC using a gradient of 3% mobile phase B (0.1% formic acid in methanol) to 97% mobile phase B in mobile phase A (0.1% formic acid in water) over 12 min. Mass spectra were acquired in ESI positive mode in the range of 50-2000 m/z. The capillary voltage was 3500 V, and the cone voltage was 40 V. The other parameters used were as follows: 120° C. source temperature; 300° C. desolvation temperature, 150 L/h cone gas flow, and 600 L/h desolvation gas flow. A transfer collision energy of 4 V was used for both MS and tandem MS, while the trap collision energy was set to 6 V for MS and a 20-55 V ramp for MSMS depending on the peptide. Glu-fibrinopeptide B (Sigma) was directly infused as the lock mass. The tandem mass spectra were processed with MaxEnt3 and analyzed by Protein/Peptide Editor in BioLynx 4.1. The software for analyzing both precursor-ion and fragment-ion mass was set to report any mass within 0.3 amu of the calculated expected values.

Following library construction, 6-7 samples from each library were tested for dehydration and cyclization. Each of them yielded the desired ring formation, indicating that the scaffolds are robust (see Table 7).

Example 12

Construction of Yeast Expression Plasmids

Synthetic double stranded DNA containing yeast-codon optimized genes for the expression of Aga2-LctA, Aga2-ProcA 2.8, Aga2-HalA2, and LctA-Aga2 were obtained from Integrated DNA Technologies and inserted into the

TABLE 7

Results of the Libraries 1 and 2

| ID [SEQ ID NO.:_] | Core peptide sequence[a] | Major dehydration product by MS | Cyclization product by MS[b] | Conclusion |
|---|---|---|---|---|
| 2.8-1 [SEQ ID NO.: 78] | AACFNVHISMPPSHNNVHC | -2 H$_2$O | No IAA adduct | 2 rings |
| 2.8-10 [SEQ ID NO.: 79] | AACVNHLLSMPPSLNDLNC | -2 H$_2$O | No IAA adduct | 2 rings |
| 2.8-11 [SEQ ID NO.: 80] | AACDVNLHSMPPSLDFFVC | -2 H$_2$O | No IAA adduct | 2 rings |
| 2.8-15 [SEQ ID NO.: 81] | AACVFHFDSMPPSYLDDDC | -2 H$_2$O | No IAA adduct | 2 rings |
| 2.8-3 [SEQ ID NO.: 82] | AACNIDFLSMPPSIHHILC | -2 H$_2$O | No NEM adduct | 2 rings |
| 2.8-5 [SEQ ID NO.: 83] | AACNIYYISMPPSHHFVYC | -2 H$_2$O | No NEM adduct | 2 rings |
| Hit 3-3 [SEQ ID NO.: 84] | AACLHFFLSMPPSHVLDIC | -2 H$_2$O | No NEM adduct | 2 rings |
| 2C10 [SEQ ID NO.: 85] | YHHYNCYNFNLFNNYNNNSY | -1 H$_2$O | No IAA adduct | 1 ring |
| 2C10S [SEQ ID NO.: 86] | YHHYNSYNFNLFNNYNNNCY | -1 H$_2$O | No IAA adduct | 1 ring |
| 2C10-3 [SEQ ID NO.: 87] | YHHYNSDVLLDLKKNDLECY | GluC: -1 H$_2$O | No IAA adduct | 1 ring; no proteolysis in ring |
| 2C10-10 [SEQ ID NO.: 88] | YHHYNSVINHLNDLQEKLCY | GluC: -0 H$_2$O | No IAA adduct | 1 ring; 1 proteolysis in ring[c] |
| 2C10-11 [SEQ ID NO.: 89] | YHHYNSQQVVIIQDNQVDCY | GluC: -1 H$_2$O | No IAA adduct | 1 ring; no proteolysis in ring |
| 2C10-14 [SEQ ID NO.: 90] | YHHYNSMIKHKEHDHMIICY | GluC: -1 H$_2$O, -0 H$_2$O | No IAA adduct | 1 ring; 1 proteolysis in ring[c] |

[a]GluC cleavage sites inside the ring are underlined.
[b]As determined by reactions with electrophiles iodoacetamide (IAA) or N-ethylmaleimide (NEM).
[c]If proteolysis is observed in the ring, it provides additional evidence for cyclization since the mass of the peptide increases by 18 Da (H$_2$O) without cleavage of the peptide (because the thioether holds the two proteolytic fragments together).

Proteolytic cleavage inside the 14-residue ring was observed during leader peptide removal by GluC in two samples from Library 2 (Table 7). This further confirmed the ring had been formed. When glutamate was immediately next to the lanthionine, no cleavage was observed. The higher sensitivity of the larger ring structures may be due to the less restricted conformation of the loop region of the 14-residue ring, which makes it more likely to fit in the active site of the protease. Comparatively, very few proteolytic cleavages were observed for the smaller 7-residue rings. This observation indicates that although Library 2 can generate cyclic peptides as desired, it may not be as stable against proteolytic degradation as the other libraries. This illustrates the advantages of polycyclic peptides over monocyclic peptides and/or the advantages of smaller rings over larger rings. EcoRI and XhoI sites of pCT302 by isothermal assembly. The constructs were confirmed by DNA sequencing.

Synthetic double stranded DNA containing yeast codon optimized genes encoding LctM, ProcM, and HalM2 with an N-terminal secretion signal from mating factor α, and a C-terminal endoplasmic reticulum retention tag were obtained from Integrated DNA Technologies and inserted into the XbaI and XhoI sites of pAG415-Gal-ccdB-DsRed by isothermal assembly. The constructs were confirmed by DNA sequencing.

Example 13

Construction of Aga2-LanA and LanA-Aga2 *E. coli* Expression Plasmids

The genes encoding Aga2-LctA, Aga2-ProcA 2.8, Aga2-HalA2, and LctA-Aga2 were amplified from their yeast expression constructs using primers pET_Aga2-lctA Strep F1/R1, pET_Aga2-2.8 F1/R1, pET_HalA2 F/R, and lctA-Aga2 F1/R2 respectively (Table 8). The PCR products were inserted into the BamHI and XhoI sites of pETDuet (Aga2-LctA, Aga2-ProcA 2.8), the NdeI and EcoRI sites of pET28 (Aga2-HalA2), or the NcoI and XhoI sites of pET28 (LctA-Aga2) by isothermal assembly. All constructs were confirmed by DNA sequencing.

The genes encoding LctM, ProcM, and HalM2 were amplified from pETDuet-LctM, pET28-ProcM, and pRSF-Duet-HalM2 respectively with primers pTRC33-lctM F1/R1, trcProcM F1/R1, and pTRC-HalM2 F/R respectively (Table 8). The PCR products were inserted into the BamHI and HindIII sites of pTRC33 by isothermal assembly. All constructs were confirmed by DNA sequencing.

Example 14

Coexpression of LanA Fusions and LanMs in *E. coli*

*E. coli* BL21(de3) cells were transformed with the appropriate Aga2 LanA fusion expression plasmid and that of the associated LanM. Overnight Terrific Broth (TB) cultures (5 mL) of the freshly transformed cells were used to inoculate TB cultures (1L) in 4 L shake flasks to $OD_{600}$=0.05. The cultures were grown at 37° C. with shaking at 200 rpm until they reached $OD_{600}$=0.8, at which point they were chilled on ice for 20 min. Protein expression was then induced by the addition of IPTG (0.2 mM) and the cultures were incubated overnight at 18° C. Cell pellets were harvested by centrifugation at 4,500×g for 20 min at 4° C. and stored at -80° C. until use.

Example 15

Purification and Characterization of Aga2 LanA Fusions from *E. coli*

Frozen cell pellets were thawed and resuspended in lysis buffer (8 M urea, 100 mM sodium phosphate, 10 mM Tris, pH 8.0) at 5 mL/g cell paste. Cells were then lysed by sonication and insoluble material was removed by centrifugation at 12,000×g for 20 min at 4° C. The supernatant was passed over HisTrap IMAC resin (~1 mL resin/g cell paste). The resin was then washed with 20-25 column volumes of lysis buffer, washed further with 20-25 column volumes of lysis buffer adjusted to pH 6.3, and the protein of interest was eluted with lysis buffer adjusted to pH 4.5. Fractions containing the protein of interest were identified by absorbance at 280 nm, pooled, and concentrated in an Amicon spin concentrator with a molecular weight cutoff of 15 kDa to a concentration of approximately 5-10 mg/mL. The Aga2 LanA fusions were then diluted 4-fold to give a urea concentration of 2 M and incubated with the appropriate protease (Aga2-LctA: trypsin; Aga2-ProcA 2.8 and Aga2-HalA2: Glu-C; LctA-Aga2: trypsin and Glu-C) at a ratio of 10:1 Aga2 LanA fusion:protease and 1 mM TCEP. The incubation was allowed to run at room temperature overnight. The cleaved core peptide was purified by reverse phase HPLC and analyzed by MALDI-TOF mass spectrometry. The NEM assays were performed on these peptides as described above.

Example 16

Expression and Analysis of Aga2 LanA Fusions in Yeast

*S. cerevisiae* EBY100 was transformed with the appropriate Aga2 LanA fusion expression plasmid and that of the associated LanM. Overnight cultures (5 mL) were grown from a single colony in synthetic dropout media lacking leucine and tryptophan with glucose as the carbon source. These culture were used to inoculate cultures of the same media to $OD_{600}$=1 and the cultures were incubated at 30° C. with shaking at 250 rpm. When cultures reached $OD_{600}$=6, the cells were harvested by centrifugation at 3,000×g for 5 min at room temperature. The cell pellet was washed with leucine and tryptophan synthetic dropout media with galactose as the carbon source and resuspended in the same (5 mL) to induce protein expression. The cultures were incubated at 20° C. with shaking for 48 h. Approximately $1\times10^7$ cells were harvested by brief centrifugation and washed with 1 mL of phosphate buffered saline with 0.1% (w/v) bovine serum albumin (PBS+BSA). Cells were resuspended in 100 µL PBS+BSA. StrepMAB (4 µL of 1 mg/mL stock) was added to the cells which were then incubated at room temperature for 1 h. Cells were pelleted and washed with 1 mL of ice cold PBS+BSA and resuspended in 100 µL of ice cold PBS+BSA. Alexa Fluor 488 goat anti-mouse antibody (4 µL of 1 mg/mL stock) was added to the cells and they were incubated on ice and in the dark for 30 min. The cells were again pelleted and washed with 1 mL of ice cold PBS+BSA and analyzed on a BD LSR II flow cytometer using the instrument's default settings for Alexa Fluor 488.

Example 17

Isolation of Surface Displayed Aga2-HalA2

Expression of Aga2-HalA2 and HalM2 was induced as described above in a 1 L culture. Cells were harvested by centrifugation at 3,000×g for 20 min at 4° C. The cells were then washed with 100 mL of 150 mM sodium chloride and resuspended in buffer containing 1 M sorbitol, 100 mM Tris, and 1 mM TCEP at pH 8 at 5 mL/g cell paste. The cells were subsequently incubated at 4° C. for 1 h with gentle shaking. The cells were then removed by centrifugation and the supernatant was loaded onto Strep-Tactin resin (approximately 1 mL). The resin was washed with buffer consisting of 100 mM Tris and 150 mM sodium chloride, pH 8 until the $A_{280}$ of the eluent dropped below 0.05. The protein of interest was then eluted from the column with buffer consisting of 100 mM Tris, 8 M urea, and 2.5 mM desthiobiotin pH 8. The eluent was pooled and concentrated in an Amicon spin concentrator with a molecular weight cutoff of 30 kDa. The Aga2-HalA2 was then digested and analyzed MALDI-TOF MS as described above.

TABLE 8

| Oligonucleotides used for the yeast display aspects. | |
|---|---|
| Name [SEQ ID NO.: _] | Sequence (5'→3') |
| Aga2-LctA Strep F1 [SEQ ID NO.: 91] | TTGGTCTCATCCACAATTCGAAAAACTGCAGGCTAGTGGTGGTGG |
| Aga2-LctA Strep R1 [SEQ ID NO.: 92] | CGAATTGTGGATGAGACCAATTGGATCTACCTTCAATCGTCGAGCT ATTGTCC |

TABLE 8-continued

Oligonucleotides used for the yeast display aspects.

| Name [SEQ ID NO.:_] | Sequence (5'→3') |
|---|---|
| pET_Aga2-2.8 F1 [SEQ ID NO.: 93] | TTATATTTCCAGGGTAGCCAGCAGGAACTGACAACTATATGCG |
| pET_Aga2-2.8 R1 [SEQ ID NO.: 94] | GCAGCGGTTTCTTTACCAGACTCGATCACAAACATTCACCTTCCC |
| pET28-HAIA2 F [SEQ ID NO.: 95] | TGGTGCCGCGCGGCAGCCATCAGGAACTGACAACTATATGCGAG |
| pET28-HAIA2 R [SEQ ID NO.: 96] | TGTCGACGGAGCTCGAATTCTTAGCACTGGCTTGTACACTTTG |
| IctA-Aga2 F1 [SEQ ID NO.: 97] | CTTTAAGAAGGAGATATACCATGAAGGAACAAAACTCCTTCAACTTG |
| IctA-Aga2 R2 [SEQ ID NO.: 98] | GGTGGTGGTGGTGCTCGAGTTCAGTGATGATGATGGTGGTGGTG |
| pTRC33-LctM F1 [SEQ ID NO.: 99] | ATTTCACACGAGCTCGGTACCCGGGCCAGACGTAATCTAATAAGGAGGTAC |
| pTRC33-LctM R1 [SEQ ID NO.: 100] | TCTTCTCTCATCCGCCAAAACAGCCTTAATCAACATATGGCATTAAGACTCC |
| trcProcM F1 [SEQ ID NO.: 101] | CAATTTCACACGAGCTCAGGAGATATACCATGGAAAGTCCATCATCTTGGAAAAC |
| trcProcM R1 [SEQ ID NO.: 102] | TCCGCCAAAACAGCCTTATTCAGTAGGCCAGAGACCAG |
| pTRC-HaIM2 F [SEQ ID NO.: 103] | AGCTCGGTACCCGGGGATCCCAGGAGATATACCATGAAAACTCCTCTAACAAGTG |
| pTRC-HaIM2 R [SEQ ID NO.: 104] | TCTCATCCGCCAAAACAGCCAAGCTTTTATCTGTCATGAATTCTCAACTC |

All of the patents, patent applications, patent application publications and other publications recited herein are hereby incorporated by reference as if set forth in their entirety.

The present invention has been described in connection with what are presently considered to be the most practical and preferred aspects. However, the invention has been presented by way of illustration and is not intended to be limited to the disclosed aspects. Accordingly, one of skill in the art will realize that the invention is intended to encompass all modifications and alternative arrangements within the spirit and scope of the invention as set forth in the appended claims.

What is claimed is:

1. A lanthipeptide display system, comprising:
a gene chimera encoding a fusion peptide comprising a lanthipeptide display peptide and a presentation peptide,
wherein the presentation peptide anchors the lanthipeptide display peptide on an outer biological surface,
wherein the lanthipeptide display peptide comprises a lanthionine amino acid moiety, wherein the lanthipeptide display peptide or presentation peptide comprises SEQ ID NOs.: 9, 75 and 76.

2. The lanthipeptide display system of claim 1, wherein the outer biological surface is selected from a phage surface or a host organism membrane.

3. The lanthipeptide display system of claim 1, wherein the gene chimera encoding a fusion peptide comprising a lanthipeptide display peptide and a presentation peptide is expressed from one of a phagemid, a plasmid, a cosmid, and a chromosome.

4. A lanthipeptide library display system, comprising:
a lanthipeptide expression library comprising a plurality of gene chimeras, wherein each member of the plurality of gene chimeras encodes a fusion peptide comprising a lanthipeptide display peptide and a presentation peptide,
wherein the presentation peptide anchors the lanthipeptide display peptide on an outer biological surface,
wherein the lanthipeptide display peptide comprises a lanthionine amino acid moiety, wherein the lanthipeptide display peptide or presentation peptide comprises SEQ ID NOs.: 9, 75 and 76.

5. The lanthipeptide library display system of claim 4, wherein the outer biological surface is selected from a phage surface or a host organism membrane.

6. The lanthipeptide library display system of claim 4, wherein each member of the plurality of gene chimeras is expressed from a uniform lanthipeptide expression library selected from one system consisting of a phagemid, a plasmid, a cosmid and a chromosome.

* * * * *

UNITED STATES PATENT AND TRADEMARK OFFICE
CERTIFICATE OF CORRECTION

PATENT NO. : 11,149,270 B2
APPLICATION NO. : 15/326751
DATED : October 19, 2021
INVENTOR(S) : van der Donk et al.

It is certified that error appears in the above-identified patent and that said Letters Patent is hereby corrected as shown below:

In the Specification

Column 1, Line 19, for "GM-58822" should read -- GM-058822 --.

Signed and Sealed this
Eighteenth Day of October, 2022

Katherine Kelly Vidal
*Director of the United States Patent and Trademark Office*